United States Patent
Holloway et al.

(10) Patent No.: US 12,188,051 B2
(45) Date of Patent: Jan. 7, 2025

(54) COMPOSITIONS AND METHODS FOR OBTAINING VASCULARIZED HUMAN INTESTINAL ORGANOID TISSUE, AND RELATED USES THEREOF

(71) Applicant: The Regents of the University of Michigan, Ann Arbor, MI (US)

(72) Inventors: Emily Holloway, Ann Arbor, MI (US); Jason Spence, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 465 days.

(21) Appl. No.: 17/332,532

(22) Filed: May 27, 2021

(65) Prior Publication Data
US 2021/0371815 A1 Dec. 2, 2021

Related U.S. Application Data

(60) Provisional application No. 63/030,621, filed on May 27, 2020.

(51) Int. Cl.
*C12N 5/071* (2010.01)

(52) U.S. Cl.
CPC .......... *C12N 5/069* (2013.01); *C12N 2501/11* (2013.01); *C12N 2501/115* (2013.01); *C12N 2501/155* (2013.01); *C12N 2501/16* (2013.01); *C12N 2501/165* (2013.01); *C12N 2501/999* (2013.01); *C12N 2513/00* (2013.01)

(58) Field of Classification Search
CPC ................ C12N 5/069; C12N 2501/11; C12N 2501/115; C12N 2501/155; C12N 2501/16; C12N 2501/165; C12N 2501/999; C12N 2513/00; C12N 2506/23
See application file for complete search history.

(56) References Cited

U.S. PATENT DOCUMENTS

| 7,326,572 B2 | 2/2008 | Fisk et al. |
| 7,510,876 B2 | 3/2009 | D'Amour et al. |

OTHER PUBLICATIONS

Kyle W McCracken et al., Generating human intestinal tissue from pluripotent stem cells in vitro, Nat Protoc.; 6(12): 1920-1928; ( Year: 2011).*
Wimmer et al., Human blood vessel organoids as a model of diabetic vasculopathy; Nature vol. 565, pp. 505-510 (2019) (Year: 2016).*
Holloway et al., Differentiation of human intestinal organoids with endogenous vascular endothelial cells; (bioRxiv 2020.03.15. 991950; Posted Mar. 15, 2020; (Year: 2020).*
Yong-Ri Jin et al., The R-spondin family of proteins: Emerging regulators of WNT signaling; The International Journal of Biochemistry & Cell Biology 44 (2012) 2278-2287 (Year: 2012).*
Zhang et al. Human iPSC-Derived Posterior Gut Progenitors Are Expandable and Capable of Forming Gut and Liver Organoids; vol. 10, Issue 3, Mar. 13, 2018, pp. 780-793 (Year: 2018).*
Silva-García et al. Wnt/b-Catenin Signaling as a Molecular Target by Pathogenic Bacteria; Front. Immunol. 10:2135 (Year: 2019).*
Chi, J.T., 2003. Endothelial cell diversity revealed by global expression profiling. Proceedings of the National Academy of Sciences, 100(19), pp. 10623-1062 (Year: 2003).*
Zhang, R.R., Koido, M., Tadokoro, T., Ouchi, R., Matsuno, T., Ueno, Y., Sekine, K., Takebe, T. and Taniguchi, H., 2018. Human iPSC-derived posterior gut progenitors are expandable and capable of forming gut and liver organoids. Stem Cell Reports, 10(3), pp .780-793. (Year: 2018).*
Holloway et al. Differentiation of Human Intestinal Organoids with Endogenous Vascular Endothelial Cells; Developmental Cell 54, 516-528, Aug. 24, 2020 (Year: 2020).*
Aird et al., Phenotypic heterogeneity of the endothelium: II. Representative vascular beds. Circ Res. Feb. 2, 2007;100(2):174-90.
Becht et al., Dimensionality reduction for visualizing single-cell data using UMAP. Nat. Biotechnol. 37, 38-47.
Blondel et al., Fast unfolding of communities in large networks. Journal of Statistical Mechanics: Theory and Experiment, 2008 (10), P10008. 12 pages.
Camp et al., Multilineage communication regulates human liver bud development from pluripotency. Nat. Publ. Gr. 109, 1-22.
Capeling et al., Nonadhesive Alginate Hydrogels Support Growth of Pluripotent Stem Cell-Derived Intestinal Organoids. Stem Cell Reports. Feb. 12, 2019;12(2):381-394.
Chi et al., Endothelial cell diversity revealed by global expression profiling. Proc Natl Acad Sci U S A. Sep. 16, 2003;100(19):10623-8.
Combes et al., Single-cell analysis reveals congruence between kidney organoids and human fetal kidney. Genome Med. Jan. 23, 2019;11(1):3. 15 pages.
Cortez et al., Transplantation of human intestinal organoids into the mouse mesentery: A more physiologic and anatomic engraftment site. Surgery. Oct. 2018;164(4):643-650.
Czerniecki et al., High-Throughput Screening Enhances Kidney Organoid Differentiation from Human Pluripotent Stem Cells and Enables Automated Multidimensional Phenotyping. Cell Stem Cell. Jun. 1, 2018;22(6):929-940.e4.
Czerwinski et al., In vitro and in vivo development of the human intestine at single cell resolution. BioRxiv 2020. 2020.01.31. 928788. 21 pages.
Daniel et al., Spatiotemporal heterogeneity and patterning of developing renal blood vessels. Angiogenesis. Aug. 2018;21(3):617-634.
De Val et al., Transcriptional control of endothelial cell development. Dev Cell. Feb. 2009;16(2):180-95.

(Continued)

*Primary Examiner* — Christopher M Babic
*Assistant Examiner* — Masudur Rahman
(74) *Attorney, Agent, or Firm* — Casimir Jones, S.C.; Robert A. Goetz

(57) ABSTRACT

The invention disclosed herein generally relates to methods and systems for converting stem cells into specific tissue(s) or organ(s) through directed differentiation. In particular, the invention disclosed herein relates to methods and systems for promoting vascularized human intestinal organoid tissue having an intestine-specific EC transcriptional signature from hindgut spheroid tissue produced in vitro from the described methods.

9 Claims, 35 Drawing Sheets

(56) References Cited

OTHER PUBLICATIONS

Ding et al., Endothelial-derived angiocrine signals induce and sustain regenerative lung alveolarization. Cell. Oct. 28, 2011;147(3):539-53.
Ding et al., Inductive angiocrine signals from sinusoidal endothelium are required for liver regeneration. Nature. Nov. 11, 2010;468(7321):310-5.
Feng et al., Single Cell Analysis of Endothelial Cells Identified Organ-Specific Molecular Signatures and Heart-Specific Cell Populations and Molecular Features. Front Cardiovasc Med. Nov. 26, 2019;6:165. 13 pages.
Ferguson et al., Mechanisms of endothelial differentiation in embryonic vasculogenesis. Arterioscler Thromb Vasc Biol. Nov. 2005;25(11):2246-54.
Ferrara et al., Heterozygous embryonic lethality induced by targeted inactivation of the VEGF gene. Nature. Apr. 4, 1996;380(6573):439-42.
Finkbeiner et al., Generation of tissue-engineered small intestine using embryonic stem cell-derived human intestinal organoids. Biol Open. Oct. 12, 2015;4(11):1462-72.
Finkbeiner et al., Transcriptome-wide Analysis Reveals Hallmarks of Human Intestine Development and Maturation In Vitro and In Vivo. Stem Cell Reports. Jun. 3, 2015;4(6):1140-1155.
Freedman et al., Modelling kidney disease with CRISPR-mutant kidney organoids derived from human pluripotent epiblast spheroids. Nat Commun. Oct. 23, 2015;6:8715. 13 pages.
Fujii et al., Human Intestinal Organoids Maintain Self-Renewal Capacity and Cellular Diversity in Niche-Inspired Culture Condition. Cell Stem Cell. Dec. 6, 2018;23(6):787-793.e6.
Hatch et al., Spatiotemporal mapping of vascularization and innervation in the fetal murine intestine. Dev Dyn. Jan. 2015;244(1):56-68.
Hill et al., Bacterial colonization stimulates a complex physiological response in the immature human intestinal epithelium. Elife. Nov. 7, 2017;6:e29132. 35 pages.
Hill et al., Real-time Measurement of Epithelial Barrier Permeability in Human Intestinal Organoids. J Vis Exp. Dec. 18, 2017;(130):56960. 10 pages.
Holloway et al., Biologically inspired approaches to enhance human organoid complexity. Development. Apr. 16, 2019;146(8):dev166173. 13 pages.
Homan et al., Flow-enhanced vascularization and maturation of kidney organoids in vitro. Nat Methods. Mar. 2019;16(3):255-262.
Kalucka et al., Single-Cell Transcriptome Atlas of Murine Endothelial Cells. Cell. Feb. 20, 2020;180(4):764-779.e20.
Kao et al., Endothelial cells control pancreatic cell fate at defined stages through EGFL7 signaling. Stem Cell Reports. Feb. 10, 2015;4(2):181-9.
Kreitzer et al. A robust method to derive functional neural crest cells from human pluripotent stem cells. Am J Stem Cells. Jun. 30, 2013;2(2):119-31.
Lammert et al., Induction of pancreatic differentiation by signals from blood vessels. Science. Oct. 19, 2001;294(5542):564-7.
Lammert et al., Role of endothelial cells in early pancreas and liver development. Mech Dev. Jan. 2003;120(1):59-64.
Lazarus et al., A perfusion—independent role of blood vessels in determining branching stereotypy of lung airways. Development. Jun. 2011;138(11):2359-68.
Lee et al., Lung stem cell differentiation in mice directed by endothelial cells via a BMP4-NFATc1-thrombospondin-1 axis. Cell. Jan. 30, 2014;156(3):440-55.
Leslie et al., Persistence and toxin production by Clostridium difficile within human intestinal organoids result in disruption of epithelial paracellular barrier function. Infect Immun. Jan. 2015;83(1):138-45.
Low et al., Generation of Human PSC-Derived Kidney Organoids with Patterned Nephron Segments and a De Novo Vascular Network. Cell Stem Cell. Sep. 5, 2019;25(3):373-387.e9.
Mansour et al., An in vivo model of functional and vascularized human brain organoids. Nat Biotechnol. Jun. 2018;36(5):432-441.
Marcu et al., Human Organ-Specific Endothelial Cell Heterogeneity. iScience. Jun. 29, 2018;4:20-35.
Matsumoto et al., Liver organogenesis promoted by endothelial cells prior to vascular function. Science. Oct. 19, 2001;294(5542):559-63.
McCracken et al., Modelling human development and disease in pluripotent stem-cell-derived gastric organoids. Nature. Dec. 18, 2014;516(7531):400-4.
McInnes et al., UMAP: Uniform Manifold Approximation and Projection for Dimension Reduction. arXiv: 1802.03426. 63 pages.
Menon et al., Single-cell analysis of progenitor cell dynamics and lineage specification in the human fetal kidney. Development. Aug. 30, 2018;145(16):dev164038. 9 pages.
Miller et al., In Vitro and In Vivo Development of the Human Airway at Single-Cell Resolution. Dev Cell. Apr. 6, 2020;53(1):117-128.e6.
Munera et al., Differentiation of Human Pluripotent Stem Cells into Colonic Organoids via Transient Activation of BMP Signaling. Cell Stem Cell. Jul. 6, 2017;21(1):51-64.e6.
Nolan et al., Molecular signatures of tissue-specific microvascular endothelial cell heterogeneity in organ maintenance and regeneration. Dev Cell. Jul. 29, 2013;26(2):204-19.
Orlova et al., Generation, expansion and functional analysis of endothelial cells and pericytes derived from human pluripotent stem cells. Nat Protoc. 2014;9(6):1514-31.
Ouchi et al., Modeling Steatohepatitis in Humans with Pluripotent Stem Cell-Derived Organoids. Cell Metab. Aug. 6, 2019;30(2):374-384.e6.
Patsch et al., Generation of vascular endothelial and smooth muscle cells from human pluripotent stem cells. Nat Cell Biol. Aug. 2015;17(8):994-1003.
Pedregosa et al., Scikit-learn: Machine learning in Python. J. Mach. Learn. Res. 2011. 12, 2825-2830.
Rafii et al., Angiocrine functions of organ-specific endothelial cells. Nature. Jan. 21, 2016;529(7586):316-25.
Risau et al., Vasculogenesis. Annu Rev Cell Dev Biol. 1995;11:73-91.
Sato et al., Long-term expansion of epithelial organoids from human colon, adenoma, adenocarcinoma, and Barrett's epithelium. Gastroenterology. Nov. 2011;141(5):1762-72.
Schlieve et al., Neural Crest Cell Implantation Restores Enteric Nervous System Function and Alters the Gastrointestinal Transcriptome in Human Tissue-Engineered Small Intestine. Stem Cell Reports. Sep. 12, 2017;9(3):883-896.
Shalaby et al., Failure of blood-island formation and vasculogenesis in Flk-1-deficient mice. Nature. Jul. 6, 1995;376(6535):62-6.
Spence et al., Directed differentiation of human pluripotent stem cells into intestinal tissue in vitro. Nature. Feb. 3, 2011;470(7332):105-9.
Spence et al., Sox17 regulates organ lineage segregation of ventral foregut progenitor cells. Dev Cell. Jul. 2009;17(1):62-74.
Sriram et al., Efficient differentiation of human embryonic stem cells to arterial and venous endothelial cells under feeder- and serum-free conditions. Stem Cell Res Ther. Dec. 30, 2015;6:261. 17 pages.
Takasato et al., Kidney organoids from human iPS cells contain multiple lineages and model human nephrogenesis. Nature. Oct. 22, 2015;526(7574):564-8.
Takebe et al., Massive and Reproducible Production of Liver Buds Entirely from Human Pluripotent Stem Cells. Cell Rep. Dec. 5, 2017;21(10):2661-2670.
Takebe et al., Vascularized and functional human liver from an iPSC-derived organ bud transplant. Nature. Jul. 25, 2013;499(7459):481-4.
Tsai et al., A Method for Cryogenic Preservation of Human Biopsy Specimens and Subsequent Organoid Culture. Cell Mol Gastroenterol Hepatol. May 30, 2018;6(2):218-222.e7.
Tsai et al., In vitro patterning of pluripotent stem cell-derived intestine recapitulates in vivo human development. Development. Mar. 15, 2017;144(6):1045-1055.
Van Beijnum et al., Isolation of endothelial cells from fresh tissues. Nat Protoc. 2008;3(6):1085-91.

(56) References Cited

OTHER PUBLICATIONS

Van Den Berg et al., Renal Subcapsular Transplantation of PSC—Derived Kidney Organoids Induces Neo-vasculogenesis and Significant Glomerular and Tubular Maturation In Vivo. Stem Cell Reports. Mar. 13, 2018;10(3):751-765.

Vila Ellis et al., Epithelial Vegfa Specifies a Distinct Endothelial Population in the Mouse Lung. Dev Cell. Mar. 9, 2020;52(5):617-630.e6.

Watson et al., An in vivo model of human small intestine using pluripotent stem cells. Nat Med. Nov. 2014;20(11):1310-4.

Wells et al., How to make an intestine. Development. Feb. 2014;141(4):752-60.

Wigle et al., An essential role for Prox1 in the induction of the lymphatic endothelial cell phenotype. EMBO J. Apr. 2, 2002;21(7):1505-13.

Wigle et al., Prox1 function is required for the development of the murine lymphatic system. Cell. Sep. 17, 1999;98(6):769-78.

Wimmer et al., Human blood vessel organoids as a model of diabetic vasculopathy. Nature. Jan. 2019;565(7740):505-510.

Wolf et al., SCANPY: large-scale single-cell gene expression data analysis. Genome Biol. Feb. 6, 2018;19(1):15. 5 pages.

Workman et al., Engineered human pluripotent-stem-cell-derived intestinal tissues with a functional enteric nervous system. Nat Med. Jan. 2017;23(1):1-29.

\* cited by examiner

FIG. 1A-E

FIG. 3A-E
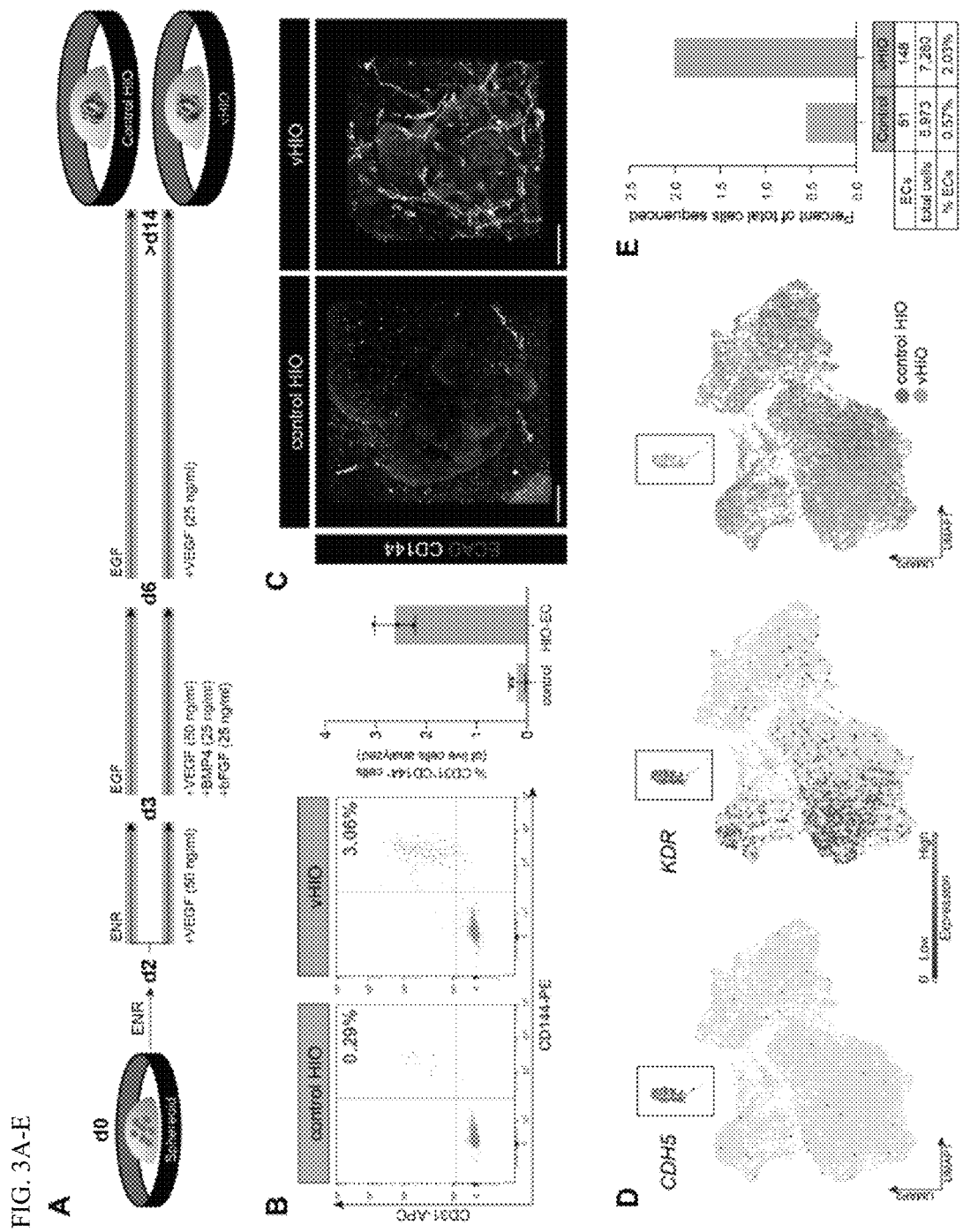

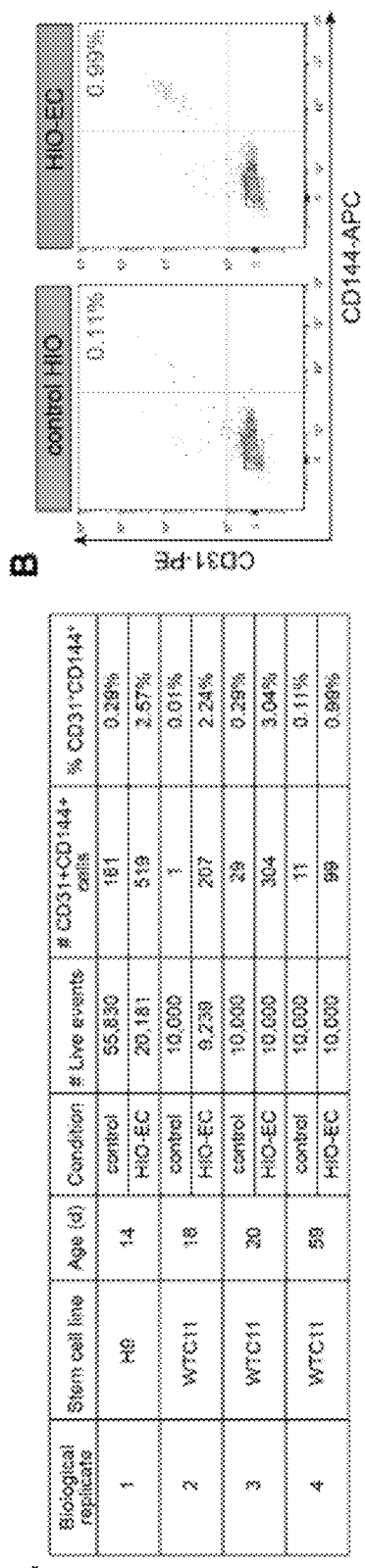
FIG. 4A-C

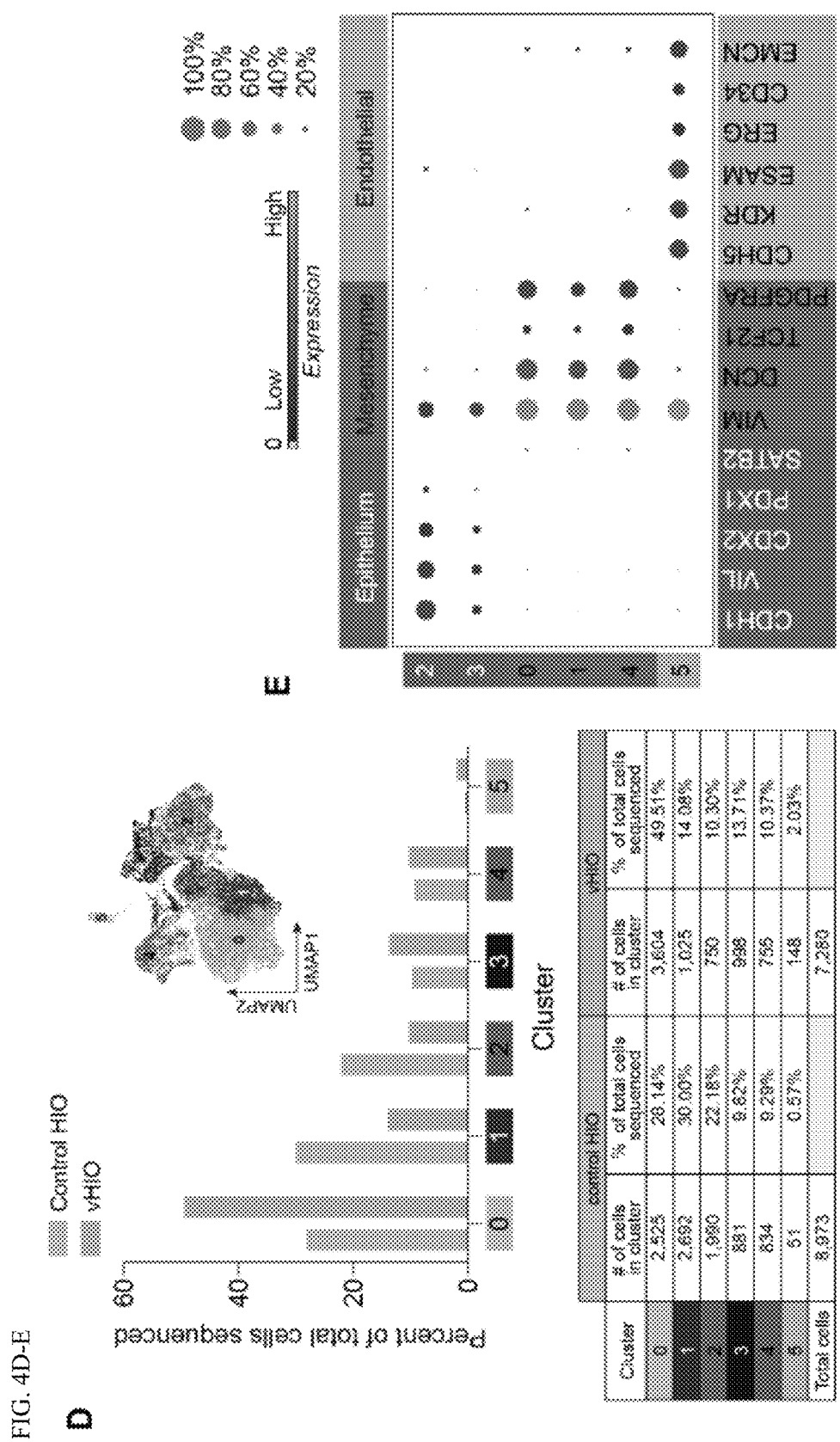
FIG. 4D-E

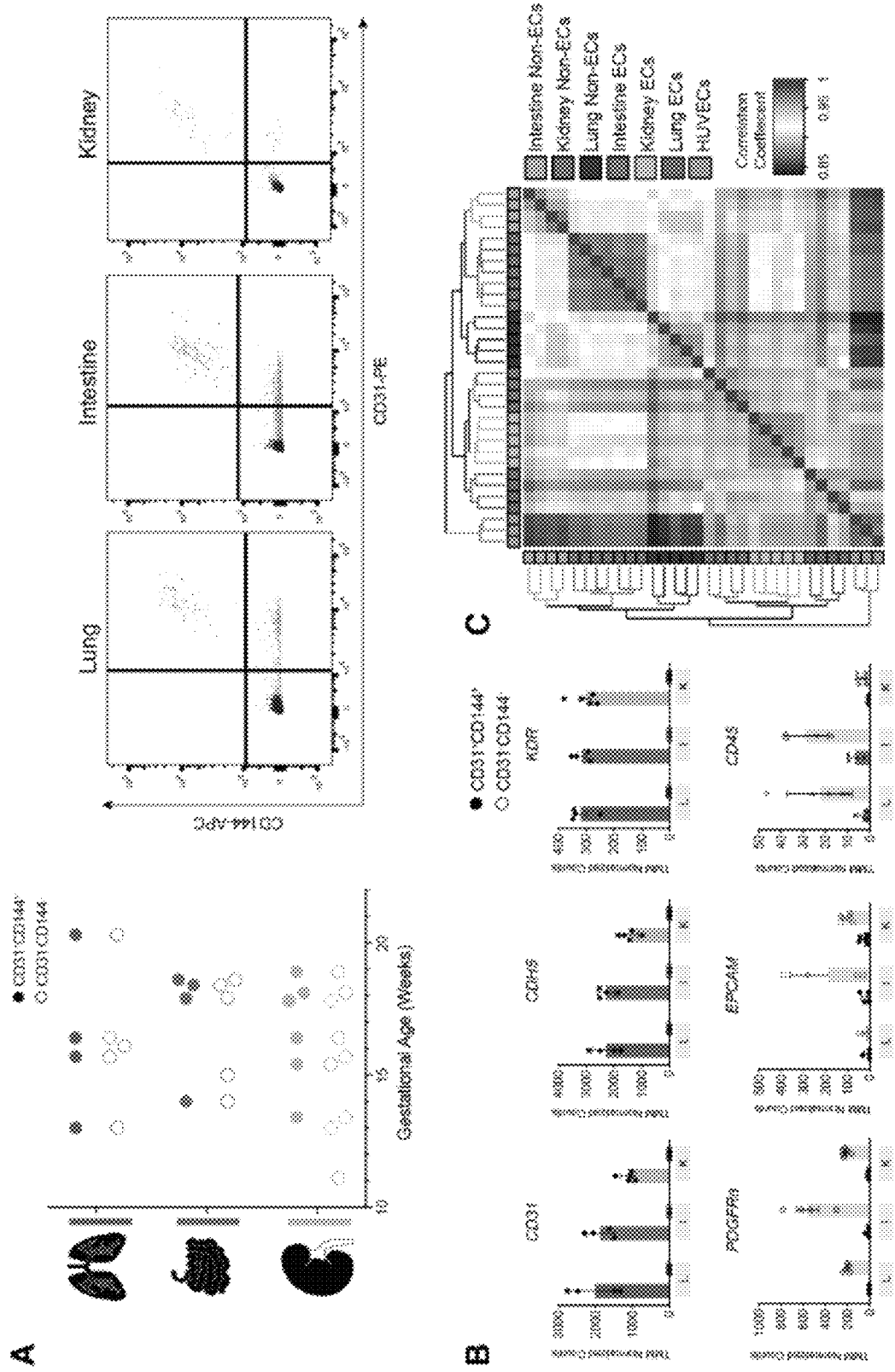
FIG. 5A-C

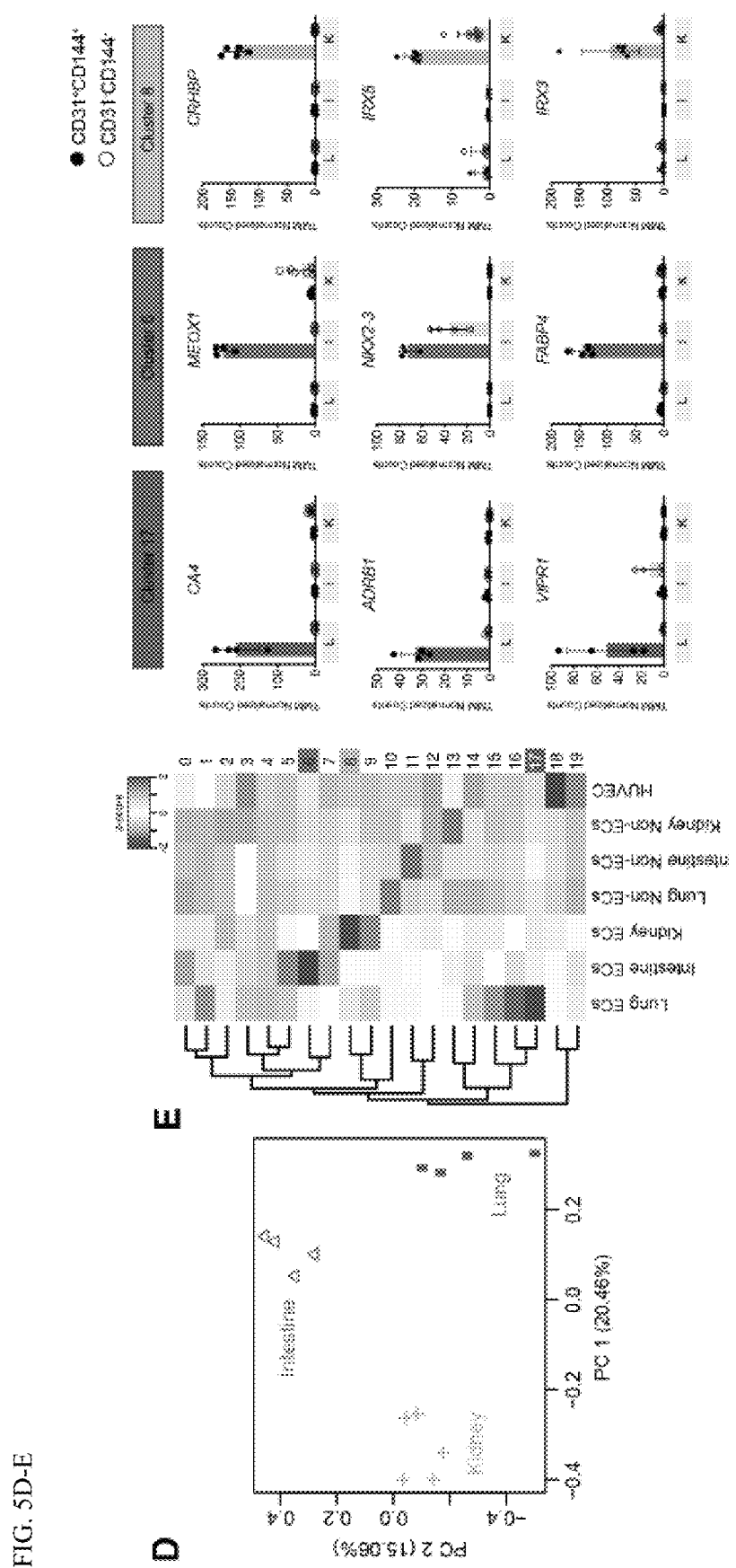
FIG. 5D-E

FIG. 6A-H
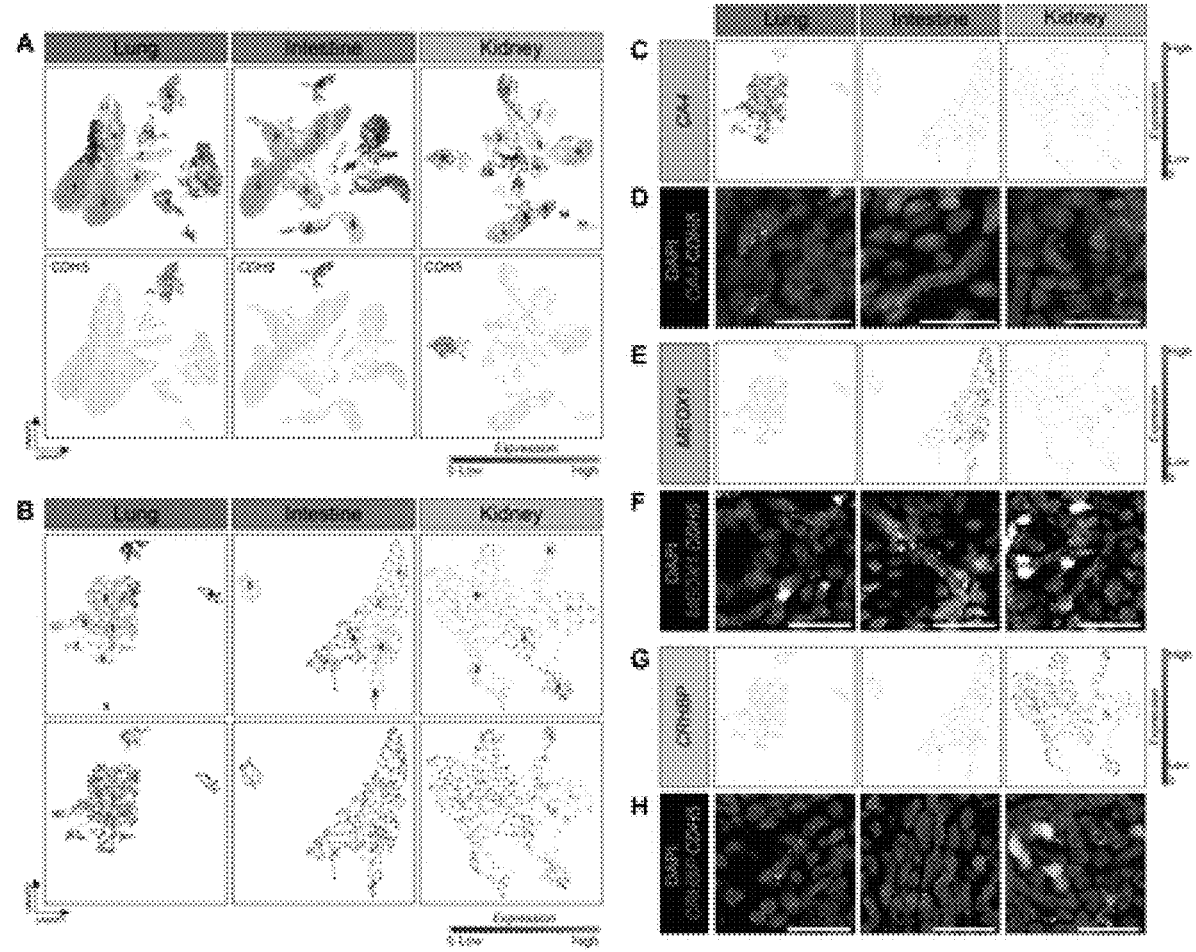

FIG. 7A-B
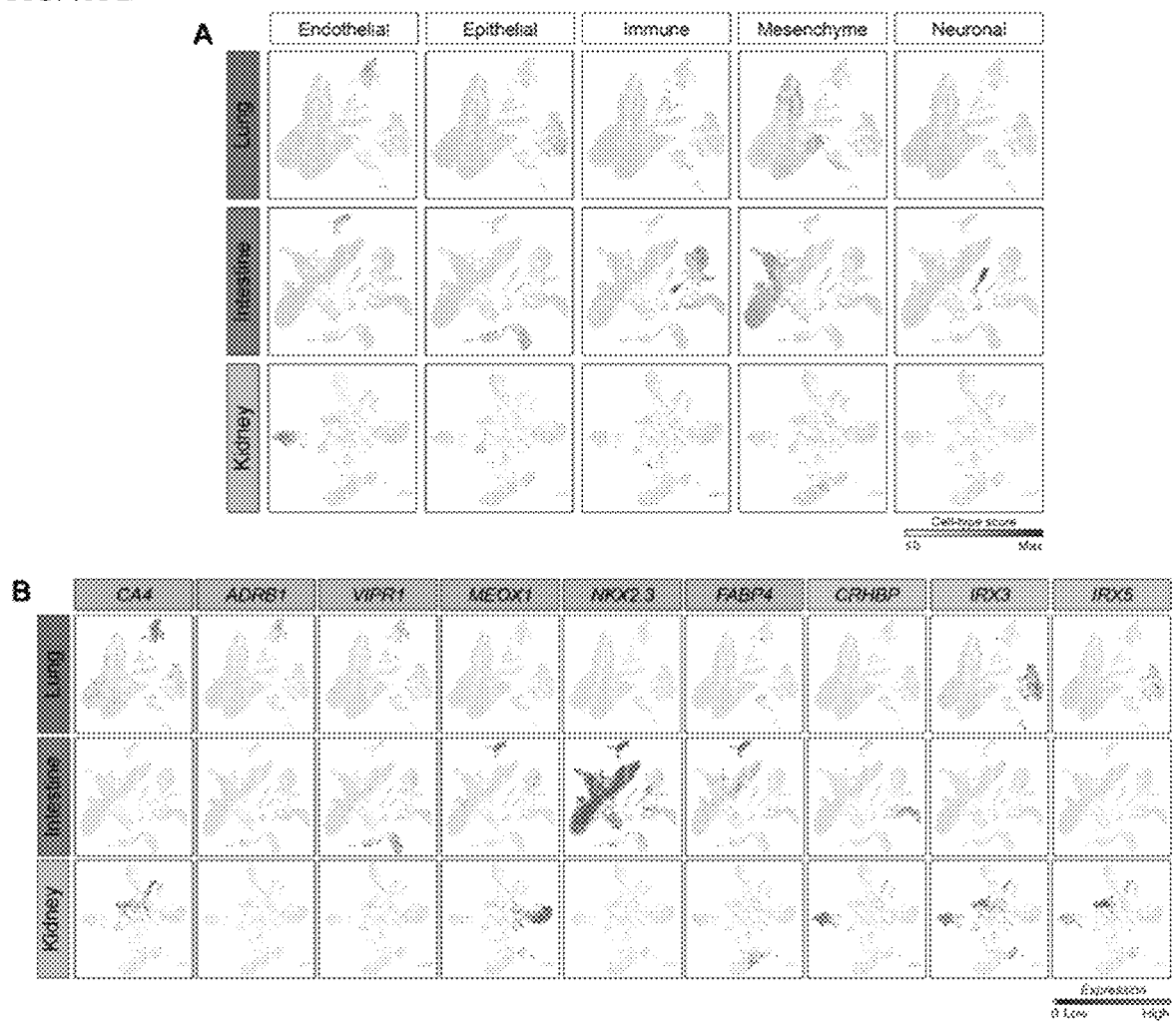

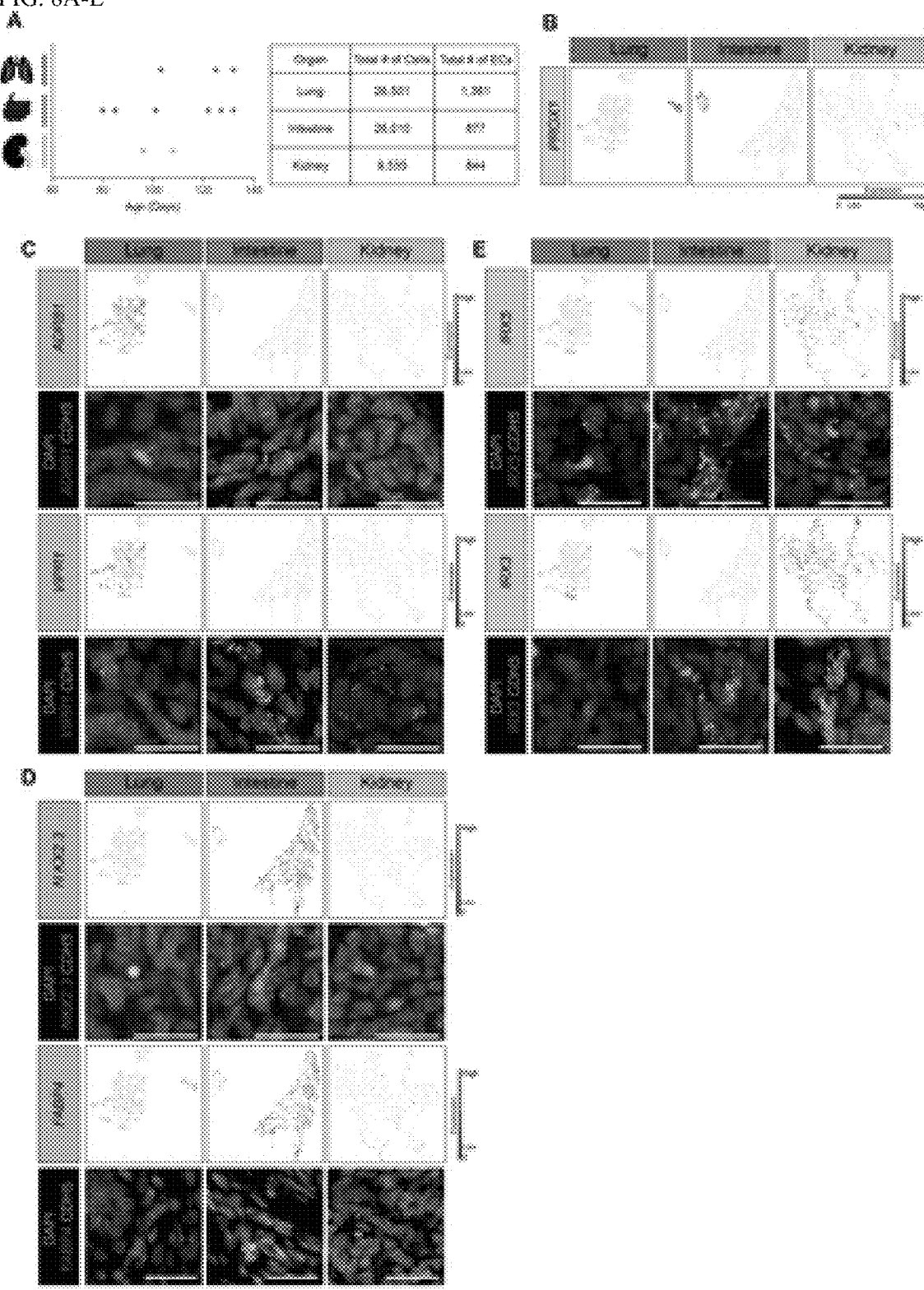
FIG. 8A-E

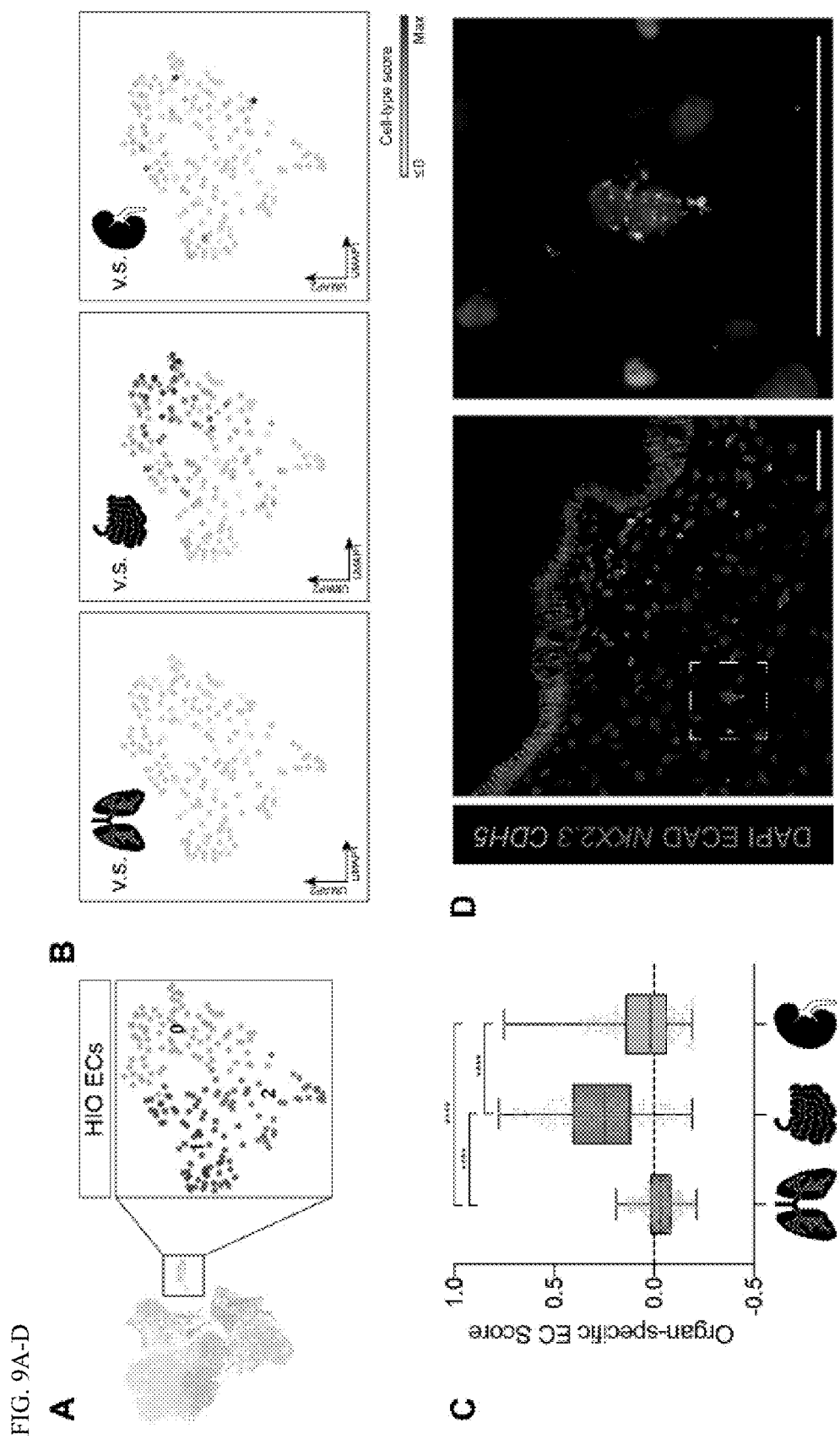
FIG. 9A-D

FIG. 11

| Cluster 0 | Cluster 1 | Cluster 2 | Cluster 3 | Cluster 4 |
|---|---|---|---|---|
| AAED1 | A4GALT | AC000123.2 | 9-Mar | ABCD4 |
| ABI3 | ABCG1 | AC000123.4 | AC005540.3 | ABHD17A |
| AC007743.1 | AC007952.5 | AC003080.4 | AC009950.1 | ABHD6 |
| AC025171.1 | AC007952.6 | AC046143.3 | AC108488.4 | AC005519.4 |
| AC027682.1 | AC098617.1 | AC113404.1 | ADAMTS7P4 | AC005740.6 |
| AC093818.1 | AC142391.3 | ADAMTSL1 | AFDN | AC006129.1 |
| AC096921.2 | ACP2 | AHNAK | AJ006995.3 | AC008264.4 |
| ACR | ACVRL1 | AKIP1 | AMPD3 | AC013271.3 |
| ACTN4 | ADAM10 | ANKH | APOL2 | AC015688.3 |
| ADA | AGAP3 | AP000962.2 | ARHGEF6 | AC069368.3 |
| ADAM15 | AL358113.1 | AP001442.2 | ATP2A3 | AC073046.25 |
| ADAM17 | AP2A2 | AP1S2 | BAIAP2-AS1 | AC092839.4 |
| AGPAT2 | APH1A | APP | BATF | AC135178.7 |
| AKAP2 | ARHGEF10 | ASAP1-IT2 | BBC3 | ADAM19 |
| ALPK3 | ARHGEF12 | ASAP2 | BMP2 | ADARB1 |
| ANXA2R | ATP11A | ATP11C | BTN3A2 | ADCY4 |
| ARAP3 | ATP13A2 | BLOC1S3 | BTN3A3 | ADGRF5 |
| ARHGAP17 | C22orf34 | C2CD2 | C12orf77 | ADGRF5P1 |
| ARHGAP23 | CABP4 | CARD6 | C19orf66 | AFAP1L1 |
| ARHGAP29 | CAMK2G | CASP7 | C1QTNF6 | AFF1 |
| B3GNT5 | CAMTA2 | CCNY | C1orf21 | AIM1 |
| BEND7 | CCND1 | CD300E | CD81 | AKT3 |
| BMPR2 | CD93 | CD55 | CD83 | AL031664.1 |
| BNIP2 | CDK9 | CDC42BPB | CEP112 | ALS2CL |
| C17orf49 | CDR2L | COLGALT1 | CH507-42P11.8 | AP001189.4 |
| C17orf62 | CFLAR | COTL1 | CHSY3 | APLNR |
| CBL | CFLAR-AS1 | CREG2 | CLDN15 | APOL1 |
| CCDC188 | CHST7 | CTD-2035E11.3 | CMPK2 | APOL3 |
| CCDC85A | CLDN5 | CTD-2201E18.3 | CPEB3 | AQP1 |
| CCDC85B | CLEC1A | CTD-3099C6.9 | CTD-2326C4.1 | ARHGEF15 |
| CD109 | CTA-414D7.1 | DAB2 | CTD-2369P2.5 | ARHGEF3 |
| CD58 | CTC-457L16.1 | DEAF1 | CTD-2503I6.1 | ARHGEF7 |
| CDC37 | CTC-457L16.2 | DEGS1 | CXCL2 | ARRDC1 |
| CDC42EP1 | CTC-523E23.3 | DOCK4-AS1 | CXCL3 | ASB9 |
| CDC42SE2 | CTD-2012K14.3 | ERVFRD-1 | DDX60 | ATXN3 |
| CDH5 | CTD-3113P16.5 | EXOC1 | DGAT1 | B2M |
| CDK11B | CTIF | FBXL8 | DOCK8 | BCL6B |
| CEACAM19 | CTNND1 | FRMD4B | DTX3L | BICD1 |

FIG. 11 (cont'd)

| CHFR | CTSD | GFOD1 | DUSP5 | BTN2A2 |
|---|---|---|---|---|
| CLEC14A | DGKH | GGT5 | ENGASE | C8orf4 |
| CMIP | DNM2 | HOXB7 | ETS2 | C8orf58 |
| CNPPD1 | DOCK9 | HTRA1 | FCGRT | CARD10 |
| CRIP2 | DPYSL3 | ICAM3 | FGR | CASKIN2 |
| CTA-243E7.2 | DUSP22 | IL4R | FNBP1 | CASP12 |
| CTD-2282P23.2 | DUSP6 | IL6ST | GAB3 | CC2D2B |
| CTHRC1 | EEF2K | ITGB5 | GABRE | CCL16 |
| CTNNA1 | EGFL7 | KIF3C | GATSL3 | CCM2L |
| CTTNBP2NL | EPB41L4A | LAMA4 | GBP3 | CD200 |
| CYP51A1P3 | F11R | LRRC70 | GLUL | CD40 |
| CYYR1-AS1 | FAM124B | LST1 | GRASP | CDC42-IT1 |
| DAGLB | FAM127C | MICALL2 | GRK5 | CDH8 |
| DDX60L | FAM26E | MIS18BP1 | GRK5-IT1 | CEACAM21 |
| DENND3 | FAM78A | NAV1 | HERC6 | CHD7 |
| DGKZ | FBXW4P1 | NAV3 | HLA-L | CHST12 |
| DNMT3B | FGD6 | NEK6 | HSF4 | CHST15 |
| DUSP7 | FLI1 | NETO2 | HSPA2 | CNPY3 |
| DYSF | FLOT2 | NIN | HVCN1 | CORO7 |
| EGLN2 | FSCN1 | NLK | IER5 | CPEB2 |
| EHD4-AS1 | GATA2 | NR3C2 | IFI6 | CPNE2 |
| ELF1 | GATA2-AS1 | NUMB | IFIH1 | CPNE8 |
| ELF4 | GIMAP4 | PDCL | IFIT2 | CRAMP1 |
| ELK4 | GIT1 | PDIA5 | IFIT3 | CTA-212A2.1 |
| EML3 | GMFG | PIGZ | IFNAR1 | CTA-221G9.12 |
| EMP1 | GRAP | PPM1F | IL10RB | CTA-243E7.1 |
| ENOX2 | GRAPL | PTGS1 | IL16 | CTB-39G8.3 |
| ERG | GRN | RAP1B | IQSEC1 | CTC-510F12.2 |
| ERVK3-1 | GUK1 | RASSF3 | KB-1980E6.2 | CTD-2647L4.4 |
| ESAM | HOMER3 | RBBP4P1 | KLF3 | CXorf36 |
| ETV6 | HSPBAP1 | RHBDF2 | KLF4 | CYFIP1 |
| EVA1C | HSPC324 | ROM1 | LDLRAD4 | CYYR1 |
| FAM107A | HTR1DP1 | RP11-104N10.2 | LINC00921 | DDX58 |
| FAM219A | HYAL2 | RP11-114F10.3 | LINC00963 | DOCK6 |
| FAM69B | ISY1-RAB43 | RP11-127L20.3 | LINC01128 | DOK3 |
| FAM72A | JAM3 | RP11-229P13.2 | LMF1 | EFNA1 |
| FAM72B | KLC1 | RP11-392B6.1 | MDFIC | ELK3 |
| FAM91A1 | KLHL5 | RP11-420L9.5 | MFSD7 | ELMO1-AS1 |

FIG. 11 (cont'd)

| | | | | |
|---|---|---|---|---|
| FGD4 | LIMK2 | RP11-63G10.4 | MMP24 | EMCN |
| FHL3 | LIMS1 | RP11-73M18.7 | MMP25 | EML1 |
| FLJ27354 | LIMS3 | RP11-817I4.2 | MMP25-AS1 | EPHB4 |
| FRMD8 | LINC00176 | RP11-876N24.4 | MOB3C | ERICH1 |
| FUT11 | LMBR1 | RP11-946L16.2 | MPRIP-AS1 | ETS1 |
| FZD6 | LRRFIP1 | RP3-508I15.18 | MYO15B | EXD3 |
| GAB2 | MAP3K11 | RP5-1184F4.5 | NAPRT | EXOC3L1 |
| GCNT2 | MAP3K3 | RP5-849H19.2 | NIPAL2 | FAM110D |
| GFOD2 | MAP4K2 | SDCBP | NKILA | FAM65A |
| GJD3 | MAPK6PS3 | SERPINB6 | NR3C1 | FES |
| GNPTAB | MARS2 | SETD7 | OLFML2A | FGD5 |
| GRPEL2 | MESDC1 | SGK1 | OPTN | FGD5P1 |
| HDAC7 | MICALL1 | SLC16A7 | OSBPL7 | FLT4 |
| HECW2 | MKRN5P | SLC8B1 | OSMR | FMNL3 |
| HHEX | MYD88 | SLK | PALM | FNBP1L |
| HIP1R | NECAP2 | SMAGP | PARP9 | FRAT1 |
| HSPD1P16 | NSRP1P1 | SMCR5 | PDK4 | FRAT2 |
| HSPG2 | NTHL1 | SNCG | PGM5 | FRYL |
| HUS1B | OAZ3 | SP100 | PGM5P4 | FUT1 |
| ICA1 | PCAT19 | ST6GAL1 | PHLDA1 | FYN |
| IFNAR2 | PEA15 | STAB1 | PON3 | GBP4 |
| IGFBP2 | PECAM1 | TAP2 | PSMB10 | GDPD3 |
| INAFM2 | PHACTR4 | TCAF2 | PSMB8 | GDPD5 |
| INF2 | PIEZO1 | TLR4 | PSMB9 | GIMAP1 |
| INPP1 | PIP5K1C | TMEM233 | PTPRN2 | GIMAP1-GIMAP5 |
| IQCJ-SCHIP1 | PLA2G16 | TMEM256-PLSCR3 | RAG1 | GIMAP2 |
| IQCJ-SCHIP1-AS1 | PLAC4 | TMEM87B | RAI2 | GIMAP6 |
| ISG15 | PLEKHA1 | TNFRSF1A | RAMP2-AS1 | GIMAP7 |
| ITGA6 | PML | TPRKB | RASAL3 | GIMAP8 |
| ITPK1 | RALB | UBE2J1 | RBMS3-AS2 | GIPC3 |
| ITPR3 | RAPH1 | UBTD1 | RELB | GNAQ |
| KIF13B | RBMS2 | VAMP5 | RHOB | GPAA1P2 |
| KLF7-IT1 | RDX | VANGL1 | RP11-161M6.2 | GPR17 |
| KLHL2 | RILP | VPS13A | RP11-17G12.3 | GRK2 |
| LDLRAD2 | RNF148 | VPS13C | RP11-288L9.4 | GSDMD |
| LDLRAP1 | RNF38 | WDFY1 | RP11-290L1.3 | H1FX-AS1 |
| LRRC8C | RP1-18D14.7 | | RP11-318C2.1 | HIP1 |

FIG. 11 (cont'd)

| LUZP1 | RP11-138H8.2 | | RP11-350J20.5 | HSPA12B |
|---|---|---|---|---|
| LY96 | RP11-160E2.11 | | RP11-442H21.2 | HYAL1 |
| MANSC1 | RP11-160E2.19 | | RP11-455F5.6 | IFFO1 |
| MAP7D1 | RP11-332M2.1 | | RP11-56N19.5 | IFI44 |
| MAPK12 | RP11-677M14.3 | | RP11-5A19.5 | IKBKB |
| MAPK3 | RP11-691N7.6 | | RP11-638I2.9 | IL27RA |
| MFAP3 | RP11-709A23.2 | | RP11-706P11.2 | INPP5D |
| MGST2 | RP11-73M18.8 | | RP11-73E17.2 | ITM2A |
| MLKL | RP11-744A16.4 | | RP11-75C10.6 | ITPRIP |
| MMRN2 | RP11-823E8.3 | | RP11-79M19.2 | ITSN2 |
| MSRA | RP11-840I19.3 | | RP11-815J21.1 | JUP |
| MTMR12 | RP11-843B15.4 | | RP11-81H3.2 | KANK3 |
| MYCT1 | RP11-902B17.1 | | RP13-20L14.10 | KCNC4 |
| MYO1C | RP3-329E20.2 | | RP3-442L6.4 | KCNJ2 |
| MYO1E | RP4-575N6.5 | | SAMD9L | KDR |
| MYO6 | RP4-671O14.6 | | SEMA4C | KIAA0355 |
| NAP1L4P1 | RP5-1142A6.2 | | SIRT2 | KIAA1462 |
| NCK1 | RP5-1142A6.9 | | SLC12A5 | KIF17 |
| NHSL2 | RP5-997D16.2 | | SLC2A3 | KITLG |
| NLRP1 | RPS27AP12 | | SLC41A1 | KLF13 |
| NPDC1 | SCARF1 | | SMARCA2 | KLF2 |
| NPIPB13 | SELENON | | SOX8 | KSR1 |
| NR5A2 | SENCR | | STAT6 | LA16c-380F5.3 |
| NRN1 | SH3RF3 | | STS | LA16c-390E6.4 |
| NUDT14 | SH3RF3-AS1 | | STXBP5-AS1 | LDB2 |
| ORAI1 | SH3TC1 | | SUSD6 | LGALS9 |
| OSTM1 | SHROOM4 | | TAP1 | LIMS2 |
| PALMD | SLC12A6 | | TAPBPL | LINC00961 |
| PCDH1 | SPDYE3 | | TGFB2-AS1 | LINC01252 |
| PCGF2 | SPTLC2 | | TGFBR3 | LINC01545 |
| PCGF3 | SRGAP2 | | TMEM121 | LMO2 |
| PGS1 | SSH2 | | TMEM35B | LRRC32 |
| PHACTR1 | STXBP1 | | TMOD2 | LTB4R2 |
| PIK3C2A | SYNE3 | | TNRC6C-AS1 | LTF |
| PIK3CG | TAL1 | | TNS1 | LYN |
| PLEC | TCN2 | | TRG-AS1 | LYSMD2 |
| PPP1R18 | TCTEX1D1 | | TRIM34 | MAPK11 |
| PREX1 | TECPR1 | | TRIM56 | MARCKSL1 |

FIG. 11 (cont'd)

| | | | | |
|---|---|---|---|---|
| PREX2 | TLL1 | | TSC22D3 | MARK4 |
| PTK2 | TMEM217 | | TSPAN9 | MBL1P |
| PTPN12 | TMEM44 | | UBA7 | MEF2A |
| PUDP | TNFAIP1 | | UBE2L6 | MEF2C |
| RAB4B | TPST2 | | WIPF1 | MINK1 |
| RAP1A | TREX1 | | | MIRLET7BHG |
| RASIP1 | TRIM25 | | | MLLT6 |
| RGS3 | TRIOBP | | | NEURL1B |
| RLIMP1 | TRPV2 | | | NLRC3 |
| RP1-149A16.12 | TSPAN15 | | | NOTCH1 |
| RP11-1024P17.1 | TTC19 | | | NOTCH4 |
| RP11-1149O23.3 | TTL | | | NOVA2 |
| RP11-1398P2.1 | UHRF1BP1 | | | NRROS |
| RP11-23P13.6 | ULBP2 | | | NUAK1 |
| RP11-25B7.1 | ULBP3 | | | ODF2L |
| RP11-326L2.1 | USP31 | | | OTUD4 |
| RP11-339A11.2 | WARS | | | P2RX7 |
| RP11-3K16.2 | XPR1 | | | PALD1 |
| RP11-411A19.5 | ZCCHC2 | | | PARP14 |
| RP11-44N21.4 | ZDHHC24 | | | PCDH12 |
| RP11-484L8.1 | ZEB1 | | | PCDH17 |
| RP11-544M22.13 | ZEB1-AS1 | | | PDE8A |
| RP11-632F7.3 | ZNF792 | | | PHOSPHO1 |
| RP11-785D18.3 | ZNRF1 | | | PLA2G4C |
| RP11-989E6.13 | | | | PLCG1 |
| RP5-979D14.1 | | | | PLEKHG1 |
| RPL7L1P12 | | | | PLEKHG5 |
| RSU1 | | | | PLK2 |
| SCHIP1 | | | | PLXND1 |
| SDCBP2-AS1 | | | | PPP1R13B |
| SEMA6B | | | | PPP1R9B |
| SERINC3 | | | | PPP2R5B |
| SH3BGRL2 | | | | PRICKLE4 |
| SH3BP4 | | | | PRKCH |
| SH3TC2 | | | | PRKD2 |
| SHANK3 | | | | PRR5L |

FIG. 11 (cont'd)

| | | | | |
|---|---|---|---|---|
| SIGIRR | | | | PRRG3 |
| SLC25A4 | | | | PSEN2 |
| SLC35G2 | | | | PTPRB |
| SNRK | | | | PWWP2B |
| SNX9 | | | | QKI |
| SOX18 | | | | RABEP2 |
| SPTBN5 | | | | RALGDS |
| SRD5A3 | | | | RAMP2 |
| SRGAP2D | | | | RAMP3 |
| SSFA2 | | | | RAPGEF5 |
| STAT5A | | | | RASGRP3 |
| STX6 | | | | RBM44 |
| SYPL1 | | | | RCBTB1 |
| SYT11 | | | | RFLNB |
| TACC1 | | | | RGL2 |
| TBC1D22A | | | | RGS12 |
| TBC1D4 | | | | RHOA-IT1 |
| TBC1D8 | | | | RIN2 |
| TBCD | | | | RNF213 |
| TES | | | | RP1-310O13.7 |
| TGFBR2 | | | | RP11-136K14.1 |
| TM4SF1 | | | | RP11-197N18.7 |
| TMEM132A | | | | RP11-197N18.8 |
| TMEM181 | | | | RP11-314N13.10 |
| TMEM184B | | | | RP11-342D14.1 |
| TMEM50A | | | | RP11-394J1.2 |
| TMEM9B | | | | RP11-405O10.2 |
| TSPAN7 | | | | RP11-413M3.4 |
| TTC13 | | | | RP11-439C15.6 |
| USP35 | | | | RP11-473M20.9 |
| VEGFC | | | | RP11-47I22.1 |
| VPS13D | | | | RP11-47I22.4 |
| WBP1LP2 | | | | RP11-483L5.1 |
| WWC3 | | | | RP11-488C13.6 |
| WWTR1-AS1 | | | | RP11-488L18.10 |
| YEATS2 | | | | RP11-488L18.4 |
| ZDHHC3 | | | | RP11-488L18.8 |
| ZNF101 | | | | RP11-497H17.1 |

FIG. 11 (cont'd)

| ZNF267 | | | | RP11-521B24.4 |
| --- | --- | --- | --- | --- |
| | | | | RP11-52J3.2 |
| | | | | RP11-588H23.3 |
| | | | | RP11-643M14.1 |
| | | | | RP11-709A23.1 |
| | | | | RP11-769O8.1 |
| | | | | RP11-769O8.3 |
| | | | | RP11-789C17.3 |
| | | | | RP11-95F22.1 |
| | | | | RP11-974F13.5 |
| | | | | RP13-1039J1.2 |
| | | | | RP13-104F24.1 |
| | | | | RP13-104F24.2 |
| | | | | RP13-104F24.3 |
| | | | | RP13-554M15.7 |
| | | | | RP3-425P12.1 |
| | | | | RP3-449O17.1 |
| | | | | RP4-737E23.6 |
| | | | | RP4-742J24.2 |
| | | | | RP5-1039K5.12 |
| | | | | RPL34P20 |
| | | | | RPS6KA2 |
| | | | | SDCBP2 |
| | | | | SDPR |
| | | | | SELP |
| | | | | SEMA6A-AS1 |
| | | | | SERF1B |
| | | | | SH2D3C |
| | | | | SH3BP5 |
| | | | | SHC2 |
| | | | | SHE |
| | | | | SHROOM2 |
| | | | | SIPA1 |
| | | | | SLC16A13 |
| | | | | SLC5A4 |
| | | | | SLC9A3R2 |
| | | | | SMAD1 |
| | | | | SPECC1L-ADORA2A |

FIG. 11 (cont'd)

| | | | | |
|---|---|---|---|---|
| | | | | SPTAN1 |
| | | | | SPTBN1 |
| | | | | SRGAP1 |
| | | | | SRGAP2B |
| | | | | SRSF8 |
| | | | | STARD8 |
| | | | | STIM2 |
| | | | | STK10 |
| | | | | STK38L |
| | | | | STOX2 |
| | | | | SULF2 |
| | | | | TAOK2 |
| | | | | TATDN1P1 |
| | | | | TBKBP1 |
| | | | | TCEA2 |
| | | | | TCF15 |
| | | | | TCF4-AS2 |
| | | | | TEK |
| | | | | TIE1 |
| | | | | TJP1 |
| | | | | TMC6 |
| | | | | TMEM127 |
| | | | | TMEM204 |
| | | | | TMEM255B |
| | | | | TMEM37 |
| | | | | TMEM65 |
| | | | | TNFAIP8L1 |
| | | | | TNFRSF25 |
| | | | | ULK4 |
| | | | | USHBP1 |
| | | | | UTRN |
| | | | | VASH1 |
| | | | | VPS37B |
| | | | | VSIG2 |
| | | | | WASF2 |
| | | | | XXcos-LUCA16.1 |
| | | | | ZBTB46 |
| | | | | ZNF467 |

FIG. 11 (cont'd)

|  |  |  |  | ZNF521 |
|---|---|---|---|---|
|  |  |  |  | ZNFX1 |
|  |  |  |  | ZSWIM4 |

| Cluster 5 | Cluster 6 | Cluster 7 | Cluster 8 | Cluster 9 |
|---|---|---|---|---|
| ABLIM1 | ABCC4 | AC002429.5 | ABO | ABHD17B |
| AC006129.2 | ABCG2 | AC004593.3 | AC004381.8 | AC000367.1 |
| AC006129.3 | ADAD2 | AC005042.2 | AC005537.2 | AC006128.2 |
| AC011288.2 | ADAMTS9 | AC005042.4 | AC133680.1 | AC007362.3 |
| AC016757.3 | ADGRG6 | AC006116.20 | ACSM1 | AC007952.4 |
| AC018832.1 | ALPL | AC022154.7 | ACSM3 | AC008277.1 |
| AC078883.4 | ANKRD29 | AC073109.2 | ANTXR2 | AC012066.1 |
| AC098828.2 | AQP7 | AC078883.3 | AR | AC013474.4 |
| ACKR1 | ARL15 | AC078942.1 | ARRDC3-AS1 | AC090505.4 |
| ACSL5 | ATP13A3 | AC092835.2 | ASIC2 | AC092839.3 |
| ADAMTSL2 | ATP6V1C2 | AC092881.1 | BBOX1-AS1 | AMOTL1 |
| AHR | ATP8B3 | AC093110.3 | C1orf162 | ARF4-AS1 |
| ANGEL1 | BDKRB2 | AC147651.4 | CACNA1C-AS4 | C1orf132 |
| ARHGAP25 | C1QA | ACER2 | CD226 | C22orf23 |
| ARHGAP31 | C1QB | ADPRH | CD79B | CA3-AS1 |
| ARHGAP4 | C1QC | ADRA2B | CHRM3 | CEACAM1 |
| ARHGEF1 | C9orf43 | AF127577.13 | CHRM3-AS2 | CETP |
| ARHGEF2 | CA8 | AGTPBP1 | CIITA | CHN1 |
| ARHGEF37 | CD300LG | AKR1E2 | CRHBP | CIDEB |
| ATP2B4 | CD320 | ANKRD45 | CRNDE | CMKLR1 |
| AVPR2 | CFI | AP001596.6 | CSMD1 | CMTM3 |
| B3GNT2 | CHRNE | APOL4 | CYP26B1 | CTC-510F12.3 |
| BAALC-AS1 | CLEC7A | APOLD1 | DENND2C | CTD-2013N17.7 |
| BHLHE40 | COL15A1 | ARGLU1 | DHRS3 | CX3CL1 |
| BHLHE40-AS1 | CRYBG3 | ARHGAP26 | DLGAP1 | CYB5D1 |
| BMF | CTB-134H23.3 | ATG9B | ELAVL2 | DCLK2 |
| BRE | CTD-2193P3.2 | ATP2B1 | F8 | DENND4B |
| BTNL9 | CTD-2357A8.2 | ATP8A1 | FAM84B | DNM3 |
| C10orf11 | CTD-2382E5.6 | ATP8B1 | FMNL2 | DUSP11 |
| C10orf128 | CTNNBIP1 | BAHCC1 | GABRR2 | EHD3 |
| C10orf54 | CXCL12 | BTBD3 | GOLGA8M | ENDOD1 |
| C17orf67 | DIAPH2 | C1RL-AS1 | GS1-174L6.4 | EPHB1 |
| C1orf115 | DIP2B | C1orf61 | GUCY1B2 | ERMP1 |

FIG. 11 (cont'd)

| C1orf54 | EBF3 | C20orf194 | HAPLN1 | FAM102A |
|---|---|---|---|---|
| C2CD4B | EGLN1 | CAMKK1 | HIVEP3 | FAM110A |
| CALML4 | EHHADH | CD34 | HLA-DOA | FAM212A |
| CAMTA1 | ELFN1 | CD74 | IGFBP5 | FAM63B |
| CASP10 | FABP4 | CDA | IL4I1 | FXYD6 |
| CCDC69 | FABP5 | CDK11A | IRX3 | FZD10 |
| CCDC88C | FABP5P3 | CEP68 | IRX5 | GALNT15 |
| CCL15-CCL14 | FABP5P7 | CGNL1 | KCNK6 | GNA14 |
| CD36 | FAM171B | CHN2 | KHDRBS3 | GNG7 |
| CIC | FAM198B | CLSTN3 | KIFC3 | GPM6A |
| CLEC3B | FCER1G | CLVS1 | LINC00305 | GPR1 |
| CLEC9A | FGL2 | CMAHP | LINC00882 | GPR182 |
| CLIC2 | FKBP9P1 | CPLX1 | LINC00970 | GYPC |
| COL4A1 | FMR1-IT1 | CPNE5 | LINC01048 | HS3ST1 |
| COL4A2 | GBP2 | CSGALNACT1 | LRP11 | HSP90AB4P |
| CPAMD8 | GCNT1 | CTA-243E7.4 | MARCKS | IPCEF1 |
| CRYM-AS1 | GIT2 | CTC-548K16.6 | MAST3 | ITGA9 |
| CSF1R | GRIA2 | CTD-2026K11.2 | MEIS2 | JPH1 |
| CSF2RB | H19 | CTD-2233K9.1 | NFAT5 | KCNN2 |
| CTC-270D5.1 | HAGLR | CTD-2363C16.1 | NIPSNAP3B | LA16c-306A4.1 |
| CTC-523E23.4 | HES1 | CTD-2363C16.2 | NPAS3 | LRP5 |
| CTC-526N19.1 | HES5 | CTD-3247H4.2 | OPCML | LRRC55 |
| CTD-2245F17.3 | HLA-DPA1 | CXCL16 | PCED1B | LRRN2 |
| CTD-2369P2.8 | HLA-DPB1 | DAB2IP | PI16 | LTB4R |
| CTD-2562J15.6 | HLA-G | DAPK1-IT1 | PIWIL1 | LYPD5 |
| CTSH | HMCN2 | DCHS1 | PLPP3 | MAN2C1 |
| CYTH1 | HOXD1 | DCST2 | PPP1R9A | MEF2C-AS1 |
| DGKE | IGF2 | DDIT4 | PTPRU | MIR99AHG |
| DHH | IGFBP3 | DDX12P | QRFPR | MTSS1 |
| DLL4 | IGFBP7 | DGKD | RAET1E-AS1 | NCKIPSD |
| DOK4 | IL18R1 | DIP2A | RAET1G | NDUFA9P1 |
| DOPEY2 | JAG1 | DISC1 | RANBP3L | NEAT1 |
| EEPD1 | JAK3 | DLC1 | RAP2A | NET1 |
| EFCAB14 | KCNMB3 | DNAH17 | RARB | NOS2 |
| EGFL8 | KLHL6 | DNASE1L3 | RBP7 | NOSTRIN |
| EHBP1L1 | LACC1 | EBF1 | RIPPLY3 | NPR1 |
| ELMO1 | LAMA5 | EFNB2 | RNF180 | NRP2 |
| F2RL3 | LINC01362 | EFR3B | RP1 | OAS1 |

FIG. 11 (cont'd)

| | | | | |
|---|---|---|---|---|
| FAM26F | LRRC2 | ENTPD1 | RP11-113I24.1 | OAS2 |
| FCHO2 | LTBP1 | ERF | RP11-140H17.2 | OAS3 |
| FOXN2 | MADCAM1 | EXOC3L2 | RP11-159F24.6 | PEAK1 |
| FOXO1 | MALL | FAM13C | RP11-169L17.3 | PIP4K2A |
| GALNT18 | MAN2B1 | FAM167B | RP11-219O3.2 | PITPNM2 |
| GCA | MCTP1 | FLT1 | RP11-334E6.12 | PLAT |
| GGTA1P | MECOM | GABRA2 | RP11-357G3.2 | PM20D1 |
| GJA4 | MEOX1 | GP6 | RP11-477H21.2 | POU6F1 |
| GNGT2 | MERTK | GPRC5B | RP11-557H15.4 | PRCP |
| GPIHBP1 | MS4A6A | GSN | RP11-567J20.2 | PTP4A2P2 |
| GPR34 | MYCNOS | GSN-AS1 | RP11-61L23.2 | PURA |
| GPR85 | MYO10 | GVINP1 | RP11-810H18.1 | RASSF9 |
| GRAMD1A | MYO1B | HERC1 | RP11-81H14.1 | RCSD1 |
| HBEGF | MYRIP | HERC2P3 | RP11-81H14.2 | RNASE1 |
| HCP5 | NFATC2 | HLA-DMA | RP11-876N24.3 | RP11-160E2.16 |
| HEG1 | NINJ2 | HLA-DRA | RP11-876N24.5 | RP11-203J24.8 |
| HEIH | NKX2-3 | HLA-DRB1 | RP11-886P16.6 | RP11-350N15.4 |
| HEY1 | NPIPB11 | HLA-DRB6 | RP4-765C7.2 | RP11-357N13.3 |
| HLA-B | NRP1 | ID1 | RP4-798P15.3 | RP11-360F5.3 |
| HLX | ODF3B | ID3 | RPH3AL | RP11-367B6.2 |
| HMGB3P10 | P2RY2 | IFI44L | RPL21P135 | RP11-395I14.2 |
| ICAM1 | PDE10A | IGF2R | RPL21P23 | RP11-399K21.13 |
| ICAM4 | PLA2G7 | INSR | RYR3 | RP11-44K6.4 |
| IFITM3 | PLCL1 | IQCK | SEMA5B | RP11-506K6.4 |
| IGFBP4 | PMAIP1 | IRF5 | SGCE | RP11-53B2.2 |
| IL10RB-AS1 | PRDM1 | JADE3 | SIGLEC15 | RP11-53B2.3 |
| IL32 | PRDM16 | KCNN3 | SLC14A1 | RP11-53B2.5 |
| IL3RA | PRND | KLHL6-AS1 | SLC2A9 | RP11-541N10.3 |
| IRF2 | PROSER2 | KLK2 | SLCO5A1 | RP11-546O6.4 |
| ITGB4 | PRSS51 | LILRB1 | SNCAIP | RP11-568K15.1 |
| ITM2B | RASA4 | LIMCH1 | SPRY1 | RP11-59C5.3 |
| ITPKB | RASA4B | LINC01537 | TEX35 | RP11-59N23.3 |
| ITPKB-IT1 | RASGRF2 | LIPE | THY1 | RP11-62G11.1 |
| JAG2 | RIPK3 | LPAR6 | TMEM156 | RP11-678G15.1 |
| JAM2 | RND1 | LRCH1 | TNN | RP11-728F11.4 |
| KIAA1671 | RNF219 | LRP6 | TP63 | RP11-737O24.3 |
| KIF26A | RP11-1223D19.3 | MAPKBP1 | TPT1P5 | RP11-739P1.2 |

FIG. 11 (cont'd)

| KLF7 | RP11-162D16.2 | MPPED2 | VNN2 | RP11-768F21.1 |
|---|---|---|---|---|
| KLF8 | RP11-223P11.3 | MTMR9LP | WDR86-AS1 | RP11-894P9.1 |
| LAP3 | RP11-256L6.5 | MX1 | XYLT1 | RP11-916L7.1 |
| LCORL | RP11-307N16.6 | MYCBP2 | | RP11-91J19.3 |
| LCP2 | RP11-314N13.9 | NANOGP4 | | RP3-415N12.1 |
| LIMS4 | RP11-342D11.2 | NCOA7 | | RP4-802A10.1 |
| LIPA | RP11-363E6.3 | NID2 | | S100A4 |
| LRG1 | RP11-404P21.5 | NLRX1 | | SERPINE2 |
| LTA4H | RP11-455O6.2 | NOS3 | | SH3BP5-AS1 |
| LYST | RP11-477G18.2 | NPIPB4 | | SLC27A3 |
| MAGI1 | RP11-489E7.1 | P2RY8 | | SLC37A1 |
| MAGI1-AS1 | RP11-500M8.4 | PDCL3P5 | | SMAD1-AS2 |
| MAMLD1 | RP11-597D13.9 | PDE2A | | SP140L |
| MCF2L | RP11-667F14.1 | PDZD2 | | SP6 |
| MFSD6 | RP11-875O11.3 | PIK3R6 | | SPIN4 |
| MGAT1 | RP11-92C4.6 | PINK1 | | ST3GAL1 |
| MGAT5B | RUNDC3B | PITPNC1 | | ST3GAL5 |
| MMP15 | SCOC-AS1 | PKP4 | | STN1 |
| MOB2 | SELE | PLCB1 | | SVIL |
| MSX1 | SELENOW | PLCL2 | | SYBU |
| MYO5C | SEMA3G | PLVAP | | SYCP2L |
| NDRG1 | SFMBT2 | PODXL | | SYN3 |
| NEDD9 | SIRPB2 | PPARG | | TANC1 |
| NOD1 | SLC12A7 | PPP1R16B | | TCF4-AS1 |
| NOS1 | SLC45A4 | PPT2-EGFL8 | | TCF7L1-IT1 |
| NPIPB3 | SMAD7 | PQLC1 | | TDRP |
| NRARP | SNX3 | PRRG2 | | TEPSIN |
| ODF3L2 | SORBS2 | PTPRG | | TPCN1 |
| OR5AK4P | SPRY4 | PTPRM | | TPM3P7 |
| OSBPL10-AS1 | SRP14 | RAPGEF3 | | TRGV3 |
| OVGP1 | SYNPO | RAPGEF4 | | TRGV4 |
| PDE1C | TACR1 | RARG | | TTC9 |
| PDE6G | TBC1D1 | RASAL2 | | YPEL1 |
| PDGFB | TBC1D9 | RBP5 | | ZBTB39 |
| PIK3C2B | TNNT3 | RCAN2 | | ZDHHC14 |
| PIK3R3 | TNS4 | RFX8 | | ZNF346-IT1 |
| PLCB2 | TSPAN2 | RGS7BP | | ZNF710 |
| PLEKHF2 | YIPF4 | RIMKLB | | |

FIG. 11 (cont'd)

| | | | | |
|---|---|---|---|---|
| PLEKHM1P1 | YPEL2 | RN7SL440P | | |
| PPM1D | ZDHHC9 | RNF138P1 | | |
| PRICKLE3 | | RP11-175K6.1 | | |
| PROS1 | | RP11-212I21.2 | | |
| PRR29-AS1 | | RP11-272L14.2 | | |
| PSMB8-AS1 | | RP11-35G9.5 | | |
| PTP4A3 | | RP11-363E7.4 | | |
| RAPGEF1 | | RP11-389C8.2 | | |
| RAPGEF2 | | RP11-429G19.3 | | |
| RARA-AS1 | | RP11-455F5.4 | | |
| RB1 | | RP11-488C13.5 | | |
| RBKS | | RP11-499F19.3 | | |
| RCAN1 | | RP11-53B2.1 | | |
| RENBP | | RP11-53B2.6 | | |
| RGPD4-AS1 | | RP11-672A2.4 | | |
| RIN3 | | RP11-678G15.2 | | |
| RN7SL344P | | RP11-680B3.2 | | |
| RN7SL862P | | RP11-736K20.5 | | |
| RNF125 | | RP11-973H7.3 | | |
| RNF152 | | RP3-477O4.14 | | |
| RNF19A | | RP4-758J18.10 | | |
| RP11-102N12.3 | | RP5-1057I20.4 | | |
| RP11-169K17.3 | | RPL12P20 | | |
| RP11-177H13.2 | | SATB1 | | |
| RP11-212E4.1 | | SCN4A | | |
| RP11-274A11.4 | | SEMA6C | | |
| RP11-314N13.3 | | SEMA6D | | |
| RP11-318M2.3 | | SESTD1 | | |
| RP11-324O2.3 | | SH2B2 | | |
| RP11-333O1.1 | | SHB | | |
| RP11-344B5.2 | | SIDT1 | | |
| RP11-345K9.2 | | SLC25A16 | | |
| RP11-396F22.1 | | SLC26A6 | | |
| RP11-399K21.12 | | SLC35A1 | | |
| RP11-423G4.10 | | SLC48A1 | | |
| RP11-501O2.3 | | SLC6A6 | | |
| RP11-53I6.2 | | SLC9C1 | | |
| RP11-599J14.2 | | SNX25 | | |

FIG. 11 (cont'd)

| | | | | |
|---|---|---|---|---|
| RP11-676J12.6 | | SOS1-IT1 | | |
| RP11-693N9.2 | | SOX17 | | |
| RP11-809O17.1 | | SSUH2 | | |
| RP1L1 | | ST3GAL6 | | |
| RP5-877J2.1 | | STARD9 | | |
| RPL21P123 | | SV2B | | |
| RPS26P21 | | TARBP1 | | |
| RRN3P3 | | TBXA2R | | |
| RSAD2 | | THSD7A | | |
| RTN4RL1 | | TM4SF18 | | |
| SAMHD1 | | TMCO5B | | |
| SIPA1L2 | | TMEM150C | | |
| SLC16A14 | | TMEM173 | | |
| SLCO2A1 | | TMEM47 | | |
| SLFN5 | | TMEM88 | | |
| SLX1B-SULT1A4 | | TMIGD3 | | |
| SMAD6 | | TNK2 | | |
| SOX13 | | TNRC18P1 | | |
| SOX7 | | TP53I11 | | |
| SPINK5 | | TRAK1 | | |
| SPRY4-IT1 | | TSNAX-DISC1 | | |
| SSH1 | | UACA | | |
| ST8SIA4 | | UNC5B | | |
| STOM | | VWA1 | | |
| STRA6 | | XAF1 | | |
| STX4 | | ZBTB42 | | |
| TAF1C | | ZNF347 | | |
| TAPBP | | ZNF366 | | |
| TCF4 | | ZNF436 | | |
| TCIRG1 | | ZNF503-AS1 | | |
| TDRD10 | | | | |
| TFEB | | | | |
| TMC7 | | | | |
| TMEM100 | | | | |
| TMEM2 | | | | |
| TMEM246 | | | | |
| TNFRSF1B | | | | |
| TNFRSF4 | | | | |

FIG. 11 (cont'd)

| | | | | |
|---|---|---|---|---|
| TRIM16 | | | | |
| TSPAN13 | | | | |
| UPB1 | | | | |
| VIP | | | | |
| YPEL3 | | | | |
| ZC3H12C | | | | |
| ZDHHC20 | | | | |
| ZMIZ1 | | | | |
| ZNF205 | | | | |
| ZNF600 | | | | |

| Cluster 10 | Cluster 11 | Cluster 12 | Cluster 13 | Cluster 14 |
|---|---|---|---|---|
| A2M | ADAMTS13 | ABI3BP | AC009336.19 | ABCA4 |
| ABLIM3 | ADAP2 | ACSS1 | AF131215.2 | AC004019.10 |
| ADAMTS9-AS1 | ADGRL3 | ADGRB3 | AIF1L | AC093690.1 |
| AL163953.3 | AMIGO2 | APOBEC3D | AK4 | AGRN |
| ARHGAP28 | APOD | APOL6 | AKR1C3 | AP1G2 |
| ARRDC3 | ARHGAP45 | ARHGAP6 | AMACR | ARL4C |
| BCHE | BTNL8 | BVES | AMOT | ATF7IP2 |
| BHLHE41 | CD6 | C5orf56 | BHMT2 | BAIAP2L1 |
| CALM1 | CD69 | CACNA1A | CDH24 | BCAM |
| CCDC159 | CDH13 | CALCOCO2 | CHODL | BISPR |
| CFAP45 | CLSTN2 | CASP1 | CLIC5 | BST2 |
| COL11A2 | CTD-3080P12.3 | CCL2 | CRTAC1 | CA2 |
| CP | CTSV | CCL5 | CXADR | CADM4 |
| CPT1C | CXCL1 | CD38 | CXXC5 | CASC15 |
| CTTNBP2 | CYTH4 | CDH18 | CYP1B1 | CECR2 |
| CYP39A1 | DGKI | CH507-513H4.1 | DPP4 | CELSR1 |
| DHX58 | DLL1 | CH507-528H12.1 | ENPP1 | COBLL1 |
| EIF1AX-AS1 | EVI2B | CTD-2269F5.1 | ENPP3 | CSRP2 |
| FAM126A | FGD3 | CTD-2306M5.1 | EPHA4 | CTD-2666L21.1 |
| FAM155A | FHDC1 | CTD-3203P2.3 | FAM221A | CYP4X1 |
| FAM155A-IT1 | FILIP1L | EDIL3 | FAM60A | DNAH1 |
| FBLN2 | FZD8 | FBN1 | FOXC1 | DOC2B |
| FGF12 | GIPC2 | FOLH1 | FOXC2 | DSP |
| FGF18 | GPR160 | GADD45G | GATA3 | EPB41L4A-AS2 |
| FILIP1 | HPR | GNG2 | GGT1 | FAM20A |
| FMO2 | IL7R | HERC5 | GLYCTK | FLJ13224 |

FIG. 11 (cont'd)

| FMO3 | LINC01106 | HLA-K | HIPK2 | GKAP1 |
|---|---|---|---|---|
| FN1 | LLGL2 | IFI35 | HOXD-AS2 | GPRIN3 |
| GABRD | LTB | LAT | HOXD10 | GS1-358P8.4 |
| GFAP | LY6H | LINC00608 | HOXD3 | HOMER1 |
| GJA5 | MYO7B | LINC01123 | HOXD4 | IGSF9B |
| GNAI1 | NLGN4X | LINC01531 | HOXD8 | KBTBD11 |
| HLA-F-AS1 | NR4A2 | MB21D1 | HOXD9 | KIAA1217 |
| ICAM5 | NTN1 | MGC16275 | ISYNA1 | KIAA1522 |
| INMT | PDGFD | MGC32805 | KLHL14 | KL |
| IRAK3 | PIP5K1B | MST1R | LINC00472 | LINC00888 |
| LIFR | PLAU | MT1X | LRRC8D | LINCR-0001 |
| LINC00920 | POF1B | PARP10 | MAP2 | LRTOMT |
| LINC01359 | PTK2B | PARVG | NBEA | MAFB |
| LRRC4 | PTPN7 | PMP22 | NR2F2 | MIR503HG |
| MBNL2 | RAB11FIP1 | RAB8B | PRKAA2 | MTMR8 |
| MIR497HG | RASSF4 | RARRES3 | PRUNE2 | MYCN |
| MMP16 | RGS6 | RHOU | RN7SL650P | NEDD4L |
| MYL4 | RIMS1 | RNASEL | RP11-530C5.1 | NRG3 |
| NFIB | RN7SL182P | RNF165 | SCUBE3 | PDE9A |
| NMRK1 | RP11-284F21.7 | RP11-35612.4 | SEC14L6 | PDK3 |
| NPNT | RP11-299G20.2 | RP11-506N2.1 | SERINC2 | PELI2 |
| OSTF1 | RP11-96O20.4 | RP11-552F3.9 | SH3GLB2 | PLCB4 |
| PCDHGB7 | SERPINB1 | RP11-631N16.4 | SPATA13 | PPM1H |
| PIEZO2 | SLC12A2 | RP11-849N15.3 | SPOCK2 | PPM1L |
| PLSCR4 | SYT13 | RP5-968D22.3 | STXBP2 | PRKCZ |
| PPP1R14A | THSD4 | RXRA | TCAIM | PRTG |
| PZP | TMEM176B | SAMD9 | TMEM178A | RHPN1 |
| RAP2B | TPD52 | SELL | TRPV4 | RN7SL600P |
| RBMS1P1 | TRABD2A | SLC25A45 | XKR6 | RNF144A |
| REPS2 | TRPM2 | SLC31A2 | ZNF124 | RP11-144I2.1 |
| RP11-146G7.2 | VSTM2A | SLCO3A1 | ZNF48 | RP11-154D6.1 |
| RP11-21G15.1 | | SOCS2 | ZNF69 | RP11-276H7.2 |
| RP11-22B23.2 | | SRL | | RP11-849F2.5 |
| RP11-260M19.2 | | STARD5 | | RP11-88I18.2 |
| RP11-380P13.1 | | TCONS_00029157 | | RP11-923I11.6 |
| RP11-506B6.6 | | TNFAIP3 | | RP3-331H24.6 |
| RP11-513M1.1 | | UNC13D | | RP3-512B11.3 |
| RP11-727A23.1 | | ZAP70 | | SNTG2 |

FIG. 11 (cont'd)

| | | | | |
|---|---|---|---|---|
| RP11-856M7.2 | | | | SORT1 |
| RP4-575N6.4 | | | | SOX11 |
| RRN3P2 | | | | SPOCK3 |
| S1PR1 | | | | TET3 |
| SCGB3A1 | | | | TLE4 |
| SERPINH1 | | | | TRIB2 |
| SLC22A23 | | | | TRIM24 |
| SLC9A9 | | | | UGCG |
| SNED1 | | | | UNC5B-AS1 |
| ST8SIA1 | | | | VAV3 |
| SYNC | | | | ZMAT1 |
| TGFB2 | | | | ZNF33A |
| TIAM1 | | | | ZNF35 |
| TLE2 | | | | ZNF620 |
| TMCC2 | | | | |
| TNFAIP2 | | | | |
| TNFRSF19 | | | | |
| TOX2 | | | | |
| TRIM47 | | | | |
| TRIP10 | | | | |
| WNT2 | | | | |
| ZCCHC24 | | | | |
| ZFPM2 | | | | |

| Cluster 15 | Cluster 16 | Cluster 17 | Cluster 18 | Cluster 19 |
|---|---|---|---|---|
| AC007319.1 | AC003075.4 | AATBC | 3-Mar | ABCC1 |
| AC124789.1 | AC073410.1 | ABC7-42404400C24.1 | ABCA3 | AC005786.7 |
| ADAMTS6 | AC108938.5 | AC013264.1 | ABL2 | ACER3 |
| AFMID | ACE | ACKR2 | ABRACL | ADGRL4 |
| AGPAT3 | ADGRL2 | ACKR3 | AC010084.1 | AIDA |
| ANXA3 | ADORA2A | ADGRE5 | ACLY | AP1B1 |
| ARFGEF3 | AGAP1-IT1 | ADM | ACSL4 | APBB2 |
| BCAR3 | AGBL3 | ADRB1 | AGAP2-AS1 | ARFGEF2 |
| BMP2K | AGFG2 | ADRB2 | AHNAK2 | ARPC1B |
| BRI3 | ANKDD1A | ALDH2 | ANGPT2 | ASAP1 |
| C6orf1 | ANO2 | ANKRD20A17P | ANPEP | ASRGL1 |
| CAMKK2 | AP000640.10 | ANKRD36BP2 | ANXA1 | ATF6 |

FIG. 11 (cont'd)

| CARD19 | ARHGAP18 | ANKRD44 | ANXA2 | ATL3 |
|---|---|---|---|---|
| CAV1 | ARHGAP27 | ANKS1A | ANXA2P1 | ATP1B3 |
| CAV2 | ARL4A | ARRB1 | AP2S1 | ATP6V0A2 |
| CCNJ | ARRDC2 | B3GNT7 | APLN | BACE2 |
| CCNJL | ARVCF | BATF2 | ARHGDIB | BAG1 |
| CDC42EP2 | B3GALT4 | C15orf39 | ARHGEF28 | BCAP29 |
| CDC42EP3 | BAALC | C6orf141 | ARPC2 | BCAR1 |
| CDKN1A | BAIAP2 | CA4 | ARPC3 | BCR |
| CH17-296N19.1 | C10orf10 | CADM3 | ARPC5L | C15orf52 |
| CMTM7 | C1QTNF5 | CARD16 | ATG4A | C4orf32 |
| CNTNAP3 | C7orf49 | CARHSP1 | ATP5E | C9orf16 |
| CNTNAP3B | C7orf61 | CASZ1 | ATP6V0E2 | CAPNS1 |
| COL18A1-AS2 | CALCRL | CCDC186 | AVEN | CARD8 |
| CPT1A | CBFA2T3 | CCL21 | BAZ1A | CARD8-AS1 |
| CSF3 | CBX2 | CD14 | BCAP31 | CASP4 |
| CTD-2562J17.6 | CCDC130 | CDC25B | BCL10 | CCNYL1 |
| CTD-2562J17.7 | CCDC141 | CFAP161 | BCL2L1 | CCPG1 |
| CTD-3184A7.4 | CCDC85C | CHL1 | BID | CDK17 |
| CTNNAL1 | CCL14 | CLEC4M | BMP6 | CHST1 |
| DCBLD1 | CCRL2 | CLU | BMX | CHST11 |
| DLGAP1-AS1 | CDCA4P4 | CMTM8 | BOLA2 | CIAPIN1 |
| DLGAP4 | CDKL1 | COLEC10 | BTBD10 | CLIC4 |
| DYRK4 | CFP | CRMP1 | CAPN2 | CNDP2 |
| EDEM3 | CITED4 | CTB-50L17.14 | CARS | COL18A1 |
| EDN1 | CLEC2B | CTB-5E10.3 | CBR3 | COMMD7 |
| EOGT | COL9A3 | CYB5A | CCDC112 | COMT |
| EPHX4 | CORO6 | DKK2 | CD151 | CORO1B |
| ETHE1 | CPE | DMTN | CD59 | CSNK2A2 |
| EWSAT1 | CPEB4 | DOCK5 | CD9 | CSTB |
| EXOC5 | CPTP | DPEP1 | CD99 | CTB-171A8.1 |
| FAM124A | CRACR2B | DTL | CDKN2AIPNL | CTDP1 |
| FAM213B | CTB-31O20.2 | DTX1 | CDYL2 | CTTN |
| FRY | CTB-33G10.6 | ELMOD1 | CFL1 | DNASE1L1 |
| GAS2L3 | CTC-523E23.11 | ELN | CISD1 | DOCK4 |
| GFM1 | CTC-523E23.5 | ENOSF1 | CKLF | DUSP18 |
| GJA1 | CTD-2012K14.2 | FAM84A | CLIC1 | ECE1 |
| GPSM3 | CTD-2135J3.3 | FBXL7 | CNRIP1 | ECSCR |
| HSPB1 | CTD-2135J3.4 | FCGR2A | COL13A1 | EDDM3CP |

FIG. 11 (cont'd)

| IGF2BP2 | CTD-2267D19.3 | FCGR2C | CORO1C | EHD4 |
|---|---|---|---|---|
| IL15RA | CTD-2319I12.4 | FCN3 | COX5A | ELOVL1 |
| IRAK2 | CXCL8 | FENDRR | CPPED1 | ENG |
| ITGA3 | CYB561 | FOXF1 | CRACR2A | EPN1 |
| KCTD17 | CYB5D2 | FOXP1 | CRIM1 | ERAP2 |
| LAPTM5 | CYP46A1 | GCOM1 | CTB-167B5.1 | ESRRA |
| MAPRE2 | DNAJC18 | GJC2 | CYTOR | EXOC2 |
| MGAT5 | DPEP2 | HDAC9 | DBNDD1 | EXOC6 |
| MMRN1 | EFCC1 | HMCN1 | DHCR7 | FAM129B |
| MSRB3 | EGLN3 | HPGD | DNAJC5 | FDPS |
| NADSYN1 | EMP2 | HSD3B7 | DNMBP-AS1 | FEZ2 |
| NTAN1 | EPAS1 | HSPA7 | DUSP23 | FKBP1A |
| P4HA3 | FAM129A | HSPB8 | EPB41L3 | FRMD4A |
| PAK4 | FAM171A2 | IFI27 | EPHA2 | FURIN |
| PDCD6IP | FAM189A1 | IGF1 | ESM1 | FZD4 |
| PDE4B | FAM189A2 | IL12A | ETV5 | GAS2L1 |
| PEAR1 | FAM89A | IL7 | EVA1A | GLRX |
| PEPD | FCHSD2 | IQCA1 | F2R | GMPR |
| PGM2L1 | FIGNL2 | IQSEC3 | FADS3 | GNAI2 |
| PHLDB2 | FNIP2 | ITIH3 | FAM107B | GNG11 |
| PNPLA2 | FOLR2 | KHDRBS2 | FAM213A | GPR4 |
| PON2 | GAS6 | KIAA0040 | FAM43A | GRB10 |
| PPFIBP1 | GHDC | KIAA1324L | FAM49A | GTF3A |
| PRPSAP1 | GIMAP5 | KIAA1456 | FAM50A | HAGLROS |
| PTPRE | GPER1 | KIRREL3-AS2 | FAR2 | HK1 |
| PTRF | GPR146 | KIT | FHL2 | HPCAL1 |
| RAB11A | GPR68 | KLKB1 | FKBP1B | HRCT1 |
| RAB11FIP3 | GRAMD4 | LONRF1 | FKBP5 | ICAM2 |
| RAB11FIP5 | HAPLN3 | LONRF3 | FLNB | IFI16 |
| REEP3 | HDAC4 | LSR | FUT8 | IPO11 |
| RHOJ | HID1 | LXN | FXYD5 | ITGA2 |
| RNF141 | HID1-AS1 | LY6E | GABBR2 | ITGB1 |
| RNF144B | HLA-A | LYPD2 | GALNT7 | JAK1 |
| RP11-206F17.2 | HLA-C | MARVELD2 | GPX1 | KIF1C |
| RP11-392P7.6 | HLA-E | MID2 | HCLS1 | KLHL4 |
| RP11-456P18.2 | HLA-F | MIR181A1HG | HEXB | KTN1 |
| RRAS | HLA-H | MMP17 | HMGA1 | LAMP1 |
| S100A10 | HLA-J | MPP7 | HMGA1P1 | LBR |

FIG. 11 (cont'd)

| | | | | |
|---|---|---|---|---|
| S100A13 | HMBOX1 | MRAP2 | HMGA2 | LINC01197 |
| SCARB1 | HSPA6 | MRAS | HMOX1 | LL0XNC01-116E7.5 |
| SEL1L3 | IGF1R | MRI1 | HRH1 | LPCAT2 |
| SEMA3F | IL33 | MUC19 | HTATIP2 | LRRC8A |
| SERPINB9 | INPP5K | MYO7A | IKBIP | LRRC8B |
| SERTAD4-AS1 | ISLR2 | MYOC | IMPDH1 | LYL1 |
| SFXN3 | IZUMO1 | MYZAP | ISG20 | MACF1 |
| SHC1 | KCNQ1 | NCKAP5 | ITGA10 | MAP1S |
| SIRPA | KCTD12 | NDRG4 | ITGA5 | MAP4K4 |
| SLC35F2 | KDM7A | NFIA-AS2 | KRT18 | MFNG |
| SLCO4A1 | KIAA1257 | NINJ1 | LIPG | MFSD1 |
| SMTN | KLF6 | NKAIN1 | LOXL2 | MICA |
| STARD13 | LA16c-395F10.1 | NLRP3 | LRFN4 | MIER2 |
| STK32B | LAYN | NPR3 | LYPLA1 | MSL3 |
| STX11 | LEPR | NPTN-IT1 | MAP1B | MSN |
| SYNGR2 | LEPROTL1 | NTS | MCAM | MSNP1 |
| TDRD7 | LFNG | NUDT4 | MEDAG | MTHFD2L |
| TDRKH | LHX6 | NUDT4P1 | MET | MTUS1 |
| TFPI | LIMD2 | NUDT4P2 | MGAT4A | MYH9 |
| TGFBRAP1 | LINC01558 | OCLN | MGLL | MYL12A |
| THEM6 | LMCD1 | P2RY1 | MICAL2 | MYO1D |
| TICAM1 | LOXHD1 | PARD6G | MICB | NAA10 |
| TMBIM1 | LRRC36 | PCAT14 | MIEN1 | NBEAL2 |
| TMEM123 | LTC4S | PCLO | MIR222HG | NCKAP1 |
| TMEM62 | LYVE1 | PCSK6 | MIR34A | NDST1 |
| TOR4A | MAP3K6 | PDE3B | MIR4435-2HG | NDUFA8 |
| TRAPPC10 | MFSD4A | PDPN | MMP1 | NECTIN2 |
| TSC22D4 | MMP28 | PIK3IP1 | MPG | NMI |
| TSPAN5 | MPP1 | PKHD1L1 | MRPL17 | NOL4L |
| TSTA3 | MRC1 | PLAG1 | MT2A | NPC2 |
| VAMP3 | MYO18A | PLXNC1 | MVP | NRAS |
| WIPI1 | N4BP3 | PRKCE | NACC1 | NT5E |
| WWTR1 | NEIL1 | PROX1 | NACC2 | NUDT18 |
| ZSCAN16 | NEK3 | PROX1-AS1 | NCEH1 | ORAI2 |
| | NFATC1 | PRX | NES | PAK2 |
| | NLRC5 | QRICH2 | NHSL1 | PARP12 |
| | NPL | RAB3IL1 | NNMT | PARVB |
| | NR1D1 | RAB43 | NOP10 | PDLIM5 |

FIG. 11 (cont'd)

| | | | | |
|---|---|---|---|---|
| | NXN | RAB43P1 | NQO1 | PEF1 |
| | OPHN1 | RASGRP2 | NRGN | PGM2 |
| | OTUD1 | RASGRP4 | OCIAD2 | PIK3CB |
| | PIM3 | REEP1 | OGFRL1 | PISD |
| | PLEKHO2 | RELN | PAWR | PITPNA |
| | PLIN5 | RP1-69D17.3 | PDE7B | PKIG |
| | PPARGC1B | RP1-69D17.4 | PDGFA | PKN1 |
| | PPP2R5A | RP11-1023L17.1 | PFKP | PKN3 |
| | PPP3CA | RP11-10C24.3 | PGAM5 | PLEKHB2 |
| | PRKAR1B | RP11-156K23.3 | PIR | PLOD3 |
| | PTGDS | RP11-160E2.17 | PKIA | PLXNB3 |
| | RALGAPA2 | RP11-299G20.5 | PLAUR | PNPLA6 |
| | RASSF2 | RP11-341G23.2 | PLPP2 | PRKX |
| | RERE | RP11-436K8.1 | PLS3 | PRR29 |
| | RGCC | RP11-449P15.1 | PNP | PTTG1IP |
| | RNASEK-C17orf49 | RP11-6O2.4 | PNPO | PXDC1 |
| | ROBO3 | RP11-87H9.4 | POLR3G | PXN |
| | RP11-120K19.4 | RP5-1101C3.1 | PPP1R13L | PXN-AS1 |
| | RP11-134L10.1 | RPL17P19 | PPP1R14B | RAB12 |
| | RP11-226E21.4 | RSPH4A | PRKCDBP | RAB29 |
| | RP11-27M24.2 | RXFP1 | PROCR | RAB35 |
| | RP11-536K7.3 | S1PR4 | PROSER1 | RCC2 |
| | RP11-575G13.2 | SAMD12 | PRR34-AS1 | RECQL |
| | RP11-670E13.6 | SAMD14 | PRSS23 | REPIN1 |
| | RP11-830F9.7 | SCN3A | PTGFRN | RGS19 |
| | RP11-88I21.2 | SCN3B | PTPN14 | RHOA |
| | RP11-923I11.4 | SEMA7A | RAI14 | RHOC |
| | RP3-395M20.8 | SERTAD4 | RALA | RHOG |
| | RP3-431P23.5 | SGSM1 | RANGAP1 | RNPEPL1 |
| | RPL23AP32 | SLC26A4 | RFK | ROBO4 |
| | RPS6KA1 | SLC2A1 | RGS5 | RP11-117N2.2 |
| | SAMD10 | SLC38A3 | RIN1 | RP11-228B15.4 |
| | SCAMP5 | SLC43A2 | RN7SL667P | RP11-24B13.2 |
| | SCN9A | SLC45A3 | RP11-322E11.5 | RP11-253E3.3 |
| | SEMA6A | SLC6A4 | RP11-322E11.6 | RP11-295G20.2 |
| | SERPINB9P1 | SLCO2B1 | RP11-42O4.2 | RP11-343C2.11 |
| | SGK3 | SMOC1 | RP11-6N17.6 | RP11-381O7.3 |
| | SH3BP2 | SNX30 | RP11-703H8.7 | RP11-479G22.8 |

FIG. 11 (cont'd)

|  | | | | |
|---|---|---|---|---|
|  | SH3PXD2A-AS1 | SPP1 | RPL31P58 | RP11-50C13.1 |
|  | SHROOM1 | SQRDL | RPS6KL1 | RP11-712P20.2 |
|  | SKAP2 | SSTR1 | RTN4 | RP11-87F15.2 |
|  | SLC24A1 | ST8SIA6 | S100A6 | RP5-1085F17.3 |
|  | SLC26A2 | ST8SIA6-AS1 | SCD | RPGR |
|  | SLC44A2 | STAB2 | SCN1B | S100A16 |
|  | SLX1A-SULT1A3 | STAP2 | SCN8A | SASH1 |
|  | SPNS2 | STK4 | SERPINB8 | SEC11C |
|  | STARD3 | STON2 | SERPINE1 | SEC14L1 |
|  | STX3 | SUSD4 | SH3BGRL3 | SH2B3 |
|  | SULT1A3 | SYN2 | SIPA1L3 | SHISA5 |
|  | SULT1A4 | SYNM | SLC16A3 | SHKBP1 |
|  | SULT1C4 | SYT17 | SLC1A4 | SLC25A44 |
|  | SYT15 | TBX1 | SLC27A4 | SLC2A6 |
|  | SYT7 | TBX3 | SLC35E4 | SLC35C1 |
|  | TCP11L2 | TFF3 | SLC38A1 | SLFN11 |
|  | THBD | THEMIS2 | SLC38A7 | SLX1A |
|  | THSD1 | TIMP1 | SLC43A3 | SMIM12 |
|  | THSD7B | TNFRSF11A | SLC4A11 | SNAP23 |
|  | TIMP3 | TRPC6 | SLC52A2 | SNTB2 |
|  | TMEM140 | TSPAN11 | SLC7A1 | SPRYD3 |
|  | TMEM38A | TSPEAR-AS2 | SMURF2 | ST6GALNAC4 |
|  | TNFRSF14 | ULBP1 | SPHK1 | STARD13-AS |
|  | TNFSF10 | VIPR1 | SRGN | SVIP |
|  | TNIP1 | VIPR1-AS1 | SRPX | SWAP70 |
|  | TNXA | VWA2 | STC2 | SYNJ2 |
|  | TNXB | ZBTB16 | STEAP1B | TATDN2P2 |
|  | TRAF3IP2 | ZP2 | STEAP3 | TEAD4 |
|  | TRH | ZSWIM5 | SULT1B1 | TFPT |
|  | TRPM4 |  | TAGLN2 | TGFB1 |
|  | TSPAN18 |  | TAGLN2P1 | TJP2 |
|  | TTN |  | TCHP | TM2D2 |
|  | TUBA4A |  | TFPI2 | TM6SF1 |
|  | VWF |  | TGM2 | TMCC3 |
|  | VWFP1 |  | TIGAR | TMEM109 |
|  | WFS1 |  | TINAGL1 | TMEM8A |
|  | ZDHHC23 |  | TMEM154 | TMSB4X |

FIG. 11 (cont'd)

| | | | | |
|---|---|---|---|---|
| | | | TMEM189-UBE2V1 | TMTC4 |
| | | | TNFAIP8L3 | TNFRSF10A |
| | | | TNFRSF10B | TNFRSF10C |
| | | | TNFSF18 | TNFRSF10D |
| | | | TPM3 | TPM3P9 |
| | | | TRIB3 | TPM4 |
| | | | TSPO | TRAF7 |
| | | | TUBB3 | TSPAN14 |
| | | | TUBB6 | UBASH3B |
| | | | TXNDC9 | UNC13B |
| | | | UAP1L1 | UPP1 |
| | | | UCK2 | VASP |
| | | | USB1 | VAT1 |
| | | | USP18 | VOPP1 |
| | | | VAC14 | WBP2 |
| | | | WDR1 | WSCD1 |
| | | | WDR77 | WWC2 |
| | | | YIF1B | YES1 |
| | | | YWHAB | YRDC |
| | | | ZDHHC12 | YWHAH |
| | | | ZDHHC13 | ZNF195 |

COMPOSITIONS AND METHODS FOR OBTAINING VASCULARIZED HUMAN INTESTINAL ORGANOID TISSUE, AND RELATED USES THEREOF

CROSS-REFERENCE TO RELATED APPLICATION

This application claims priority to U.S. Provisional Patent Application No. 63/030,621 filed May 27, 2020, the contents of which are incorporated by reference in its entirety.

STATEMENT REGARDING FEDERALLY SPONSORED RESEARCH

This invention was made with government support under AI116482, DK103141, HL119215, and HL146162 awarded by the National Institutes of Health. The government has certain rights in the invention.

FIELD OF THE INVENTION

The invention disclosed herein generally relates to methods and systems for converting stem cells into specific tissue(s) or organ(s) through directed differentiation. In particular, the invention disclosed herein relates to methods and systems for promoting vascularized human intestinal organoid tissue having an intestine-specific endothelial cell (EC) transcriptional signature from hindgut spheroid tissue produced in vitro from the described methods.

INTRODUCTION

Pluripotent stem cells (PSCs) have the potential to differentiate into all cell types of the embryo, i.e., cell lineages derived from any of the three embryonic germ layers, including endoderm (interior stomach lining, gastrointestinal tract, the lungs), mesoderm (muscle, bone, blood, urogenital), and ectoderm (epidermal tissues and nervous system).

The culture of embryonic and induced pluripotent stem cells have had an unprecedented impact on the ability to study human diseases and to generate replacement tissues that are therapeutically effective in animal models.

In developmental biology, cellular differentiation is the process by which a less specialized cell becomes a more specialized cell type. Most successful efforts to direct the differentiation of human PSCs into target cell types have been based on studies of embryonic organ development in animal models. Target cell types have potential to enhance our understanding of human disease, may lead to new therapies, and have the potential for use in regenerative medicine. In order to guide stem cell fate in the laboratory, scientists must attempt to recapitulate key developmental processes in a cell culture dish. This is predominantly achieved through modulating signaling pathways using recombinant proteins (i.e. growth factors) and small molecules. This approach has led to the successful generation of PSC-derived liver hepatocytes and pancreatic endocrine cells, which have shown functional potential in animal models of liver disease and diabetes. Similarly, PSCs have been differentiated into more complex, self-organizing, multicellular tissues termed 'organoids' due to their close resemblance to native organ counterparts.

What is needed in the art are methods and systems for accurately controlling the destination of the pluripotent stem cells in order to create the specific type of tissue or organ of desire.

The present invention addresses this need.

SUMMARY OF THE INVENTION

The development of human pluripotent stem cell (hPSC) derived small intestinal organoids (HIOs) (Spence et al., 2010) has led to an improved understanding of human intestinal development and physiology. In order to generate hPSC-derived HIOs, recombinant proteins and/or small molecules are exogenously supplied to cultures in order to mimic the in vivo signaling environment present during development, through a process called directed differentiation (McCracken et al., 2011). Current methods to differentiate HIOs generate both endodermal cells that will give rise to the HIO epithelium as well as a mesoderm population that can give rise to cells of the lamina propria, such as fibroblasts and smooth muscle cells (Finkbeiner et al., 2015a, 2015b; McCracken et al., 2011; Spence et al., 2010; Watson et al., 2014; Wells and Spence, 2014). However, HIOs do not fully recapitulate the complexity of the native human intestine, lacking cellular components including immune cells, enteric neurons (Workman et al., 2016), vasculature and the microbiome (Hill et al., 2017a; Leslie et al., 2014).

Co-culture and transplantation approaches have been developed to increase the complexity of HIOs (Holloway et al., 2019). For example, hPSC-derived enteric neural lineages have been added in vitro and further matured in vivo to establish a functional enteric nervous-like system within HIOs (Schlieve et al., 2017; Workman et al., 2016). Similarly, microinjection of E. coli into the HIO lumen has permitted the study of epithelial response to early gut colonization (Hill et al., 2017a, 2017b). However, vascularization of HIOs has been restricted to in vivo models, whereby HIOs are transplanted into highly vascularized regions of immunocompromised mice (Cortez et al., 2018; Watson et al., 2014). In these environments, HIOs undergo extensive vascularization by the murine host tissue, and increase in complexity to resemble mature intestinal tissue (Finkbeiner et al., 2015b; Watson et al., 2014). However, co-culture approaches or co-differentiating HIOs with a native vasculature prior to in vivo engraftment has not yet been achieved.

Experiments conducted during the course of developing embodiments for the present invention performed single cell RNA sequencing (scRNAseq) at various timepoints across HIO differentiation in vitro and observed a transient population of endothelial-like cells (ECs) present within HIOs early during differentiation; however, these cells are not maintained during prolonged culture under standard growth conditions. This suggested that early during HIO differentiation, cells within the culture are capable of giving rise to EC-like cells. Based on these observations, experiments were conducted wherein it was hypothesized that a modified directed differentiation approach would allow the induction and maintenance of a more robust EC population within HIOs (termed vascularized HIO-vHIO). Such findings demonstrate that modified culture conditions allow a ~13-fold increase in the induction of EC-like cells within HIOs without impacting the other HIO cell populations present (i.e. epithelium, mesenchyme), and support the survival of this population of ECs within HIOs in culture for months.

Since organ-specific morphology in vascular beds has long been appreciated (Aird, 2007), and organ-specific transcriptional signatures and functions have been described in mouse (Ding et al., 2011; Kalucka et al., 2020; Lee et al., 2014; Nolan et al., 2013) and human tissues (Chi et al., 2003; Marcu et al., 2018), experiments were conducted that further sought to determine if HIO ECs were properly patterned by interrogating human fetal intestine, lung, and kidney tissue to identify and validate organ enriched EC gene signatures and individual genes. These data were then used to assess the extent to which HIO ECs resembled human intestinal ECs. After two months of culture, it was observed that relative to human fetal intestine, lung and kidney ECs, HIO ECs were the most transcriptionally similar to the fetal intestine ECs, suggesting that HIOs possess intrinsic properties sufficient to induce ECs to undergo proper organ-specific patterning.

Taken together, these findings show that a native EC population can be co-differentiated within HIO cultures, and that these EC-like cells can be maintained under defined culture conditions for prolonged culture periods. Such results further present human intestinal, lung and kidney EC data sets that can be used as a reference for comparison against in vitro derived organoids and specific cell types found within in vitro organoids. Using transcriptional profiles and a panel of several validated markers, it was concluded that HIO ECs undergo organ-specific patterning in vitro, and most closely resemble an intestinal EC population.

Accordingly, the invention disclosed herein generally relates to methods and systems for converting stem cells into specific tissue(s) or organ(s) through directed differentiation. In particular, the invention disclosed herein relates to methods and systems for promoting and supporting vascular development within human intestinal organoid tissue that possess an intestine-specific EC transcriptional signature from hindgut spheroid tissue produced in vitro from the described methods.

In certain embodiments, the present invention provides methods of inducing formation of vascularized human intestinal organoid tissue having an intestine-specific EC transcriptional signature from human pluripotent stem cells, comprising culturing human pluripotent stem cells with Activin A for a period of approximately three days (e.g., 1 day, 2 days, 3 days, 4 days, 5 days), wherein the culturing results in enrichment of definitive endoderm tissue formation and mesoderm tissue formation;

obtaining definitive endoderm tissue and mesoderm tissue from the human pluripotent stem cells;

culturing the definitive endoderm and mesoderm cells in vitro, wherein the culturing results in differentiation of the definitive endoderm and mesoderm cells into tissue comprising hindgut spheroid tissue, wherein the culturing comprises activating one or more signaling pathways within the definitive endoderm and mesoderm cells, wherein the one or more signaling pathways are selected from the group consisting of the Wnt signaling pathway (e.g., CHIR99021), and/or the FGF signaling pathway (e.g., FGF4), wherein the culturing definitive endoderm cells in vitro occurs for approximately five days (e.g., 3 days, 4 days, 5 days, 6 days, 7 days);

obtaining hindgut spheroid tissue from the cultured definitive endoderm and mesoderm cells;

culturing the obtained hindgut spheroid tissue in vitro, wherein the culturing results in differentiation of the obtained hindgut spheroid tissue into tissue comprising vascularized human intestinal organoid tissue, wherein the culturing comprises a first culturing of the hindgut spheroid tissue, a second culturing of the hindgut spheroid tissue, a third culturing of the hindgut spheroid tissue, and a fourth culturing of the hindgut spheroid tissue;

wherein the first culturing of the hindgut spheroid tissue comprises incubating the hindgut spheroid tissue with ENR media, wherein the ENR media comprises EGF, an inhibitor of the BMP signaling pathway (e.g., Noggin) and a co-activator of the WNT signaling pathway (e.g., R-Spondin2), wherein the first culturing of the hindgut spheroid tissue in vitro occurs for approximately two days (e.g., 0.5 days, 1 day, 1.5 days, 2 days, 3 days), wherein the first culturing of the hindgut spheroid tissue occurs prior to the second culturing of the hindgut spheroid tissue;

wherein the second culturing of the hindgut spheroid tissue comprises incubating the hindgut spheroid tissue with ENR media and vascular endothelial growth factor (VEGF), wherein the ENR media comprises EGF, Noggin and R-Spondin2, wherein the second culturing of the hindgut spheroid tissue in vitro occurs for approximately one day (e.g., 0.25 days, 0.5 day, 0.75 days, 1 days, 1.25 days, 1.5 days), wherein the second culturing of the hindgut spheroid tissue occurs after the first culturing of the hindgut spheroid tissue and before the third culturing of the hindgut spheroid tissue;

wherein the third culturing of the hindgut spheroid comprises incubating the hindgut spheroid tissue with a EGF, BMP4, VEGF and bFGF (FGF2), wherein the third culturing of the hindgut spheroid tissue in vitro occurs for approximately three days (e.g., 1.5 days, 2 days, 2.5 days, 3 days, 3.5 days, 4 days, 5 days), wherein the third culturing of the hindgut spheroid tissue occurs after the second culturing of the hindgut spheroid tissue and before the fourth culturing of the hindgut spheroid tissue;

wherein the fourth culturing of the hindgut spheroid comprises incubating the hindgut spheroid tissue with a receptor tyrosine kinase ligand (e.g., EGF) and VEGF, wherein the fourth culturing of the hindgut spheroid tissue in vitro occurs for at least one day (e.g., 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 30 days, 40 days, 50 days, 75 days, 100 days), wherein the fourth culturing of the hindgut spheroid tissue occurs after the third culturing of the hindgut spheroid tissue; and obtaining vascularized human intestinal organoid tissue having an intestine-specific EC transcriptional signature from the cultured hindgut spheroid tissue.

In certain embodiments, the present invention provides methods of inducing formation of vascularized human intestinal organoid tissue having an intestine-specific EC transcriptional signature from definitive endoderm and mesoderm tissue, comprising culturing definitive endoderm and mesoderm cells in vitro, wherein the culturing results in differentiation of the definitive endoderm and mesoderm cells into tissue comprising hindgut spheroid tissue, wherein the culturing comprises activating one or more signaling pathways within the definitive endoderm and mesoderm cells, wherein the one or more signaling pathways are selected from the group consisting of the Wnt signaling pathway (e.g., CHIR99021), and the FGF signaling pathway (e.g., FGF4), wherein the culturing definitive endoderm cells in vitro occurs for approximately five days (e.g., 3 days, 4 days, 5 days, 6 days, 7 days);

obtaining hindgut spheroid tissue from the cultured definitive endoderm cells;

culturing the obtained hindgut spheroid tissue in vitro, wherein the culturing results in differentiation of the obtained hindgut spheroid tissue into tissue comprising vascularized human intestinal organoid tissue, wherein the culturing comprises a first culturing of the hindgut spheroid tissue, a second culturing of the hindgut spheroid tissue, a third culturing of the hindgut spheroid tissue, and a fourth culturing of the hindgut spheroid tissue;

wherein the first culturing of the hindgut spheroid tissue comprises incubating the hindgut spheroid tissue with ENR media, wherein the ENR media comprises EGF, an inhibitor of the BMP signaling pathway (e.g., Noggin) and a co-activator of the WNT signaling pathway (e.g., R-Spondin2), wherein the first culturing of the hindgut spheroid tissue in vitro occurs for approximately two days (e.g., 0.5 days, 1 day, 1.5 days, 2 days, 3 days), wherein the first culturing of the hindgut spheroid tissue occurs prior to the second culturing of the hindgut spheroid tissue;

wherein the second culturing of the hindgut spheroid tissue comprises incubating the hindgut spheroid tissue with ENR media and vascular endothelial growth factor (VEGF), wherein the ENR media comprises EGF, Noggin and R-Spondin2, wherein the second culturing of the hindgut spheroid tissue in vitro occurs for approximately one day (e.g., 0.25 days, 0.5 day, 0.75 days, 1 days, 1.25 days, 1.5 days), wherein the second culturing of the hindgut spheroid tissue occurs after the first culturing of the hindgut spheroid tissue and before the third culturing of the hindgut spheroid tissue;

wherein the third culturing of the hindgut spheroid comprises incubating the hindgut spheroid tissue with a EGF, BMP4, VEGF and bFGF (FGF2), wherein the third culturing of the hindgut spheroid tissue in vitro occurs for approximately three days (e.g., 1.5 days, 2 days, 2.5 days, 3 days, 3.5 days, 4 days, 5 days), wherein the third culturing of the hindgut spheroid tissue occurs after the second culturing of the hindgut spheroid tissue and before the fourth culturing of the hindgut spheroid tissue;

wherein the fourth culturing of the hindgut spheroid comprises incubating the hindgut spheroid tissue with a receptor tyrosine kinase ligand (e.g., EGF) and VEGF, wherein the fourth culturing of the hindgut spheroid tissue in vitro occurs for at least one day (e.g., 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 30 days, 40 days, 50 days, 75 days, 100 days), wherein the fourth culturing of the hindgut spheroid tissue occurs after the third culturing of the hindgut spheroid tissue; and obtaining vascularized human intestinal organoid tissue having an intestine-specific EC transcriptional signature from the cultured hindgut spheroid tissue.

Such embodiments are not limited to a particular manner of obtaining the definitive endoderm and mesoderm. In some embodiments, the definitive endoderm and mesoderm is obtained through culturing human pluripotent stem cells with Activin A for a period of approximately three days (e.g., 1 day, 2 days, 3 days, 4 days, 5 days).

In certain embodiments, the present invention provides methods of inducing formation of vascularized human intestinal organoid tissue having an intestine-specific EC transcriptional signature from hindgut spheroid tissue, comprising culturing hindgut spheroid tissue in vitro, wherein the culturing results in differentiation of the obtained ventral-anterior foregut spheroid tissue into tissue comprising vascularized human intestinal organoid tissue, wherein the culturing comprises a first culturing of the hindgut spheroid tissue, a second culturing of the hindgut spheroid tissue, a third culturing of the hindgut spheroid tissue, and a fourth culturing of the hindgut spheroid tissue;

wherein the first culturing of the hindgut spheroid tissue comprises incubating the hindgut spheroid tissue with ENR media, wherein the ENR media comprises EGF, an inhibitor of the BMP signaling pathway (e.g., Noggin) and a co-activator of the WNT signaling pathway (e.g., R-Spondin2), wherein the first culturing of the hindgut spheroid tissue in vitro occurs for approximately two days (e.g., 0.5 days, 1 day, 1.5 days, 2 days, 3 days), wherein the first culturing of the hindgut spheroid tissue occurs prior to the second culturing of the hindgut spheroid tissue;

wherein the second culturing of the hindgut spheroid tissue comprises incubating the hindgut spheroid tissue with ENR media and vascular endothelial growth factor (VEGF), wherein the ENR media comprises EGF, Noggin and R-Spondin2, wherein the second culturing of the hindgut spheroid tissue in vitro occurs for approximately one day (e.g., 0.25 days, 0.5 day, 0.75 days, 1 days, 1.25 days, 1.5 days), wherein the second culturing of the hindgut spheroid tissue occurs after the first culturing of the hindgut spheroid tissue and before the third culturing of the hindgut spheroid tissue;

wherein the third culturing of the hindgut spheroid comprises incubating the hindgut spheroid tissue with a EGF, BMP4, VEGF and bFGF (FGF2), wherein the third culturing of the hindgut spheroid tissue in vitro occurs for approximately three days (e.g., 1.5 days, 2 days, 2.5 days, 3 days, 3.5 days, 4 days, 5 days), wherein the third culturing of the hindgut spheroid tissue occurs after the second culturing of the hindgut spheroid tissue and before the fourth culturing of the hindgut spheroid tissue;

wherein the fourth culturing of the hindgut spheroid comprises incubating the hindgut spheroid tissue with a receptor tyrosine kinase ligand (e.g., EGF) and VEGF, wherein the fourth culturing of the hindgut spheroid tissue in vitro occurs for at least one day (e.g., 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 30 days, 40 days, 50 days, 75 days, 100 days), wherein the fourth culturing of the hindgut spheroid tissue occurs after the third culturing of the hindgut spheroid tissue; and obtaining vascularized human intestinal organoid tissue having an intestine-specific EC transcriptional signature from the cultured hindgut spheroid tissue.

Such embodiments are not limited to a particular manner of obtaining the hindgut spheroid tissue. In some embodiments, the hindgut spheroid tissue is obtained through culturing definitive endoderm and mesoderm with CHIR99021 and FGF4 for a period of approximately five days (e.g., 2 days, 3 days, 4 days, 5 days, 6 days, 7 days, 8 days).

Such embodiments are not limited to a particular manner of obtaining the definitive endoderm and mesoderm. In some embodiments, the definitive endoderm and mesoderm is obtained through culturing human pluripotent stem cells with Activin A for a period of approximately three days (e.g., 1 day, 2 days, 3 days, 4 days, 5 days).

In some embodiments, the culturing and obtaining steps are conducted in vitro.

In some embodiments, the obtained vascularized human intestinal organoid tissue comprises a native EC population having an intestine-specific endothelial cell (EC) transcriptional signature.

In certain embodiments, the present invention provides compositions comprising or consisting of vascularized human intestinal organoid tissue having an intestine-specific EC transcriptional signature produced in vitro from the described methods.

In certain embodiments, the present invention provides kits comprising vascularized human intestinal organoid tissue having an intestine-specific EC transcriptional signature produced in vitro from the described methods.

BRIEF DESCRIPTION OF DRAWINGS

FIG. 3A-E: A method to increase differentiation and survival of ECs in HIOs. (A) Schematic of control and vHIO differentiation paradigms. (B) Representative flow cytometric plots of control HIOs and vHIOs for EC markers CD31 and CD144. Flow cytometric analysis of independent batch-matched differentiations of control HIO and vHIOs for presence of CD31+/CD144+ cells after 2-3 weeks in culture (n=3 differentiations in 2 different cell lines), showing an average ~13-fold increase of EC-like cells in the vHIOs. (C) Maximum intensity projection of a wholemount confocal z-series staining for the EC marker CD144 (white) along with ECAD (red) in control HIOs and vHIOs. Scale bar represents 100 μm. (D) UMAP plots demonstrating scRNAseq data from 59d control HIO (grey) and vHIO (pink), and showing feature plots of the EC markers CDH5 and KDR (total of 16,253 cells). Boxed region around the putative EC Cluster 5 (See also FIG. 4). (E) Relative proportion of EC-like cells in control HIOs and vHIO conditions compared to the total number of cells sequenced after 59d in culture.

FIG. 4A-E: Characterization of vHIOs. (A) Summary table for flow cytometric analysis of four independent experiments using two different hPSC lines analyzing CD31+CD144+ and CD31-CD144-cells in matched (i.e. differentiated at the same time) control HIOs and vHIO. (B) Flow cytometric analysis from 59d control HIO and vHIO (WTC11 iPSC line) for EC markers CD31 and CD144. (C) Maximum intensity projections images from z-series imaging (3-5 μm) of immunofluorescent stains carried out on thin paraffin sections for EC markers CD31(red), CD144 (green), ECAD (blue), DAPI (grey) in batch-matched 22d control and vHIOs. Scalebars represent 50 (D) Single cell RNA-seq analysis of 59d WTC11 iPSC-derived control HIOs and vHIO. Inset UMAP plot shows predicted clusters, and the proportion of cells from control HIOs or vHIOs contributing to each cluster is shown (bar plot, table). (E) Dotplot assigning cell classes to control HIOs and vHIOs: intestinal epithelium (CDH1, VIL, CDX2), mesenchymal (VIM, DCN, TCF21, PDGFRa), and endothelial (CDH5, KDR, ESAM, ERG, CD34, and EMCN) markers. Additionally, HIOs were patterned into proximal (duodenal) small intestine as determined by expression of PDX1, and low-to-absent expression of the distal-small intestinal (ileum) and colonic epithelial marker SATB2. Dot size represents the proportion of cells in each cluster expressing a given marker, while color indicates log normalized expression level.

FIG. 5A-E: Defining organ-specific EC genes and gene signatures during human development. (A) Left: Summary of all human lung, intestine, and kidney samples profiled by bulk RNAseq. Closed circles represent samples collected from sorted EC populations, and open circles represent sorted non-EC populations. Samples are colored by organ system: Pink—lung; Blue—intestine; Yellow—kidney. Right: representative flow cytometry plots from each organ. ECs (CD31+CD144+, red) and non-ECs (CD31-CD144-, blue) populations were isolated using FACS. (b) Bulk RNAseq data showing TMM normalized counts for EC genes (CD31, CDH5, KDR) highly enriched in the CD31+ CD144+ samples, and non-EC genes associated with the mesenchyme (PDGFRa), epithelial (EPCAM), and immune (CD45) transcripts enriched in CD31-CD144- samples. (C) Unsupervised hierarchical clustering of all samples profiled in this analysis, along with HUVECs. Each row corresponds to a biological replicate (except HUVEC samples, which represent n=3 technical replicates). (D) Principal component analysis of primary EC populations. (E) Left: K-means gene clustering (k=20, labeled 0-19) identifies organ-specific EC-enriched genes. Each row represents a cohort of genes enriched in one or more samples. Expression of the cohort is shown in each sample as the average normalized gene expression of all genes in that group. Intestinal EC-enriched genes (Cluster 6—blue box), Kidney EC-enriched genes (Cluster 8—yellow box), Lung EC-enriched genes (Cluster 17—pink box). Right: TMM normalized expression of representative organ-specific EC enriched gene candidates in human lung (pink: CA4, ADRB1, VIRP1), intestine (blue: MEOX1, NKX2.3, FABP4), and kidney (yellow: CRHBP, IRX5, IRX3) are shown across all primary samples. Closed circles represent samples collected from sorted EC populations, and open circles represent sorted non-EC populations.

FIG. 6A-H: Validation of organ-specific EC-enriched genes. (A) Top row: UMAP plots for human lung (Pink; n=3; 26,501 cells), intestine (Blue; n=6; 26,010 cells), and kidney (Yellow; n=2; 9,535 cells) showing predicted cell clusters. Bottom row: Feature plots for the EC-specific marker CDH5, highlighting the EC population within each organ. (B) Top row: EC clusters from each organ were computationally extracted, re-clustered, and visualized using UMAP. A total of 1,361 lung ECs, 877 intestinal ECs, and 844 kidney ECs were included in the analysis. Bottom row: Feature plots of the EC marker CDH5 among extracted clusters for each organ. (C-D) C: Feature plots of organ-specific EC genes (identified in FIG. 5) showing expression in scRNA-seq data of the lung-specific EC candidate CA4 in ECs of the lung, intestine and kidney. D: Multiplexed FISH for the pan-EC marker CDH5 (green) and CA4 (pink) in sample matched human fetal tissue (117d). (E-F) E: Feature plot of scRNA-seq data of the intestine-specific EC candidate MEOX1 expression among primary ECs. F: Multiplexed FISH for the pan-EC marker CDH5 (green) and MEOX1 (pink) in sample matched human fetal tissue (117d). (G-H) G: Feature plots of scRNA-seq data of the kidney-specific EC candidate CRHBP expression among primary ECs. H: Multiplexed FISH for the pan-EC marker CDH5 (green) and CRHBP (pink) in sample matched human fetal tissue (120d). Scalebars represent 25 μm.

FIG. 7A-B: Organ-specific EC gene marker expression across organs and major cell classes. (A) Cell type scoring for major cell classes in fetal lung, intestine and kidney data sets, determined as the summed normalized gene expression of canonical markers for endothelial, epithelial, mesenchymal, immune, and neuronal cell populations. B) Feature plots showing expression of organ-specific EC enriched genes across all cells sequenced for each organ. This analysis shows that a given gene may be specific to the ECs of only one organ (i.e. IRX3 in kidney ECs), but that this gene may still be expressed in non-ECs of another organ (i.e. IRX3 is also expressed in lung epithelium).

FIG. 8A-E: Additional scRNAseq and FISH validation of organ-specific EC-enriched signatures. (A) Summary of samples profiled by scRNAseq, along with the total number of cells and the number of ECs profiled for each organ (table). (B) The CDH5+ EC cluster from each organ was extracted and reclustered (FIG. 6A), and feature plots for the lymphatic marker PROX1 is shown. (C) Feature plots showing expression of lung-specific candidates ADRB1 and VIPR1 among primary lung, intestine or kidney ECs with corresponding multiplexed FISH in all three tissues (101d) with these markers (pink), pan-EC marker CDH5 (green), and DAPI (grey). (D) Feature plots depicting expression of intestine-specific candidates NKX2.3 and FABP4 among primary ECs. Corresponding multiplexed FISH for NKX2.3 (pink) and pan-EC marker CDH5 (green), and DAPI (grey) in 117d human. Immunofluorescent staining for FABP4 (pink), CDH5 (pink), and DAPI (grey) in 120d tissue. (E) Feature plots depicting expression of kidney-specific candidates IRX5 and IRX3 among primary ECs with corresponding multiplexed FISH with these markers (pink), pan-EC marker CDH5 (green), and DAPI (grey) in 117d tissue. Note: large pink areas in E correspond to background from red blood cells; specific signal is seen as small bright magenta spots.

FIG. 9A-D: HIO ECs are transcriptionally similar to primary intestinal ECs. (A) The EC cluster from Control HIO and vHIO scRNA-seq data (as shown in FIG. 3) was computationally extracted, re-clustered and visualized using UMAP. (B) Expression of genes identified in gene signatures from primary human fetal ECs (as identified in FIG. 5) were interrogated in ECs from HIOs. A 'gene signature score' was calculated as the average expression of organ-specific EC genes (from primary tissue gene signatures) in the ECs of the HIO (see Methods). The score, corresponding to the average expression of the signature gene sets in each cell, is plotted. (C) Box-and-whiskers plot of individual data points shown in (B) of the organ-specific endothelial cell type scoring. Statistical significance was calculated using a one-way ANOVA (alpha=0.05) followed by a Tukey post-hoc test. The intestine EC score was statistically different than both lung and kidney EC scores (p<0.001). (D) FISH in an vHIO (29d) for the intestine-specific marker NKX2.3 (pink) and the pan-EC marker CDH5 (green), along with protein staining for ECAD (blue), and DAPI (grey). Scalebars represent 50 μm.

FIG. 11: Gene lists pertaining to lung EC signature (lECs), intestine EC signature (iECs), and kidney EC signature (kECs).

DEFINITIONS

Figure 1:
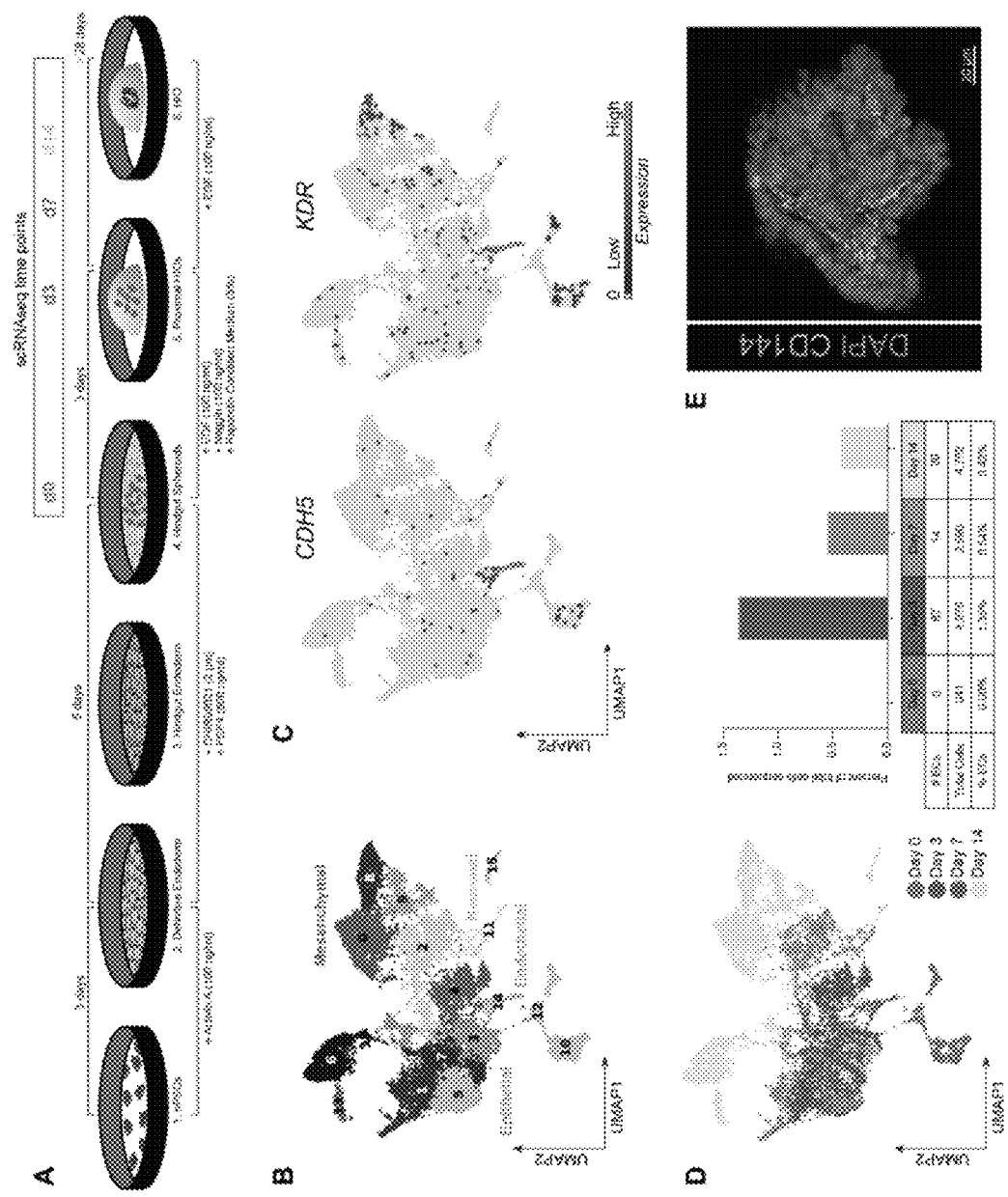
FIG. 1A-E: Identification of an endothelial cell-like population in HIOs. (A) Overview of HIO differentiation protocol highlighting time points when HIOs were collected for single-cell RNA sequencing (scRNAseq). (B) UMAP plot of 13,289 cells from all time points profiled with scRNAseq predicted 15 cell clusters. Cluster identities were assigned based on expression of canonical lineage markers for epithelium, mesenchyme, endothelium, and neurons (see also FIG. 2). (C) Feature plots for endothelial cell (EC) markers CDH5 and KDR showing enrichment in Cluster 14. (D) UMAP plot illustrating the distribution of cells colored by sample (time point) and demonstrating the proportion of Cluster 14 (putative ECs) relative to total cells sequenced per timepoint (bar chart). (E) Wholemount immunofluorescent staining of d4 HIOs with the EC marker CD144 (green) and DAPI (grey). Scalebar represents 20 μm.

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells or obtained through induction of a non-pluripotent cell, such as an adult somatic cell, by forcing the expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

As used herein, the term "organoid" is used to mean a 3-dimensional growth of mammalian cells in culture that retains characteristics of the tissue in vivo, e.g. prolonged tissue expansion with proliferation, multilineage differentiation, recapitulation of cellular and tissue ultrastructure, etc.

DETAILED DESCRIPTION OF THE INVENTION

Human pluripotent stem cell (hPSC)-derived intestinal organoids (HIOs) generated using directed differentiation lack some cellular populations found in the native organ, including vasculature. Using single cell RNA sequencing (scRNAseq), experiments conducted during the course of developing embodiments for the present invention identified a transient population of endothelial cells (ECs) present early in HIO differentiation that are lost over time in culture. Such experiments resulted in the identification of methods to enhance co-differentiation and maintenance of ECs within HIOs (vHIOs). Given that ECs are known to possess organ specific gene expression, morphology and function, experiments further used bulk RNAseq and scRNAseq to interrogate the developing human intestine, lung, and kidney in order to identify organ-enriched EC-gene signatures in these organ systems. By comparing organ-specific gene signatures along with markers validated by fluorescent in situ hybridization to HIO ECs, it was found that HIO ECs grown in vitro share the highest similarity with native intestinal ECs relative to kidney and lung. Together, these data show that HIOs can co-differentiate a native EC population that are properly patterned with an intestine-specific EC transcriptional signature in vitro.

Taken together, such experiments demonstrate an efficient and robust in vitro system to generate vascularized human intestinal organoid tissue having an intestine-specific EC transcriptional signature.

Accordingly, the present invention herein generally relates to methods and systems for converting stem cells into specific tissue(s) or organ(s) through directed differentiation. In particular, the invention disclosed herein relates to methods and systems for promoting vascularized human intestinal organoid tissue having an intestine-specific EC transcriptional signature from hindgut spheroid tissue produced in vitro from the described methods.

In some embodiments, an important step is to obtain stem cells that are pluripotent or can be induced to become pluripotent. In some embodiments, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, three cell lines (H1, H13, and H14) have a normal XY karyotype, and two cell lines (H7 and H9) have a normal XX karyotype.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Indeed, embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14).

In some embodiments, the stem cells are further modified to incorporate additional properties. Exemplary modified cell lines include but not limited to H1 OCT4-EGFP; H9 Cre-LoxP; H9 hNanog-pGZ; H9 hOct4-pGZ; H9 in GFPhES; and H9 Syn-GFP.

More details on embryonic stem cells can be found in, for example, Thomson et al., 1998, Science 282 (5391):1145-1147; Andrews et al., 2005, Biochem Soc Trans 33:1526-1530; Martin 1980, Science 209 (4458):768-776; Evans and Kaufman, 1981, Nature 292(5819): 154-156; Klimanskaya et al., 2005, Lancet 365 (9471): 1636-1641).

Alternative, pluripotent stem cells can be derived from embryonic germ cells (EGCs), which are the cells that give rise to the gametes of organisms that reproduce sexually. EGCs are derived from primordial germ cells found in the gonadal ridge of a late embryo, have many of the properties of embryonic stem cells. The primordial germ cells in an embryo develop into stem cells that in an adult generate the reproductive gametes (sperm or eggs). In mice and humans it is possible to grow embryonic germ cells in tissue culture under appropriate conditions. Both EGCs and ESCs are pluripotent. For purpose of the present invention, the term "ESCs" is used broadly sometimes to encompass EGCs.

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts into pluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

More details on induced pluripotent stem cells can be found in, for example, Kaji et al., 2009, *Nature* 458:771-775; Woltjen et al., 2009, *Nature* 458:766-770; Okita et al., 2008, *Science* 322(5903):949-953; Stadtfeld et al., 2008, *Science* 322(5903):945-949; and Zhou et al., 2009, *Cell Stem Cell* 4(5):381-384.

In some embodiments, examples of iPS cell lines include but not limited to iPS-DF19-9; iPS-DF19-9; iPS-DF4-3; iPS-DF6-9; iPS(Foreskin); iPS(IMR90); and iPS(IMR90).

The present invention provides methods for directing the differentiation of definitive endoderm (DE) into human intestinal organoid tissue having an intestine-specific EC transcriptional signature in vitro.

In some embodiments, PSCs, such as ESCs and iPSCs, undergo directed differentiation in a step-wise manner first into definitive endoderm (DE), then into hindgut spheroid tissue, then into vascularized human intestinal organoid tissue having an intestine-specific EC transcriptional signature.

As such, in some embodiments, methods are provided for the directed differentiation of pluripotent cells (e.g., iPSCs or ESCs) into definitive endoderm, and the obtaining of such definitive endoderm. In some embodiments, methods are provided for the directed differentiation of the obtained definitive endoderm into hindgut spheroid tissue, and obtaining of such hindgut spheroid tissue. In some embodiments, methods are provided for the directed differentiation of the obtained hindgut spheroid tissue into vascularized human intestinal organoid tissue having an intestine-specific EC transcriptional signature.

Such methods are not limited to a particular manner of accomplishing the directed differentiation of PSCs into definitive endoderm. Indeed, any method for producing definitive endoderm from pluripotent cells (e.g., iPSCs or ESCs) is applicable to the methods described herein. In some embodiments, pluripotent cells are derived from a morula. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

In some embodiments, one or more growth factors are used in the differentiation process from pluripotent stem cells to DE cells. The one or more growth factors used in the differentiation process can include growth factors from the TGF-β superfamily. In such embodiments, the one or more growth factors comprise the Nodal/Activin and/or the BMP subgroups of the TGF-β superfamily of growth factors. In some embodiments, the one or more growth factors are selected from the group consisting of Nodal, Activin A, Activin B, BMP4, Wnt3a or combinations of any of these growth factors.

In some embodiments, the embryonic stem cells or germ cells and iPSCs are treated with the one or more growth factors for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours.

In some embodiments, the embryonic stem cells or germ cells and iPSCs are treated with the one or more growth factors at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of the growth factor is maintained at a constant level throughout the treatment. In other embodiments, concentration of the growth factor is varied during the course of the treatment. In some embodiments, the growth factor is suspended in media that include fetal bovine serine (FBS) with varying HyClone concentrations. One of skill in the art would understand that the regimen described herein is applicable to any known growth factors, alone or in combination. When two or more growth factors are used, the concentration of each growth factor may be varied independently.

In some embodiments, definitive endoderm is obtained through culturing human pluripotent stem cells with Activin A for a period of approximately three days (e.g., 1 day, 2 days, 3 days, 4 days, 5 days).

Methods for enriching a cell population with definitive endoderm are also contemplated. In some embodiments, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent.

Additional methods for obtaining or creating DE cells that can be used in the present invention include but are not limited to those described in U.S. Pat. Nos. 7,510,876; 7,326,572; Kubol et al., 2004, Development 131:1651-1662; D'Amour et al., 2005, Nature Biotechnology 23:1534-1541; and Ang et al., 1993, Development 119:1301-1315.

In some embodiments, populations of cells enriched in definitive endoderm cells are used. In some embodiments, the definitive endoderm cells are isolated or substantially purified.

In some embodiments, directed differentiation toward hindgut spheroid tissue, and vascularized human intestinal organoid tissue having an intestine-specific EC transcriptional signature is achieved by selectively activating certain signaling pathways in the iPSCs and/or DE cells. In some embodiments, the activated signaling pathways are those active in intestinal development in a step-wise manner.

In some embodiments, directed differentiation of definitive endoderm into vascularized human intestinal organoid tissue having an intestine-specific EC transcriptional signature is accomplished first through directed differentiation of definitive endoderm into hindgut spheroid tissue, then directed differentiation of the hindgut spheroid tissue into vascularized human intestinal organoid tissue having an intestine-specific EC transcriptional signature.

Such techniques are not limited to a particular manner of inducing formation of hindgut spheroid tissue from definitive endoderm. In some embodiments, inducing formation of hindgut spheroid tissue from definitive endoderm is accomplished through culturing the definitive endoderm cells with CHIR99021 and FGF4 for approximately five days (e.g., 3 days, 4 days, 5 days, 6 days, 7 days).

Such techniques are not limited to a particular manner of inducing formation of vascularized human intestinal organoid tissue having an intestine-specific EC transcriptional signature. In some embodiments, inducing formation of vascularized human intestinal organoid tissue having an intestine-specific EC transcriptional signature from the hindgut spheroid tissue occurs through four successive culturing steps.

In some embodiment, the first culturing of the hindgut spheroid tissue comprises incubating the hindgut spheroid tissue with ENR media, wherein the ENR media comprises EGF, Noggin and R-Spondin2, wherein the first culturing of the hindgut spheroid tissue in vitro occurs for approximately two days (e.g., 0.5 days, 1 day, 1.5 days, 2 days, 3 days).

In some embodiments, the second culturing of the hindgut spheroid tissue comprises incubating the hindgut spheroid tissue with ENR media and vascular endothelial growth factor (VEGF), wherein the ENR media comprises EGF, Noggin and R-Spondin2, wherein the second culturing of the hindgut spheroid tissue in vitro occurs for approximately one day (e.g., 0.25 days, 0.5 day, 0.75 days, 1 days, 1.25 days, 1.5 days).

In some embodiments, the third culturing of the hindgut spheroid comprises incubating the hindgut spheroid tissue with EGF, BMP4 and bFGF, wherein the third culturing of the hindgut spheroid tissue in vitro occurs for approximately three days (e.g., 1.5 days, 2 days, 2.5 days, 3 days, 3.5 days, 4 days, 5 days).

In some embodiments, the fourth culturing of the hindgut spheroid comprises incubating the hindgut spheroid tissue with EGF and VEGF, wherein the fourth culturing of the hindgut spheroid tissue in vitro occurs for at least one day (e.g., 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 30 days, 40 days, 50 days, 75 days, 100 days).

In some embodiments, vascularized human intestinal organoid tissue having an intestine-specific EC transcriptional signature produced in vitro from the described methods can be used to screen drugs for intestinal tissue uptake and mechanisms of transport. For example, this can be done in a high throughput manner to screen for the most readily absorbed drugs, and can augment Phase 1 clinical trials that are done to study drug intestinal tissue uptake and intestinal tissue toxicity. This includes pericellular and intracellular transport mechanisms of small molecules, peptides, metabolites, salts.

In some embodiments, vascularized human intestinal organoid tissue having an intestine-specific EC transcriptional signature produced in vitro from the described methods can be used to identify the molecular basis of normal human intestinal development.

In some embodiments, vascularized human intestinal organoid tissue having an intestine-specific EC transcriptional signature produced in vitro from the described methods can be used to identify the molecular basis of congenital defects affecting human intestinal development.

In some embodiments, vascularized human intestinal organoid tissue having an intestine-specific EC transcriptional signature produced in vitro from the described methods can be used to correct intestinal related congenital defects caused by genetic mutations. In particular, mutation affecting human intestinal development can be corrected using iPSC technology and genetically normal vascularized human intestinal organoid tissue having an intestine-specific EC transcriptional signature produced in vitro from the described methods. In some embodiments, vascularized human intestinal organoid tissue having an intestine-specific EC transcriptional signature produced in vitro from the described methods can be used to generate replacement tissue.

In some embodiments, vascularized human intestinal organoid tissue having an intestine-specific EC transcriptional signature produced in vitro from the described methods can be used to generate replacement intestinal tissue for intestine related disorders.

In some embodiments, a diagnostic kit or package is developed to include vascularized human intestinal organoid tissue having an intestine-specific EC transcriptional signature produced in vitro from the described methods and based on one or more of the aforementioned utilities.

The invention provides a composition comprising a culture medium according to the invention and stem cells. The invention also provides a composition comprising a culture medium according to the invention and organoids. Furthermore, the invention provides a composition comprising a culture medium according to the invention. Furthermore, the invention provides a composition comprising a culture medium according to the invention and an extracellular matrix.

The invention also provides a composition comprising a culture medium of the invention, an extracellular matrix and human pluripotent stem cells. The invention also provides a composition comprising a culture medium of the invention, an extracellular matrix and vascularized human intestinal organoid tissue having an intestine-specific EC transcriptional signature of the invention.

The invention also provides a hermetically-sealed vessel containing a culture medium of the invention. Hermetically-sealed vessels may be preferred for transport or storage of the culture media or culture media supplements disclosed herein, to prevent contamination. The vessel may be any suitable vessel, such as a flask, a plate, a bottle, a jar, a vial or a bag.

The invention provides the use of vascularized human intestinal organoid tissue having an intestine-specific EC transcriptional signature of the invention or cells derived thereof in drug screening, (drug) target validation, (drug) target discovery, toxicology and toxicology screens, personalized medicine, regenerative medicine and/or as ex vivo cell/organ models, such as disease models.

Cells and vascularized human intestinal organoid tissue having an intestine-specific EC transcriptional signature cultured according to the media and methods of the invention are thought to faithfully represent the in vivo situation. This is true both for expanded populations of cells and organoids grown from normal tissue and for expanded populations of cells and organoids grown from diseased tissue. Therefore, as well as providing normal ex vivo cell/organ models, the organoids of the invention can be used as ex vivo disease models.

Organoids of the invention (e.g., vascularized human intestinal organoid tissue having an intestine-specific EC transcriptional signature) can also be used for culturing of a pathogen and thus can be used as ex vivo infection models. Examples of pathogens that may be cultured using an organoid of the invention include viruses, bacteria, prions or fungi that cause disease in its animal host. Thus an organoid of the invention can be used as a disease model that represents an infected state. In some embodiments of the invention, the organoids can be used in vaccine development and/or production.

Diseases that can be studied by the organoids of the invention (e.g., vascularized human intestinal organoid tissue having an intestine-specific EC transcriptional signature) thus include genetic diseases, metabolic diseases, pathogenic diseases, inflammatory diseases etc of the intestine and/or related to intestinal development.

The organoids of the invention (e.g., vascularized human intestinal organoid tissue having an intestine-specific EC transcriptional signature) can be frozen and thawed and put into culture without losing their genetic integrity or phenotypic characteristics and without loss of proliferative capacity. Thus the organoids can be easily stored and transported. Thus in some embodiments, the invention provides a frozen organoid.

For these reason the organoids or expanded populations of cells of the invention can be a tool for drug screening, target validation, target discovery, toxicology and toxicology screens and personalized medicine.

Accordingly, in a further aspect, the invention provides the use of an organoid or cell derived from said organoid according to the invention in a drug discovery screen, toxicity assay or in medicine, such as regenerative medicine. For example, the vascularized human intestinal organoid tissue having an intestine-specific EC transcriptional signature may be used in a drug discovery screen, toxicity assay or in medicine, such as regenerative medicine.

For preferably high-throughput purposes, said organoids of the invention (e.g., vascularized human intestinal organoid tissue having an intestine-specific EC transcriptional signature) are cultured in multiwell plates such as, for example, 96 well plates or 384 well plates. Libraries of molecules are used to identify a molecule that affects said organoids. Preferred libraries comprise antibody fragment libraries, peptide phage display libraries, peptide libraries, lipid libraries, synthetic compound libraries or natural compound libraries. Furthermore, genetic libraries can be used that induce or repress the expression of one of more genes in the progeny of the stem cells. These genetic libraries comprise cDNA libraries, antisense libraries, and siRNA or other non-coding RNA libraries. The cells are preferably exposed to multiple concentrations of a test agent for a certain period of time. At the end of the exposure period, the cultures are evaluated. The term "affecting" is used to cover any change in a cell, including, but not limited to, a reduction in, or loss of, proliferation, a morphological change, and cell death.

In some embodiments, the organoids of the invention (e.g., vascularized human intestinal organoid tissue having an intestine-specific EC transcriptional signature) can be used to test libraries of chemicals, antibodies, natural product (plant extracts), etc for suitability for use as drugs, cosmetics and/or preventative medicines.

The invention provides the use of vascularized human intestinal organoid tissue having an intestine-specific EC transcriptional signature in regenerative medicine and/or transplantation. The invention also provides methods of treatment wherein the method comprises transplanting an organoid into an animal or human.

Vascularized human intestinal organoid tissue having an intestine-specific EC transcriptional signature are useful in regenerative medicine, for example in treatment of post-radiation and/or post-surgery repair of the intestinal epithelium, in the repair of the intestinal epithelium in patients suffering from inflammatory bowel disease such as Crohn's disease and ulcerative colitis, and in the repair of the intestinal epithelium in patients suffering from short bowel syndrome. Further use is present in the repair of the intestinal epithelium in patients with hereditary diseases of the small intestine/colon.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1. hPSC-Derived Human Intestinal Organoids (HIOs) Develop a Transient Population of Endothelial Cells (ECs)

Human intestinal organoids (HIOs) have been almost exclusively characterized following growth for several weeks in culture (Capeling et al., 2019; Finkbeiner et al., 2015b; Spence et al., 2010; Tsai et al., 2017). Through these analyses, various intestinal epithelial and mesenchymal populations have been identified. Initial observations suggested that HIOs lacked an EC population (Spence et al., 2010); however, a thorough investigation of cellular heterogeneity within HIOs across time has not been carried out.

Figure 2:
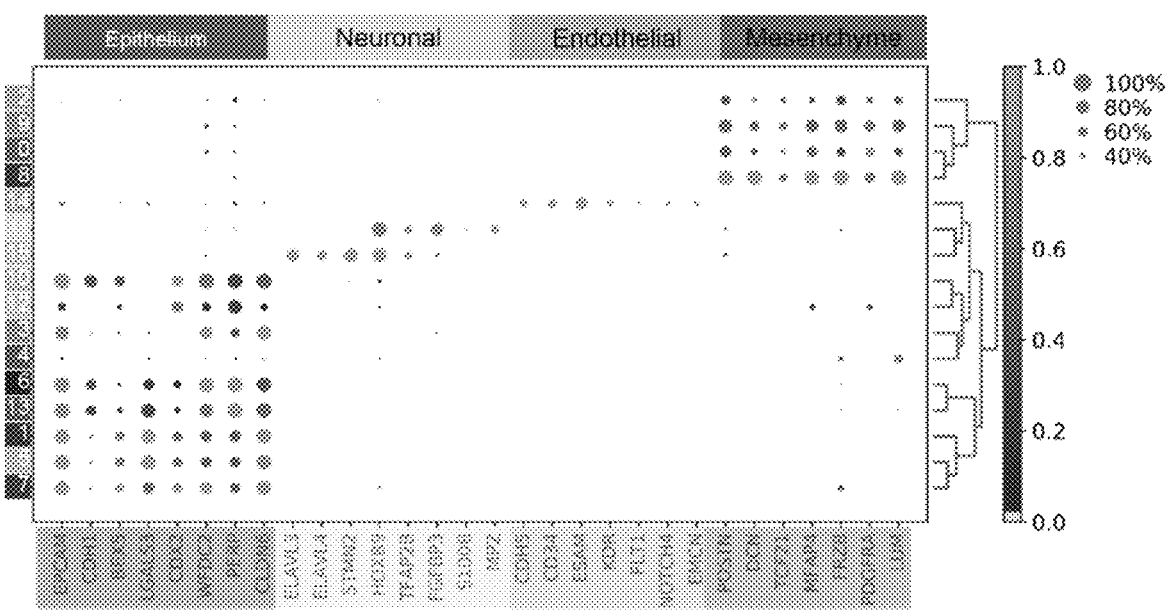
FIG. 2: Cell type classification of HIOs. Dotplot of genes associated with major cell classes: epithelial, mesenchymal, endothelial, neuronal genes. Dot size represents the proportion of cells in each cluster expressing a given marker, while color indicates log normalized expression level. Clusters are colored by class assignment: Blue—epithelium; Yellow—neuronal; Red—endothelial; Green—mesenchyme.

In order to gain insights into cellular heterogeneity during HIO growth and differentiation, a single cell RNA sequencing (scRNAseq) time course analysis was performed. Analysis was carried out on HIO samples following hindgut patterning and specification into a CDX2+ intestinal lineage, the time when monolayer cultures give rise to 3-dimensional (3D) spheroids (herein referred to as 'day 0'), and several time points after embedding spheroids in Matrigel for growth and expansion into HIOs (days 3, 7, and 14) (FIG. 1A). A total of 13,289 cells from these four time-points (days 0, 3, 7, 14) were included in the computational analysis and the data were visualized using UMAP dimensional reduction (Becht et al., 2019; Wolf et al., 2018) (FIG. 1B). Cell classifications were carried out using canonical markers for lineages (i.e. epithelial, mesenchymal, endothelial) (FIG. 1B, 2). Expected epithelial and mesenchymal cell lineages within HIOs were identified; however, cell clusters possessing endothelial (cluster 14) and neuronal (clusters 11,15) gene signatures were also identified (FIG. 2). The endothelial cluster was defined by a gene set expected to be present in ECs, including CDH5, KDR, FLT1, and ESAM (FIG. 1C, 2). The time course revealed that the EC-like population in cluster 14 was transient, with the highest proportion of EC-like cells on day 3 of culture (1.35% of all day 3 cells), after which EC prevalence progressively decline to 0.54% on day 7 and 0.42% on day 14 (FIG. 1D). Wholemount staining of day 3 HIOs with the EC lineage markers CD144 and CD31 confirmed the existence of an EC-like population early during HIO growth (FIG. 1E). Together, these data suggest that HIO differentiation cultures are capable of spontaneously giving rise to EC-like cells that diminish over time.

Example II. Developing a Method to Induce and Maintain ECs within HIOs

The progressive reduction of EC-like cells over time suggested that standard HIO culture conditions are not optimal for supporting robust long-term EC survival. Therefore, experiments were conducted that sought to define new culture conditions that would increase the survival of the co-differentiated EC population within HIOs. It was hypothesized that addition of growth factors important for vascular induction and maintenance would improve EC differentiation and maintenance within HIOs, including VEGF, bFGF, and BMP4 (Orlova et al., 2014; Patsch et al., 2015; Sriram et al., 2015; Wimmer et al., 2019). On day 2 of HIO culture, VEGF was added into the HIO media (EGF/NOG/RSPO—'ENR') in order to promote survival of any endogenously arising ECs (FIG. 3A). Although BMP has been used in multiple culture settings to induce ECs from hPSCs, NOG was included for the first 3 days of HIO growth because modulation of BMP signaling is also responsible for proximal-distal patterning in HIOs (Múnera et al., 2017). Antagonism via NOG is required for patterning HIOs into proximal duodenum-like tissue, while adding BMP ligands to the media in early cultures instructs a colonic fate in HIOs (Múnera et al., 2017). After 3 days of HIO patterning into an proximal/duodenal identity, HIOs were maintained without RSPO or NOG from day 3 onwards, as EGF is sufficient to support HIO growth following proximal-distal patterning (Múnera et al., 2017). Subsequently, in order to induce additional ECs, HIOs were treated for three days with VEGF, FGF2 (bFGF) and BMP4 (herein referred to as the vHIO protocol; FIG. 3A), which have been shown to enrich ECs in hPSC-derived mesenchyme (Orlova et al., 2014; Patsch et al., 2015; Sriram et al., 2015; Wimmer et al., 2019). HIOs generated with the vHIO protocol were maintained in media supplemented with EGF and VEGF for up to two months prior to analysis, while controls were maintained in media containing EGF only (FIG. 3A). To assess the proportion of EC-like cells in HIOs following induction, flow cytometric analysis of CD31+/CD144+ cells was used to compare control HIOs and vHIOs. After several weeks in culture, ECs constituted an average of 0.20% in control HIOs, whereas vHIOs possessed 2.62% CD31+/CD144+a ~13-fold increase compared to control culture conditions (FIG. 3B). Identification of CD31+/CD144+ cells within vHIOs using immunofluorescence confirmed EC enrichment as double-positive cells were abundant and were observed within HIO mesenchyme (FIG. 2C, 4C). ECs persisted for two months in culture, the longest time point examined (FIG. 2D,E, 4E).

To further support our flow cytometric and immunohistochemical data showing EC-enrichment, and to assess the effect of the vHIO protocol on overall HIO development and cellular makeup, scRNAseq was performed on control and vHIO tissue after two months in culture. A total of 16,253 cells (8,973 control and 7,280 vHIO) were analyzed and the data were visualized using UMAP dimensional reduction (FIG. 3D-E). Epithelial lineages (clusters 2 and 3), mesenchymal lineages (clusters 0,1, and 4), and endothelial lineages (cluster 5) were classified based on expression of canonical makers (FIGS. 3D and 4D-E). Quantification of the contribution of control and vHIO cells to each cluster was performed (FIG. 4D). ECs were enriched in the vHIO condition compared to control, comprising 2.03% of all cells sequenced in the vHIO condition, a 3.5-fold increase over control HIOs (FIG. 3E). More generally, this scRNAseq analysis demonstrated that all of the cell populations visualized by UMAP have contributions from both HIOs and vHIOs, showing that the vHIO differentiation paradigm does not induce cell population gain or loss (FIG. 4D), and reinforces data showing that this method enriches EC-like cells (FIG. 4D).

Example III. Defining a Human Intestinal EC Transcriptional Signature

Organ-specific properties including morphology, transcriptional signatures, and function have been described in mouse and human organs (Daniel et al., 2018; Ding et al., 2010, 2011; Lee et al., 2014; Marcu et al., 2018; Nolan et al., 2013); however, experiments were conducted that sought to better understand intestine-specific EC properties in order to compare in vivo ECs with induced ECs found within HIOs. To identify intestine-specific EC transcriptional signatures, we performed bulk RNA sequencing (RNAseq) on FACS-isolated EC (CD31$^+$CD144$^+$) and non-EC (CD31$^-$CD144$^-$) populations from human fetal intestine, lung, and kidney spanning 13-20 weeks of development (FIG. 5A). Bulk RNAseq data demonstrated that canonical EC markers (CD31, CD144, KDR) were enriched in the CD31+/CD144+ isolated populations (FIG. 5B). Additionally, the EC samples had low-to-no expression of mesenchyme genes (i.e. PDGFRa), hematopoietic genes (i.e. CD45), and epithelial genes (i.e EPCAM), which were expressed in the double negative (CD31$^-$CD144$^-$) population as expected (FIG. 5B). Unsupervised hierarchical clustering of all samples revealed that primary ECs from different human organs (intestine, lung, kidney) formed their own clade, and the CD31–/CD144–'non-ECs' formed another clade. Notably, biological replicates of the same organ were closest in similarity compared to EC samples isolated from the other organs, to non-ECs, and to human umbilical vein endothelial cells (HUVECs), suggesting that there are organ-specific transcriptional profiles among human fetal ECs (FIG. 5C). Principal component analysis of the primary ECs produced organ-specific clustering, further supporting the existence of organ-specific transcriptional differences across human fetal intestine, lung, and kidney ECs (FIG. 5D). K-means (k=20) gene clustering was used to identify genes enriched within the ECs of a single organ. At this resolution, pan-EC enriched gene clusters (0, 1, 2, 3, 4) as well as organ-specific EC-enriched gene clusters (6, 8, 17) were identified (FIG. 5E). Over 100 organ-specific EC-enriched genes were computationally identified for all 3 organs. These gene lists are herein referred to as the lung EC signature (IECs), intestine EC signature (iECs), and kidney EC signature (kECs) (FIG. 11).

Validation of the organ-specific EC genes and gene signatures identified by bulk RNAseq (FIG. 3) was carried out using both scRNAseq and fluorescent in situ hybridization (FISH) (FIG. 6). Experiments were conducted that used scRNAseq to profile human fetal lung (Miller et al., 2020), intestine (Czerwinski et al., 2020), and kidney across 7 specimens spanning 13.5-19 weeks of gestation (FIG. 7A). In total, our analyses included 62,046 cells across these three organs (FIGS. 5A and 8A). An EC cluster was identified for each organ using cell type scoring (see Methods), which leverages gene cohorts canonically associated with different cell classes (i.e. epithelium, mesenchyme, endothelium, immune, neuronal) (Miller et al., 2020) (FIG. 6A, 7). Based on this analysis, EC clusters were computationally extracted and re-clustered; the EC clusters collectively contained 3,082 cells and are comprised of 1,361 lung ECs, 877 intestine ECs, and 884 kidney ECs (FIG. 6B, FIG. 8A). This analysis also revealed EC heterogeneity in the form of sub-clusters, including a lymphatic EC cluster apparent in the lung (cluster 5) and intestine (cluster 2) as defined by PROX1 expression (De Val and Black, 2009; Wigle and Oliver, 1999; Wigle et al., 2002) (FIG. 8B). Organ-specific EC genes identified in bulk RNAseq data were validated in scRNAseq data (FIGS. 6C, E, and G, FIG. 8C-E). The single cell data showed that organ-specific EC genes are expressed by vascular ECs in a manner expected based on the bulk sequencing data. Notably, despite being enriched in ECs in an organ-specific manner, markers were also expressed by non-EC lineages among the organs profiled (FIG. 7). Collectively, these data showed that a given gene is enriched in ECs of a single organ relative to the other organs, but that expression may not be exclusive to ECs (FIG. 7). Experiments were conducted that also used multiplexed FISH to validate a cohort of organ-specific EC genes. Sample matched human fetal lung, intestine, and kidney were stained for the panel of organ-specific EC markers alongside the pan-EC marker CDH5 (FIGS. 6D, F, H and 8). Three EC-specific organ-enriched genes were selected from lung (CA4, ADRB1, VIRP1), intestine (MEOX1, NKX2.3, FABP4) and kidney (CRHBP, IRX3, IRX5) for validation by multiplexed FISH (FIG. 5E, FIG. 6). This approach confirmed data obtained in bulk and single cell RNA sequencing. Through this validation effort, a panel of 9 organ-specific EC enriched markers across human fetal lung, intestine, and kidney can be used in combination with computational analysis to assess the patterning of ECs co-differentiated within HIOs.

Figure 10:
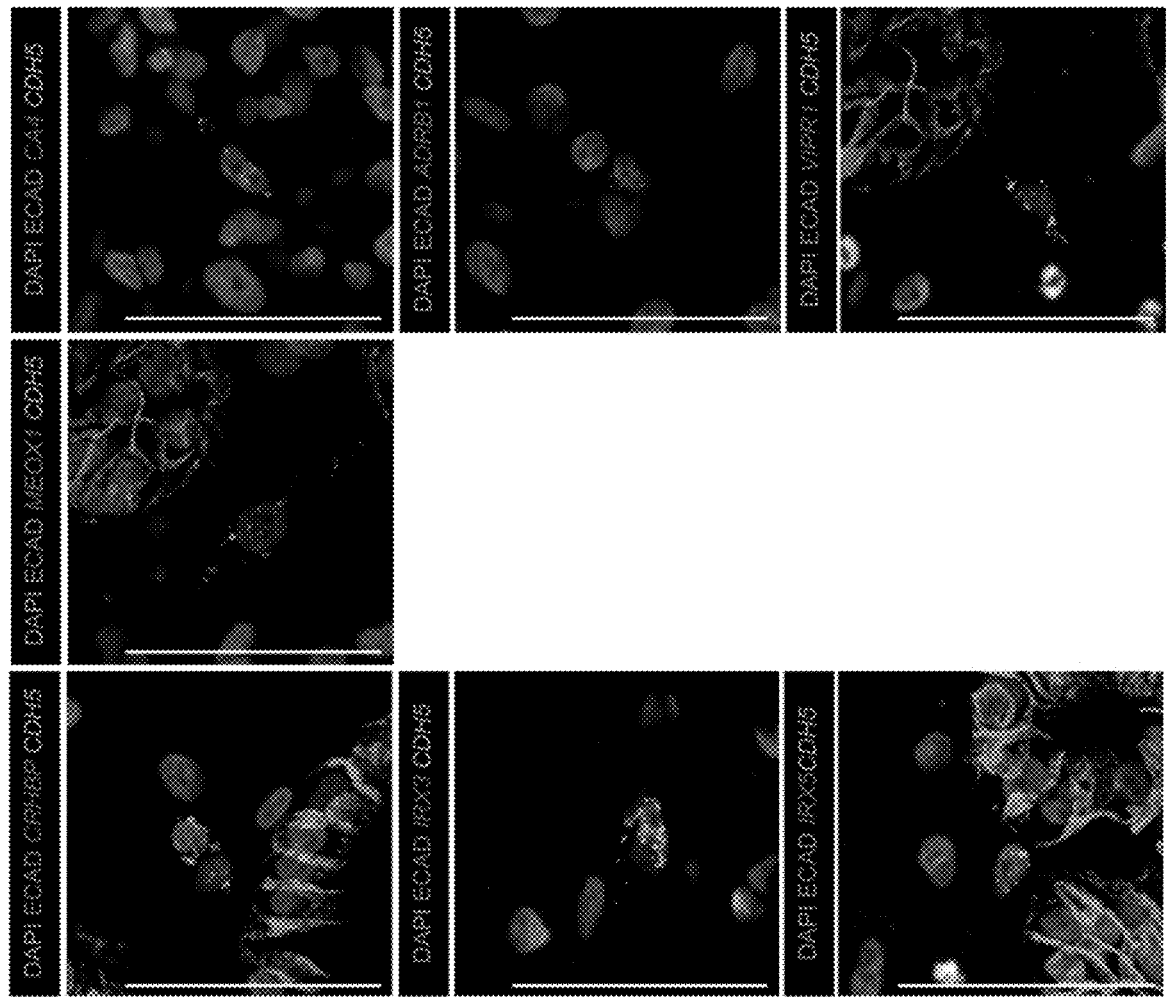
FIG. 10: Organ-specific EC gene marker expression in vHIOs after 29d in culture. Top row: FISH of the lung EC markers CA4, ADRB1, VIPR1 (pink) co-stained with the pan-EC marker CDH5 (green), protein staining for ECAD (blue), and DAPI (grey) in 29d vHIOs. Middle row: FISH of the intestine EC marker MEOX1 (pink) co-stained with the pan-EC marker CDH5 (green), protein staining for ECAD (blue), and DAPI (grey) in 29d vHIOs. Bottom row: FISH of the kidney EC markers CRHBP, IRX3, IRX5 (pink) co-stained with the pan-EC marker CDH5 (green), protein staining for ECAD (blue), and DAPI (grey) in 29d vHIOs. These data show that all markers were absent from 29d vHIOs. Scalebars represent 50 μm.

Example IV. HIO ECs Share the Highest Transcriptional Similarity with Fetal Intestinal EC Given the unique organ-specific gene expression by ECs in vivo during human development, experiments were conducted that wanted to assess the extent of organ-specific patterning of the ECs induced within HIOs. The EC cluster from scRNAseq (cluster 5, FIG. 4D) of 59d control and HIO ECs was computationally extracted, reclustered and visualized using UMAP (FIG. 9A). To determine how similar gene expression of HIO ECs was to native organ gene signatures, organ-specific EC-enriched gene signatures (lECs, iECs, and kECs) identified in bulk RNAseq (FIG. 5) served as the foundation for organ-specific cell type scoring analysis. The HIO ECs were analyzed for expressed genes found in lECs, iECS, and kECs. As such, the expression of 137 lECs, 89 iECs, and 50 kECs genes was determined in HIO ECs, and the average expression for each organ-signature was determined for HIO ECs. Based on this analysis ECs co-differentiated within HIOs had the highest average expression of the intestinal EC signature relative to lung and kidney ECs (FIG. 9B,C). FISH analysis of 29-day vHIOs confirmed expression of the intestine-specific marker, NKX2.3 by HIO ECs (FIG. 9D); and a lack of detectable expression of markers validated for the lung or kidney (FIG. 10). Notably, the intestinal EC marker MEOX1 was not detectable by FISH in vHIOs, suggesting that intestinal patterning may be incomplete in HIO derived ECs at this early time point (FIG. 10).

Example V. Discussion

While organoids are genetically tractable, complex in vitro human systems, they do not entirely recapitulate the full complement of cell types or complex physiology found in native tissues (Holloway et al., 2019). Several groups have been working to improve organoids, and approaches include implementing strategies to increase organoid complexity and maturation to more accurately mimic the native tissue (Fujii et al., 2018; Low et al., 2019; Mansour et al., 2018; Ouchi et al., 2019). In the case of cell types lacking in HIOs, such as ectoderm-derived enteric neurons, co-culture techniques using enteric neuron precursors (vagal neural crest cells) have been developed, facilitating the integration of a functional enteric nervous system that can stimulate motility following transplantation (Schlieve et al., 2017; Workman et al., 2016). While HIO vascularization has been achieved following in vivo transplantation by the host vasculature, developing a native human vasculature within HIOs has been elusive. Co-culturing endothelial cells (ECs) has proven successful in other in vitro systems, including hPSC-derived hepatic endoderm cultured with primary and hPSC-derived ECs leading to complex liver bud organoids with improved hepatocyte function (Camp et al., 2017; Takebe et al., 2013, 2017). A unique aspect of hPSC-derived HIOs is the co-differentiation of both intestinal epithelium and mesenchyme, which gives rise to diverse mesenchymal lineages including smooth muscle, myofibroblasts, and fibroblasts found in HIOs in vitro and following in vivo transplantation (Finkbeiner et al., 2015b; Spence et al., 2010; Watson et al., 2014). Experiments described herein leveraged the plasticity of mesodermal progenitor cells early in HIO differentiation and demonstrated that a subset of these cells can be induced to differentiate into ECs.

Through a scRNAseq time course analysis of HIO development, it was demonstrated that differentiation of HIO mesenchyme into vasculature takes place normally during early HIO differentiation, but that these cells are rare, and are mostly lost over time. Previous work has benchmarked d0 HIOs (intestinal spheroids) to embryonic day 8.5 (E8.5) mouse intestine (Spence et al., 2010). Vascularization of the gut is thought to begin a day later, around E9.5 (Hatch and Mukouyama, 2014), which follows a similar developmental progression as young HIOs, with ECs emerging within 72 hours of 3D culture. By targeting young HIOs with exogenous vascular induction and survival cues, we were able to increase the proportion and longevity of ECs within HIOs. While this is the first report demonstrating an endogenous EC population within HIOs, EC populations have been previously described in human kidney organoids (van den Berg et al., 2018; Combes et al., 2019; Czerniecki et al., 2018; Freedman et al., 2015; Low et al., 2019; Takasato et al., 2015). Vasculature is a mesoderm derivative (Ferguson et al., 2005; Risau and Flamme, 1995), although the exact origins of intestinal and renal ECs are not fully understood. The robust mesoderm patterning that occurs in both organoid systems likely produces precursors for the native EC populations observed; however, recent pseudotime analysis performed on human kidney organoids suggests that ECs might be derived from a subset of mesodermal nephron progenitor cells that co-express KDR (Low et al., 2019). Similar to what we have observed in HIOs, ECs within human kidney organoids can be expanded with targeted growth factor modulation (Czerniecki et al., 2018; Low et al., 2019) or exposure to flow using microfluidics (Homan et al., 2019). Incorporation of flow into the vHIOs is an exciting future direction for this platform, as it might expand and enhance the stability the vascular networks and increase the appeal of this system for drug discovery.

Several studies have demonstrated that vasculature patterning is organ-specific (Daniel et al., 2018; Ding et al., 2010; Feng et al., 2019; Kalucka et al., 2020; Lee et al., 2014; Marcu et al., 2018; Nolan et al., 2013); however, whether or not organoids are programmed with this patterning information in vitro was not known. Furthermore, profiling of organ-specific ECs has not included human intestinal ECs prior to this work. Our data define a human intestinal EC signature that includes almost 150 genes that are enriched in intestinal ECs relative to lung and kidney ECs. Recent work described an adult murine EC atlas spanning 11 organ systems at single cell resolution, and provides a foundational resource to compliment the work presented here, aimed at understanding human intestinal EC patterning (Kalucka et al., 2020). Several of the validated human organ-specific markers identified in our dataset demonstrated similar expression patterns in adult mouse atlas, suggesting that organ-specific signatures established during development are retained into adulthood, although future work should confirm these findings in both developing and adult human and murine tissue. Further, a formal interrogation into mouse-human EC differences will yield an important understanding of species-specific differences. A unique strength of the current approach is the simultaneous characterization of organ-matched EC and non-EC populations. This strategy facilitated the identification of organ-specific EC-enriched signatures while at the same time understanding where and when these markers may be expressed in non-EC cell types in other organ systems.

While the vHIO platform described here constitutes the first in vitro organoid model known to contain appropriately patterned endogenous vasculature, it remains unknown what cell types and signals are responsible for inducing organ-specific gene expression and patterning in ECs. However, the scRNAseq characterization of HIOs across developmental time provides an unprecedented insight into the diverse cell types present, and future work can leverage both scRNAseq and spatial transcriptomics to interrogate this patterning, and can leverage the modular nature of the HIO system to systematically test which cell type(s) and the molecular mechanisms that are responsible for inducing intestine-specific patterning in ECs. Better understanding these mechanisms will likely shed significant light on organ development. Reciprocal signaling has been shown to occur between ECs and the surrounding organ microenvironment during development (Kao et al., 2015; Lammert, 2001; Lammert et al., 2003; Lazarus et al., 2011; Matsumoto et al., 2001; Vila Ellis et al., 2020) and ECs can influence development through the supply of membrane-bound or secreted factors, termed "angiocrine factors" (Rafii et al., 2016). Identifying these angiocrine roles of ECs has been challenging to study using in vivo animal models, as the vascular is highly sensitive to modulations in vivo (Ferrara et al., 1996; Shalaby et al., 1995), and it is technically challenging to parse out unique angiocrine roles from metabolic requirements for the vasculature. Thus, the vHIO model comprises a novel in vitro system that can be used to study the dynamic EC-organ crosstalk during intestinal development. Future work will focus on both how ECs are instructed to adopt organ-specific patterning, and also how ECs, in a perfusion independent context, might contribute to HIO development and maturation in vitro.

Taken together, the data described herein identified an unexpected, rare population of EC-like cells that arise early during HIO differentiation. By developing a method that incorporates EC-inductive and maintenance growth factors, this population can be further expanded and maintained for months in vitro. Through extensive transcriptional characterization and validation of organ-specific primary ECs across primary intestine, lung, and kidney during human development, we demonstrate the ECs co-differentiated within HIOs do undergo organ-specific patterning in vitro. vHIO improves both complexity and biological resemblance to the native developing intestine and comprises an amenable model to study EC-organ crosstalk during intestinal organogenesis.

Example VI. Materials and Methods

Human Pluripotent Stem Cells

The University of Michigan Human Pluripotent Stem Cell Research Oversight Committee approved all experiments using human embryonic (ESC) and induced pluripotent stem cells (iPSC). HIOs were generated from 3 independent lines for these studies. Control organoids were generated from hESC line H9 (NIH registry no 0062) and iPSC lines WTC11 (Kreitzer et al., 2013) and 72.3 (McCracken et al., 2014).

Derivation of Human Intestinal Organoids from hPSCs

Differentiation of hPSCs into human intestinal organoids (HIOs) was carried out as previously described (Tsai et al., 2017). Briefly, hPSCs were patterned into definitive endoderm (DE) by supplementing Roswell Park Memorial Institute 1640 (RPMI-1640) with Activin A (100 ng/ml) for 3 days and increasing HyClone FBS concentration (0%, 0.2%, 2%) each day of DE induction. Hindgut patterning was carried out through addition of FGF4 (500 ng/ml) and CHIR99021 (2 μm) to RMPI-1640 containing 2% HyClone FBS. Media was changed daily, and spheroids were collected after 5 days of hindgut patterning. Spheroids were embedded in Matrigel (8 mg/ml, Corning, 354234) and incubated in ENR media (Minigut basal media, supplemented with 100 ng/ml EGF, 100 ng/ml Noggin, and 5% R-Spondin 2 conditioned media) for 3 days to pattern duodenal identity. After 3 days, ENR media was replaced with Minigut media containing only EGF (100 ng/ml). HIOs were analyzed between 14-28 days of culture. Minigut media is composed of the following components: Advanced DMEM:12 (Life Technologies, 12634), 1×B27 supplement (Life Technologies, 17504044), L-2 mM Glutamine (Life Technologies, 25030), 15 mM HEPES (Life Technologies, 15630080). All medias used in differentiation contain 1× PenStrep (Life Technologies, 15140).

To generate vHIOs, the same protocol as above was followed with the following modifications; VEGF (50 ngl/ml) was added to ENR media after 2 days of spheroid culture. The following day, ENR was replaced by Minigut containing EGF (100 ng/ml), VEGF (50 ng/ml), bFGF (25 ng/ml), BMP4 (25 ng/ml) for 3 days. After 3 days, vHIOs were grown in Minigut media supplemented with EGF (100 ng/ml) and VEGF (25 ng/ml) for the duration of culture. vHIO and matched control HIOs were generated from H9 and WTC11 hPSC lines.

Primary Tissue Collection

Use of human tissue was reviewed and approved by The University of Michigan Institutional Review Board (IRB).

De-identified human fetal lung, intestine, and kidney tissue was obtained from the University of Washington Laboratory of Developmental Biology. Tissue was shipped overnight in Belzer-UW Cold Storage Solution (ThermoFisher, NC0952695) with cold packs, as previously published (Menon et al., 2018; Miller et al., 2020). A list of tissue specimens can be found in the key resources table.

Tissue Fixation, Paraffin Processing and Storage

Sample-matched human fetal lung, intestine, and kidney tissue samples were collected and processed into ~1-2 cm fragments. Tissues were fixed for 24 hours at room temperature in 10% Neutral Buffered Formalin (NBF), and washed with UltraPure Distilled Water (Invitrogen, 10977-015) for 3 changes for a total of 2 hours. Tissue was dehydrated in a methanol series (25%, 50%, 75%, 100%) diluted in UltraPure Distilled Water. Tissue was incubated for 60 minutes in each dehydration solution at room temperature. Tissue was stored long-term in 100% Methanol at 4° C. Prior to paraffin processing, tissue was equilibrated in 100% ethanol for an hour followed by 70% ethanol. Tissue was paraffin perfused using an automated tissue processor (Leica ASP300) with 1 hour solution changes overnight. Paraffin processed tissue was embedded and stored at room temperature with silica desiccant packets in a sealed container.

Multiplex Fluorescent In Situ Hybridization (FISH) and Protein Staining

Paraffin blocks were sectioned to generate 5 μm-thick sections. Sections were used within one week for optimal results, and the assay was carried out in RNase-free conditions by treating all materials with RNase-away (Molecular Bioproducts Inc., 7005-11) prior to use. Slides were stored at room temperature in a sealed slide box with silica desiccant packets. Slides were baked for 1 hour in a 60° C. dry oven a day prior to starting the procedure. The multiplex fluorescent in situ hybridization (FISH) protocol was performed according to the manufacturer's instructions (ACD; RNAscope Multiplex Fuorescent v2 manual protocol, 323100-USM) under standard antigen retrieval conditions and optimized protease treatment conditions for each tissue (lung 4 min., intestine 30 min., kidney 20 min, HIO 20 min). Immunofluorescent protein staining was performed as previously described (Spence et al., 2009) on 5-7 μm sections. A list of RNAscope probes, TSA reagents, and antibodies can be found in the Key Resources Table. Each FISH stain was performed on at least 2 biological replicates. All imaging was done using a Leica SP5 or Nikon A1 confocal and images were assembled using Photoshop CC. Imaging parameters were kept consistent for all images within the same experiment and any post-imaging manipulations (i.e. brightness, contrast, LUTs) were performed equally on all images from a single experiment.

Wholemount Staining of HIOs

HIOs were fixed for 30-60 minutes depending on age in 10% NBF at room temperature on a rocker. Samples were washed three times for 30-minutes in blocking solution (5% normal donkey serum in PBS with 0.1% triton). HIOs were transferred to permeabilization solution (PBS with 0.25% triton-spheroids or PBS with 0.5% triton-HIOs) for 30-60 minutes at room temperature, followed by three 30-minute washes in blocking solution and an additional 1 hour incubation in blocking solution. Primary antibodies against E-cadherin and CD144 were added to blocking solution and incubated for 24 hours at 4° C. (see key resources table for details). The following day, primary antibodies were removed and HIOs were subjected to three 30-minute washes in blocking solution. Appropriate fluorophore conjugated secondary antibodies were incubated with samples for 24 hours at 4° C. The next day, secondary antibodies were removed and HIOs were washed three times for 30-minutes in blocking solution. DAPI (0.1 mg/ml) was added to the first. Samples were mounted onto slides containing secure-seal spacers (Invitrogen, S24737). Optical clearing was achieved by incubating HIOs in Focus Clear (CelExplorer, FC-101) for 10-20 minutes at room temperature. This process was repeated with fresh Focus Clear until tissue was cleared. Focus Clear was replaced by Prolong Gold and slides were coverslipped. All imaging was done using a Nikon A1 confocal and images were assembled using Photoshop CC. Z-stack series (~0.8-1.25 μm steps) were captured and 3D rendering was performed using Imaris.

Isolation of Endothelial Cells from Primary Tissue

Primary human fetal tissue was dissociated into single cell suspensions for FACS isolation of ECs according to a previously published protocol (van Beijnum et al., 2008). Single cell suspensions were passed through a 70 μm filter, pelleted, and resuspended in staining buffer comprised of PBS with 1× PenStrep, 2 μM EDTA, and 2% FBS. Cells were stained with CD144-APC (0.88 μg/ml) and CD31-PE (0.88 μg/ml) or corresponding isotype controls (0.88 μg/ml) for 30 minutes on ice in a total volume of 100 μl/per $1 \times 10^7$ cells. Cells were washed three times in excess staining buffer accompanied by centrifugation at 300×g for 5 mins between washes. Cells were resuspended in staining buffer with DAPI (0.2 μg/ml). Antibody stained samples and controls were analyzed and sorted on a FACSAria III cell sorter (BD), and analysis was performed using BD FACSDiva software. Any post-acquisition analysis was performed using FlowJo. Cells were sorted into staining buffer, and after sorting cells were snap frozen and stored at −80° C. prior to RNA isolation.

Flow Cytometric Analysis of HIOs

HIOs were removed from Matrigel droplets and transferred to an enzymatic solution. The enzyme solution is comprised of 1 ml dispase (2.5 units/mg, Gibco, 17105-041) and 9 ml collagenase type II (0.1%, Gibco, 17101-015) in PBS per 1 gram of tissue. Tissue digestions were carried out (~1 hour) at 37° C., agitating the solution every 10 minutes via stereological pipetting. Enzymatic reactions were quenched by adding 2× the volume of serum-containing (20%) FBS media (DMEM:F12). Cell suspensions were then passed through a 70 μm filter to remove any undigested clumps. Cells were spun down (400 g for 5 mins at 4° C.) and resuspended in a staining buffer comprised of PBS with 1× PenStrep, and 2% FBS. Cells were counted using a hemacytometer, spun down (300 g for 10 minutes), and resuspended in appropriate volumes (100-200 μl) for antibody staining. Cell suspensions were stained with CD31-APC, CD144-PE, or corresponding isotype controls according to the manufacturers recommended dilution (see key resources table). Staining took place at 4° C. for 10 minutes. Cell suspensions were washed by adding 2 mls of buffer, followed by centrifugation (300 g for 10 minutes). Pellets were resuspended in 500 μl of buffer, and DAPI (0.2 μg/ml) was added to appropriate staining conditions. Flow cytometric analysis was performed using a Sony MA900 cell sorter and accompanying software.

RNA Isolation and Bulk RNAseq of Primary ECs

RNA was isolated from snap frozen cell pellets using the RNeasy Mirco Kit (74004, Qiagen), according to manufacturer's guidelines. cDNA libraries were prepared using the SMARTer Stranded Total RNA-Seq Kit v2-Pico Input (634412, Takara). A total of 32 samples were sequenced for 50-bp single-end reads across 4 lanes on an Illumina HiSeq 2500 by the University of Michigan Advanced Genomics Core. Bulk RNA sequencing analysis was performed as previously descried (Tsai et al., 2018). All reads were aligned to an index of transcripts from human genes within the Ensembl GRCh38 and quantified using Kallisto (Bray et al., 2016). Gene level data generated from Kallisto was used for TMM normalization in edgeR to create normalized data matrix of pseudocounts (Robinson et al., 2010). Principal component analysis and sample clustering were done in R using the 'cluster' and Bioconductor 'qvalue" packages (Storey et al., 2019). Genes were clustered by k-means clustering, using the KMeans function of the scikit learn package, after z-score transformation of pseudocount data (Pedregosa et al., 2011).

Single Cell Preparation of Tissue for Single Cell RNA Sequencing

Human Fetal Tissue

Cell dissociations were carried out similar to previously published methods (Miller et al., 2020). To dissociate human fetal tissue to single cells, tissue was mechanically minced into small fragments, and in a petri dish filled with ice-cold 1xHBSS (with $Mg^{2+}$, $Ca^{2+}$). This tissue was then transferred to a 15 mL conical tube. Dissociation enzymes and reagents from the Neural Tissue Dissociation Kit (Miltenyi, cat. no. 130-092-628) were used, and all incubation steps were carried out in a refrigerated centrifuge pre-chilled to 10° C. unless otherwise stated. All tubes and pipette tips used to handle cell suspensions were pre-washed with 1% BSA in HBSS to prevent adhesion of cells to the plastic. Tissue was treated for 15 minutes at 10° C. with Mix 1. Mix 2 was added to the digestion, and tissue was incubated for 10 minute increments at 10° C. until digestion was complete. After each 10 minute incubation, tissue was agitated using a P1000, and tissue digestion was visually assessed under a stereo microscope. This process continued until the tissue was fully digested. Cells were filtered through a 70 μm filter coated with 1% BSA in 1xHBSS, spun down at 500 g for 5 minutes at 10° C. and resuspended in 500 μl 1xHBSS (with $Mg^{2+}$, $Ca^{2+}$). 1 mL Red Blood Cell Lysis buffer (Roche cat. No 11814389001) was then added to the tube and the cell mixture was placed on a rocker for 15 minutes at 4° C. Cells were spun down (500 g for 5 minutes at 10° C.), and washed twice by suspension in 2 mLs of HBSS+1% BSA followed by centrifugation. Cells were counted using a hemocytometer, then spun down and resuspended (if necessary) to reach a concentration of 1000 cells/μL and kept on ice. Single cell droplets were immediately prepared on the 10× Chromium according to manufacturer instructions at the University of Michigan The Advanced Genomics Core, with a target of capturing 5,000-10,000 cells. Single cell libraries were prepared using the Chromium Next GEM Single Cell 3' Library Construction Kit v3.1 according to manufacturer instructions.

Organoids

To dissociate human intestinal organoids to single cells, organoids were mechanically isolated from Matrigel droplets and then tissue minced into small fragments using a scalpel in a petri dish filled with ice-cold 1xHBSS (with $Mg^{2+}$, $Ca^2$). This tissue was then transferred to a 15 mL conical tube. Dissociation enzymes and reagents from the Neural Tissue Dissociation Kit (Miltenyi, cat. no. 130-092-628) were used, and all incubation steps were carried out in a 37° C. incubator unless otherwise stated. All tubes and pipette tips used to handle cell suspensions were pre-washed with 1% BSA in HBSS to prevent adhesion of cells to the plastic. Tissue was treated for 15 minutes at 37° C. with Mix 1. Mix 2 was added to the digestion, and tissue was incubated for 10 minute increments at 37° C. until digestion was complete. After each 10 minute incubation, tissue was agitated using a P1000, and tissue digestion was visually assessed under a stereo microscope. This process continued until the tissue was fully digested. Cells were filtered through a 70 μm filter coated with 1% BSA in 1xHBSS, spun down at 500 g for 5 minutes at 4° C. and resuspended in 500 μl 1xHBSS (with $Mg^{2+}$, $Ca^{2+}$). Cells were counted using a hemocytometer, then spun down and resuspended (if necessary) to reach a concentration of 1000 cells/μL and kept on ice. Single cell droplets were immediately prepared on the 10× Chromium according to manufacturer instructions at the University of Michigan The Advanced Genomics Core, with a target of capturing 5,000-10,000 cells. Single cell libraries were prepared using the Chromium Next GEM Single Cell 3' Library Construction Kit v3.1 according to manufacturer instructions.

Quantification and Statistical Analysis

All graphs and statistical tests were performed in GraphPad Prism 8 software. To determine significance differences across multiple groups, a one-way Analysis of Variance (ANOVA) was performed followed by Tukey's multiple comparisons analysis comparing the mean of each group to the mean of every other group. A p-value of less than 0.05 was considered significant. On graphs, p-values for multiple comparisons after ANOVAs are reported as followed: **** p<0.0001.

Data preprocessing Cluster Identification and Cell Type Scoring

All single-cell RNA-sequencing was performed with an Illumina Novaseq 6000 at the University of Michigan Advanced Genomics Core. Raw data was processed using the 10× Genomics Cell Ranger v2.1.1-2.2.1 pipeline using human reference genome (hg19) to generate gene expression matrices. Analysis was performed using the Single Cell Analysis for Python toolbox described in previously (Wolf et al., 2018). To ensure input data were of high quality, filtering parameters for gene count range, unique molecular identifier (UMI) counts, and mitochondrial transcript fraction were imposed on each data set. After organ-specific quality filtering parameters were applied, all primary human data sets were combined for the remainder of preprocessing. Gene expression levels were log normalized, highly variable genes were extracted, and effects of UMI count and mitochondrial transcript fraction variations were regressed out by linear regression. Gene expression values were z-transformed before samples were again separated by organ for downstream analysis. A graph-based clustering approach was performed using the top 10-11 principal components. Further dimensional reduction was done using the UMAP algorithm (McInnes et al., 2018), and cluster identification was performed as previously described (Blondel et al., 2008). In certain analyses, endothelial cell clusters were identified based on expression of canonical markers (i.e. CDH5, KDR) and computationally extracted and re-clustered.

For cell type scoring of major cell classes (epithelium, mesenchyme, endothelial, neuronal, immune), gene sets for each class were curated in previously published work (Czerwinski et al., 2020; Miller et al., 2020) (Table 1), and log normalized and z-transformed raw counts were summed to generate cell type scores. For visualization of these data, cell type scores were mapped onto UMAP embeddings. For organ-specific EC gene signatures (lung EC signature (lECs); intestinal EC signature (iECs); kidney EC signature (kECs)) gene sets from the bulk RNAseq k-means clustering analysis were used. A given gene set was filtered to include the most highly enriched genes using genes with a log normalized z-score>1.8. This filtering resulted in gene lists containing 137 (lung), 89 (intestine), and 50 (kidney) genes, respectively (Supplementary Table 2). For comparison of primary fetal EC gene sets to HIO ECs, HIO ECs were queried for expression of genes from each set, and the mean log normalized and z-transformed raw counts for each gene signature set was determined (i.e. the mean expression of the lECs, iECs, and kECs sets were determined in HIO ECs). Cell scores were mapped onto the HIOEC embeddings.

TABLE 1

| IECs | iECs | kECs |
|---|---|---|
| MYZAP | FABP4 | LINC00305 |
| GCOM1 | RUNDC3B | CRHBP |
| ADRB1 | MADCAM1 | ACSM1 |
| LYPD2 | EBF3 | IRX3 |
| STAB2 | CLEC7A | QRFPR |
| RP11-341G23.2 | HES5 | PIWIL1 |
| CA4 | MEOX1 | RANBP3L |
| MYOC | GRIA2 | ASIC2 |
| VWA2 | RASA4 | IGFBP5 |
| RPI-69D17.4 | RASA4B | RP11-557H15.4 |
| RXFP1 | ATP6V1C2 | TNN |
| SCN3B | HOXD1 | SEMA5B |
| SLC6A4 | ALPL | RP11-81H14.2 |
| ZP2 | IGFBP3 | CYP26B1 |
| HPGD | C1QC | IRX5 |
| MRAP2 | RP11-92C4.6 | RIPPLY3 |
| KIRREL3-AS2 | RP11-363E6.3 | SLCO5A1 |
| RELN | PRND | CRNDE |
| ELMOD1 | ADAD2 | F8 |
| CCL21 | CFI | LINC00882 |
| RP11-436K8.1 | ABCG2 | DENND2C |
| ST8SIA6 | MYRIP | CSMD1 |
| REEP1 | RASGRF2 | TP63 |
| MRI1 | PRSS51 | RAET1G |
| PKHD1L1 | C1QB | MEIS2 |
| COLEC10 | COL15A1 | ELAVL2 |
| FCN3 | SORBS2 | A0133680.1 |
| MPP7 | MCTP1 | RYR3 |
| PROX1 | ANKRD29 | CHRM3 |
| SMOC1 | SLC45A4 | RARB |
| SLC26A4 | FABP5 | CIITA |
| RP11-449P15.1 | TSPAN2 | CD226 |
| PROX1-AS1 | SYNPO | FMNL2 |
| SLCO2B1 | CTD-2193P3.2 | SNCAIP |
| RSPH4A | MS4A6A | SLC14A1 |
| SAMD12 | RP11-875O11.3 | MAST3 |
| MID2 | CTNNBIP1 | ACSM3 |
| LONRF1 | CD320 | RP1 |
| C6orf141 | CA8 | GABRR2 |
| NCKAP5 | AQP7 | NFAT5 |
| PRX | C1QA | KIFC3 |
| LXN | HLA-DPA1 | VNN2 |
| MUC19 | PROSER2 | DHRS3 |
| SYNM | SELE | TMEM156 |
| VIPR1 | CD300LG | HLA-DOA |
| IFI27 | RND1 | RP11-219O3.2 |
| SERTAD4 | TNS4 | KHDRBS3 |
| NLRP3 | GIT2 | KCNK6 |
| ITIH3 | FAM 198B | PTPRU |
| FCGR2A | ADAMTS9 | LRP11 |
| TBX1 | ZDHHC9 | |
| GJC2 | MERTK | |
| CDC25B | CHRNE | |
| ULBP1 | MAN2B1 | |
| THEMIS2 | PRDM16 | |
| CASZ1 | KCNMB3 | |
| LY6E | EGLN1 | |
| DKK2 | RP11-455O6.2 | |
| CLU | SLC12A7 | |
| CARHSP1 | RP11-342D11.2 | |
| ACKR2 | SMAD7 | |
| RP11-6O2.4 | NPIPB11 | |
| KIT | FGL2 | |

TABLE 1-continued

| IECs | iECs | kECs |
|---|---|---|
| TSPAN11 | HMCN2 | |
| MYO7A | RIPK3 | |
| SLC43A2 | TBC1D1 | |
| RASGRP4 | C9orf43 | |
| CTB-5E10.3 | FAM171B | |
| RP11-160E2.17 | DIAPH2 | |
| VIPR1-AS1 | RP11-162D16.2 | |
| MIR181A1HG | NINJ2 | |
| CD14 | PLA2G7 | |
| QRICH2 | SNX3 | |
| ADRB2 | GBP2 | |
| IQSEC3 | CXCL12 | |
| DTL | PLCL1 | |
| PDPN | CRYBG3 | |
| CTB-50L17.14 | SEMA3G | |
| MMP17 | LACC1 | |
| FOXP1 | EHHADH | |
| KIAA1324L | TNNT3 | |
| NDRG4 | MALL | |
| HDAC9 | LRRC2 | |
| CMTM8 | JAK3 | |
| RP1-69D17.3 | NKX2-3 | |
| RAB3IL1 | IGFBP7 | |
| CLEC4M | MECOM | |
| ST8SIA6-AS1 | HLA-DPB1 | |
| DOCK5 | SIRPB2 | |
| NTS | | |
| LONRF3 | | |
| SCN3A | | |
| SSTR1 | | |
| PCLO | | |
| RAB43 | | |
| KLKB1 | | |
| TNFRSF11A | | |
| IL12A | | |
| NUDT4 | | |
| STK4 | | |
| DMTN | | |
| KHDRBS2 | | |
| SGSM1 | | |
| HSPB8 | | |
| TBX3 | | |
| CYB5A | | |
| TRPC6 | | |
| LSR | | |
| SLC2A1 | | |
| ALDH2 | | |
| TFF3 | | |
| S1PR4 | | |
| SUSD4 | | |
| SAMD14 | | |
| PDE3B | | |
| OCLN | | |
| RP5-1101C3.1 | | |
| STAP2 | | |
| SNX30 | | |
| PARD6G | | |
| MARVELD2 | | |
| ARRB1 | | |
| STON2 | | |
| SPP1 | | |
| KIAA0040 | | |
| PLXNC1 | | |
| SQRDL | | |
| FBXL7 | | |
| PRKCE | | |
| SLC45A3 | | |
| FENDRR | | |
| MRAS | | |
| ANKS1A | | |
| PLAG1 | | |
| KIAA1456 | | |
| B3GNT7 | | |
| DTX1 | | |

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

The following references denoted throughout this application are incorporated by reference in their entireties:

Aird, W. C. (2007). Phenotypic heterogeneity of the endothelium: II. Representative vascular beds. Circ. Res. 100, 174-190.

Becht, E., McInnes, L., Healy, J., Dutertre, C. A., Kwok, I. W. H., Ng, L. G., Ginhoux, F., and Newell, E. W. (2019). Dimensionality reduction for visualizing single-cell data using UMAP. Nat. Biotechnol. 37, 38-47.

van Beijnum, J. R., Rousch, M., Castermans, K., van der Linden, E., and Griffioen, A. W. (2008). Isolation of endothelial cells from fresh tissues. Nat. Protoc. 3, 1085-1091.

van den Berg, C. W., Ritsma, L., Avramut, M. C., Wiersma, L. E., van den Berg, B. M., Leuning, D. G., Lievers, E., Koning, M., Vanslambrouck, J. M., Koster, A. J., et al. (2018). Renal Subcapsular Transplantation of PSC-Derived Kidney Organoids Induces Neo-vasculogenesis and Significant Glomerular and Tubular Maturation In Vivo. Stem Cell Reports 10, 751-765.

Blondel, V. D., Guillaume, J.-L., Lambiotte, R., and Lefebvre, E. (2008). Fast unfolding of communities in large networks.

Camp, J. G., Sekine, K., Gerber, T., Loeffler-Wirth, H., Binder, H., Gac, M., Kanton, S., Kageyama, J., Damm, G., Seehofer, D., et al. (2017). Multilineage communication regulates human liver bud development from pluripotency. Nat. Publ. Gr. 109, 1-22.

Capeling, M. M., Czerwinski, M., Huang, S., Tsai, Y.-H., Wu, A., Nagy, M. S., Juliar, B., Sundaram, N., Song, Y., Han, W. M., et al. (2019). Nonadhesive Alginate Hydrogels Support Growth of Pluripotent Stem Cell-Derived Intestinal Organoids. Stem Cell Reports.

Chi, J. T., Chang, H. Y., Haraldsen, G., Jahnsen, F. L., Troyanskaya, O. G., Chang, D. S., Wang, Z., Rockson, S. G., Van De Rijn, M., Botstein, D., et al. (2003). Endothelial cell diversity revealed by global expression profiling. Proc. Natl. Acad. Sci. U.S.A 100, 10623-10628.

Combes, A. N., Zappia, L., Er, P. X., Oshlack, A., and Little, M. H. (2019). Single-cell analysis reveals congruence between kidney organoids and human fetal kidney. Genome Med. 11, 958.

Cortez, A. R., Poling, H. M., Brown, N. E., Singh, A., Mahe, M. M., and Helmrath, M. A. (2018). Transplantation of human intestinal organoids into the mouse mesentery: A more physiologic and anatomic engraftment site. Surgery.

Czerniecki, S. M., Cruz, N. M., Harder, J. L., Menon, R., Annis, J., Otto, E. A., Gulieva, R. E., Islas, L. V, Kim, Y. K., Tran, L. M., et al. (2018). High-Throughput Screening Enhances Kidney Organoid Differentiation from Human Pluripotent Stem Cells and Enables Automated Multidimensional Phenotyping. Cell Stem Cell 22, 929-940.e4.

Czerwinski, M., Holloway, E. M., Tsai, Y.-H., Wu, A., Yu, Q., Wu, J. H., Walton, K. D., Sweet, C., Childs, C., Glass, I., et al. (2020). In vitro and in vivo development of the human intestine at single cell resolution. BioRxiv 2020.01.31.928788.

Daniel, E., Azizoglu, D. B., Ryan, A. R., Walji, T. A., Chaney, C. P., Sutton, G. I., Carroll, T. J., Marciano, D. K., and Cleaver, O. (2018). Spatiotemporal heterogeneity and patterning of developing renal blood vessels. Angiogenesis 21, 617-634.

Ding, B.-S., Nolan, D. J., Butler, J. M., James, D., Babazadeh, A. O., Rosenwaks, Z., Mittal, V., Kobayashi, H., Shido, K., Lyden, D., et al. (2010). Inductive angiocrine signals from sinusoidal endothelium are required for liver regeneration. Nature 468, 310-315.

Ding, B.-S., Nolan, D. J., Guo, P., Babazadeh, A. O., Cao, Z., Rosenwaks, Z., Crystal, R. G., Simons, M., Sato, T. N., Worgall, S., et al. (2011). Endothelial-Derived Angiocrine Signals Induce and Sustain Regenerative Lung Alveolarization. Cell 147, 539-553.

Feng, W., Chen, L., Nguyen, P. K., Wu, S. M., and Li, G. (2019). Single Cell Analysis of Endothelial Cells Identified Organ-Specific Molecular Signatures and Heart-Specific Cell Populations and Molecular Features. Front. Cardiovasc. Med. 6.

Ferguson, J. E., Kelley, R. W., and Patterson, C. (2005). Mechanisms of Endothelial Differentiation in Embryonic Vasculogenesis.

Ferrara, N., Carver-Moore, K., Chen, H., Dowd, M., Lu, L., O'Shea, K. S., Powell-Braxton, L., Hillan, K. J., and Moore, M. W. (1996). Heterozygous embryonic lethality induced by targeted inactivation of the VEGF gene. Nature 380, 439-442.

Finkbeiner, S. R., Freeman, J. J., Wieck, M. M., El-Nachef, W., Altheim, C. H., Tsai, Y. H., Huang, S., Dyal, R., White, E. S., Grikscheit, T. C., et al. (2015a). Generation of tissue-engineered small intestine using embryonic stem cell-derived human intestinal organoids. Biol. Open 4, 1462-1472.

Finkbeiner, S. R., Hill, D. R., Altheim, C. H., Dedhia, P. H., Taylor, M. J., Tsai, Y.-H., Chin, A. M., Mahe, M. M., Watson, C. L., Freeman, J. J., et al. (2015b). Transcriptome-wide Analysis Reveals Hallmarks of Human Intestine Development and Maturation In Vitro and In Vivo. Stem Cell Reports 4, 1140-1155.

Freedman, B. S., Brooks, C. R., Lam, A. Q., Fu, H., Morizane, R., Agrawal, V., Saad, A. F., Li, M. K., Hughes, M. R., Werff, R. Vander, et al. (2015). Modelling kidney disease with CRISPR-mutant kidney organoids derived from human pluripotent epiblast spheroids. Nat. Commun. 6, 1035.

Fujii, M., Matano, M., Toshimitsu, K., Takano, A., Mikami, Y., Nishikori, S., Sugimoto, S., and Sato, T. (2018). Human Intestinal Organoids Maintain Self-Renewal Capacity and Cellular Diversity in Niche-Inspired Culture Condition. Cell Stem Cell 23, 787-793.e6.

Hatch, J., and Mukouyama, Y. (2014). Spatiotemporal mapping of vascularization and innervation in the fetal murine intestine. Dev. Dyn. 244, 56-68.

Hill, D. R., Huang, S., Nagy, M. S., Yadagiri, V. K., Fields, C., Mukherjee, D., Bons, B., Dedhia, P. H., Chin, A. M., Tsai, Y.-H., et al. (2017a). Bacterial colonization stimulates a complex physiological response in the immature human intestinal epithelium. Elife 6, 237ra65.

Hill, D. R., Huang, S., Tsai, Y.-H., Spence, J. R., and Young, V. B. (2017b). Real-time Measurement of Epithelial Barrier Permeability in Human Intestinal Organoids. J. Vis. Exp. e56960-e56960.

Holloway, E. M., Capeling, M. M., and Spence, J. R. (2019). Biologically inspired approaches to enhance human organoid complexity. Development 146, dev166173.

Homan, K. A., Gupta, N., Kroll, K. T., Kolesky, D. B., Skylar-Scott, M., Miyoshi, T., Mau, D., Valerius, M. T., Ferrante, T., Bonventre, J. V., et al. (2019). Flow-enhanced vascularization and maturation of kidney organoids in vitro. Nat. Methods 16, 255-262.

Kalucka, J., De Rooij, L. P. M. H., Goveia, J., Li, X., and Luo, Y. (2020). Single-Cell Transcriptome Atlas of Murine Endothelial Cells. Cell.

Kao, D.-I., Lacko, L. A., Ding, B.-S., Huang, C., Phung, K., Gu, G., Rafii, S., Stuhlmann, H., and Chen, S. (2015). Endothelial Cells Control Pancreatic Cell Fate at Defined Stages through EGFL7 Signaling. Stem Cell Reports 4, 181-189.

Kreitzer, F. R., Salomonis, N., Sheehan, A., Huang, M., Park, J. S., Spindler, M. J., Lizarraga, P., Weiss, W. A., So, P. L., and Conklin, B. R. (2013). A robust method to derive functional neural crest cells from human pluripotent stem cells. Am. J. Stem Cells 2, 119-131.

Lammert, E. (2001). Induction of Pancreatic Differentiation by Signals from Blood Vessels. Science (80-.). 294, 564-567.

Lammert, E., Cleaver, O., and Melton, D. (2003). Role of endothelial cells in early pancreas and liver development. Mech. Dev. 120, 59-64.

Lazarus, A., Lazarus, A., Del-Moral, P. M., Del-Moral, P. M., Ilovich, O., Ilovich, O., Mishani, E., Mishani, E., Warburton, D., Warburton, D., et al. (2011). A perfusion-independent role of blood vessels in determining branching stereotypy of lung airways. Development 138, 2359-2368.

Lee, J.-H., Bhang, D. H., Beede, A., Huang, T. L., Stripp, B. R., Bloch, K. D., Wagers, A. J., Tseng, Y.-H., Ryeom, S., and Kim, C. F. (2014). Lung Stem Cell Differentiation in Mice Directed by Endothelial Cells via a BMP4-NFATc1-Thrombospondin-1 Axis. Cell 156, 440-455.

Leslie, J. L., Huang, S., Opp, J. S., Nagy, M. S., Kobayashi, M., Young, V. B., and Spence, J. R. (2014). Persistence and Toxin Production by Clostridium difficile within Human Intestinal Organoids Result in Disruption of Epithelial Paracellular Barrier Function. Infect. Immun. 83, 138-145.

Low, J. H., Li, P., Chew, E. G. Y., Zhou, B., Suzuki, K., Zhang, T., Lian, M. M., Liu, M., Aizawa, E., Rodriguez Esteban, C., et al. (2019). Generation of Human PSC-Derived Kidney Organoids with Patterned Nephron Segments and a De Novo Vascular Network. Cell Stem Cell 25, 373-387.e9.

Mansour, A. A., Gonçalves, J. T., Bloyd, C. W., Li, H., Fernandes, S., Quang, D., Johnston, S., Parylak, S. L., Jin, X., and Gage, F. H. (2018). An in vivo model of functional and vascularized human brain organoids. Nat. Biotechnol. 36, 432-441.

Marcu, R., Choi, Y. J., Xue, J., Fortin, C. L., Wang, Y., Nagao, R. J., Xu, J., MacDonald, J. W., Bammler, T. K., Murry, C. E., et al. (2018). Human Organ-Specific Endothelial Cell Heterogeneity. IScience 4, 20-35.

Matsumoto, K., Yoshitomi, H., Rossant, J., and Zaret, K. S. (2001). Liver Organogenesis Promoted by Endothelial Cells Prior to Vascular Function. Science (80-.). 294, 559-563.

McCracken, K. W., Howell, J. C., Wells, J. M., and Spence, J. R. (2011). Generating human intestinal tissue from pluripotent stem cells in vitro. Nat. Protoc. 6, 1920-1928.

McCracken, K. W., Catá, E. M., Crawford, C. M., Sinagoga, K. L., Schumacher, M., Rockich, B. E., Tsai, Y.-H., Mayhew, C. N., Spence, J. R., Zavros, Y., et al. (2014). Modelling human development and disease in pluripotent stem-cell-derived gastric organoids. Nature 516, 400-404.

McInnes, L., Healy, J., and Melville, J. (2018). UMAP: Uniform Manifold Approximation and Projection for Dimension Reduction.

Menon, R., Otto, E. A., Kokoruda, A., Zhou, J., Zhang, Z., Yoon, E., Chen, Y.-C., Troyanskaya, O., Spence, J. R., Kretzler, M., et al. (2018). Single-cell analysis of progenitor cell dynamics and lineage specification in the human fetal kidney. Development 145, dev164038.

Miller, A. J., Yu, Q., Czerwinski, M., Tsai, Y.-H., Conway, R. F., Wu, A., Holloway, E. M., Walker, T., Glass, I. A., Treutlein, B., et al. (2020). In Vitro and In Vivo Development of the Human Airway at Single-Cell Resolution. Dev. Cell 0.

Múnera, J. O., Sundaram, N., Rankin, S. A., Hill, D., Watson, C., Mahe, M., Vallance, J. E., Shroyer, N. F., Sinagoga, K. L., Zarzoso-Lacoste, A., et al. (2017). Differentiation of Human Pluripotent Stem Cells into Colonic Organoids via Transient Activation of BMP Signaling. Cell Stem Cell 21, 51-64.e6.

Nolan, D. J., Ginsberg, M., Israely, E., Palikuqi, B., Poulos, M. G., James, D., Ding, B.-S., Schachterle, W., Liu, Y., Rosenwaks, Z., et al. (2013). Molecular Signatures of Tissue-Specific Microvascular Endothelial Cell Heterogeneity in Organ Maintenance and Regeneration. Dev. Cell 26, 204-219.

Orlova, V. V, van den Hil, F. E., Petrus-Reurer, S., Drabsch, Y., Ten Dijke, P., and Mummery, C. L. (2014). Generation, expansion and functional analysis of endothelial cells and pericytes derived from human pluripotent stem cells. Nat. Protoc. 9, 1514-1531.

Ouchi, R., Togo, S., Kimura, M., Shinozawa, T., Koido, M., Koike, H., Thompson, W., Karns, R. A., Mayhew, C. N., McGrath, P. S., et al. (2019). Modeling Steatohepatitis in Humans with Pluripotent Stem Cell-Derived Organoids. Cell Metab. 30, 374-384.e6.

Patsch, C., Challet-Meylan, L., Thoma, E. C., Urich, E., Heckel, T., O'sullivan, J. F., Grainger, S. J., Kapp, F. G., Sun, L., Christensen, K., et al. (2015). Generation of vascular endothelial and smooth muscle cells from human pluripotent stem cells.

Pedregosa, F., Varoquaux, G., Gramfort, A., Michel, V., Thirion, B., Grisel, O., Blondel, M., Prettenhofer, P., Weiss, R., Dubourg, V., et al. (2011). Scikit-learn: Machine learning in Python. J. Mach. Learn. Res. 12, 2825-2830.

Rafii, S., Butler, J. M., and Ding, B.-S. (2016). Angiocrine functions of organ-specific endothelial cells. Nature 529, 316-325.

Risau, W., and Flamme, I. (1995). Vasculogenesis. Annu. Rev. Cell Dev. Biol. 11, 73-91.

Sato, T., Stange, D. E., Ferrante, M., Vries, R. G. J., van Es, J. H., van den Brink, S., van Houdt, W. J., Pronk, A., van Gorp, J., Siersema, P. D., et al. (2011). Long-term Expansion of Epithelial Organoids From Human Colon, Adenoma, Adenocarcinoma, and Barrett's Epithelium. Gastroenterology 141, 1762-1772.

Schlieve, C. R., Fowler, K. L., Thornton, M., Huang, S., Hajjali, I., Hou, X., Grubbs, B., Spence, J. R., and Grikscheit, T. C. (2017). Neural Crest Cell Implantation Restores Enteric Nervous System Function and Alters the Gastrointestinal Transcriptome in Human Tissue-Engineered Small Intestine. Stem Cell Reports 9, 883-896.

Shalaby, F., Rossant, J., Yamaguchi, T. P., Gertsenstein, M., Wu, X.-F., Breitman, M. L., and Schuh, A. C. (1995).

Failure of blood-island formation and vasculogenesis in Flk-1-deficient mice. Nature 376, 62-66.
Spence, J. R., Lange, A. W., Lin, S. C. J., Kaestner, K. H., Lowy, A. M., Kim, I., Whitsett, J. A., and Wells, J. M. (2009). Sox17 Regulates Organ Lineage Segregation of Ventral Foregut Progenitor Cells. ev. Cell 17, 62-74.
Spence, J. R., Mayhew, C. N., Rankin, S. A., Kuhar, M. F., Vallance, J. E., Tolle, K., Hoskins, E. E., Kalinichenko, V. V, Wells, S. I., Zorn, A. M., et al. (2010). Directed differentiation of human pluripotent stem cells into intestinal tissue in vitro. Nature 470, 105-109.
Sriram, G., Tan, J. Y., Islam, I., Rufaihah, A. J., and Cao, T. (2015). Efficient differentiation of human embryonic stem cells to arterial and venous endothelial cells under feeder- and serum-free conditions. Stem Cell Res. Ther. 6, 1.
Takasato, M., Er, P. X., Chiu, H. S., Maier, B., Baillie, G. J., Ferguson, C., Parton, R. G., Wolvetang, E. J., Roost, M. S., Chuva de Sousa Lopes, S. M., et al. (2015). Kidney organoids from human iPS cells contain multiple lineages and model human nephrogenesis. Nature 526, 564-568.
Takebe, T., Sekine, K., Enomura, M., Koike, H., Kimura, M., Ogaeri, T., Zhang, R.-R., Ueno, Y., Zheng, Y.-W., Koike, N., et al. (2013). Vascularized and functional human liver from an iPSC-derived organ bud transplant. Nature 499, 481-484.
Takebe, T., Sekine, K., Kimura, M., Yoshizawa, E., Ayano, S., Koido, M., Funayama, S., Nakanishi, N., Hisai, T., Kobayashi, T., et al. (2017). Massive and Reproducible Production of Liver Buds Entirely from Human Pluripotent Stem Cells. Cell Rep. 21, 2661-2670.
Tsai, Y.-H., Nattiv, R., Dedhia, P. H., Nagy, M. S., Chin, A. M., Thomson, M., Klein, O. D., and Spence, J. R. (2017). In vitropatterning of pluripotent stem cell-derived intestine recapitulates in vivohuman development. Development 144, 1045-1055.
Tsai, Y. H., Czerwinski, M., Wu, A., Dame, M. K., Attili, D., Hill, E., Colacino, J. A., Nowacki, L. M., Shroyer, N. F., Higgins, P. D. R., et al. (2018). A Method for Cryogenic Preservation of Human Biopsy Specimens and Subsequent Organoid Culture. CMGH 6, 218-222.e7.
De Val, S., and Black, B. L. (2009). Transcriptional Control of Endothelial Cell Development. Dev. Cell 16, 180-195.
Vila Ellis, L., Cain, M. P., Hutchison, V., Flodby, P., Crandall, E. D., Borok, Z., Zhou, B., Ostrin, E. J., Wythe, J. D., and Chen, J. (2020). Epithelial Vegfa Specifies a Distinct Endothelial Population in the Mouse Lung. Dev. Cell.
Watson, C. L., Mahe, M. M., Múnera, J., Howell, J. C., Sundaram, N., Poling, H. M., Schweitzer, J. I., Vallance, J. E., Mayhew, C. N., Sun, Y., et al. (2014). An in vivo model of human small intestine using pluripotent stem cells. Nat. Med. 20, 1310-1314.
Wells, J. M., and Spence, J. R. (2014). How to make an intestine. Development 141, 752-760.
Wigle, J. T., and Oliver, G. (1999). Prox1 function is required for the development of the murine lymphatic system. Cell 98, 769-778.
Wigle, J. T., Harvey, N., Detmar, M., Lagutina, I., Grosveld, G., Gunn, M. D., Jackson, D. G., and Oliver, G. (2002). An essential role for Prox1 in the induction of the lymphatic endothelial cell phenotype. EMBO J. 21, 1505-1513.
Wimmer, R. A., Leopoldi, A., Aichinger, M., Wick, N., Hantusch, B., Novatchkova, M., Taubenschmid, J., Hammerle, M., Esk, C., Bagley, J. A., et al. (2019). Human blood vessel organoids as a model of diabetic vasculopathy. Nature 29, 40.
Wolf, F. A., Angerer, P., and Theis, F. J. (2018). SCANPY: large-scale single-cell gene expression data analysis. Genome Biol. 19, 15.
Workman, M. J., Mahe, M. M., Trisno, S., Poling, H. M., Watson, C. L., Sundaram, N., Chang, C.-F., Schiesser, J., Aubert, P., Stanley, E. G., et al. (2016). Engineered human pluripotent-stem-cell-derived intestinal tissues with a functional enteric nervous system. Nat. Publ. Gr. 1-13.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method, comprising:
  culturing hindgut spheroid tissue in vitro, wherein the culturing results in differentiation of the hindgut spheroid tissue into tissue comprising vascularized human intestinal organoid tissue,
  wherein the culturing of the hindgut spheroid tissue in vitro comprises the following four successive culturing steps:
  a) incubating the hindgut spheroid tissue with a media comprising EGF, Noggin and R-Spondin2 (ENR media), wherein EGF is epidermal growth factor;
  b) incubating the result of step a) with ENR media and vascular endothelial growth factor (VEGF);
  c) incubating the result of step b) with EGF, bone morphogenic protein 4 (BMP4) and basic fibroblast growth factor (bFGF); and
  d) incubating the result of step c with EGF and VEGF.

2. The method of claim 1, wherein the duration of step a is between 0.5 days and 3 days.

3. The method of claim 1, wherein the duration of step b is between 0.25 days and 1.5 days.

4. The method of claim 1, wherein the duration of step c is between 1.5 days and 5 days.

5. The method of claim 1, wherein the duration of step d is at least one day.

6. The method of claim 1, wherein the hindgut spheroid tissue is obtained through culturing definitive endoderm cells with CHIR99021 and FGF4 for between 3 days and 7 days.

7. The method of claim 6, wherein the definitive endoderm cells are obtained through culturing human pluripotent stem cells with Activin A for a period of between three days and 5 days.

8. A composition comprising vascularized human intestinal organoid tissue obtained through the method of claim 1.

9. A kit comprising vascularized human intestinal organoid tissue obtained through the method of claim 1.

* * * * *